(12) United States Patent
Bucher et al.

(10) Patent No.: US 11,135,239 B1
(45) Date of Patent: Oct. 5, 2021

(54) PHARMACEUTICAL COMPOSITIONS OF LIPOIC ACID CHOLINE ESTER SALTS AND METHODS OF TREATMENT USING SAME

(71) Applicant: Novartis AG, Basel (CH)

(72) Inventors: Christoph Bucher, Frenkendorf (DE); Dietmar Flubacher, Bad Krozingen (DE); Jeremiah Douglas Foutch, Saginaw, TX (US); Malay Ghosh, Fort Worth, TX (US); Johannes Franz Kluge, Basel (CH); Zaixing Li, Yangpu District (CN); Cale Ry McAlister, Bedford, TX (US); Liladhar Murlidhar Waykole, Succasunna, NJ (US); Jens Sören Worthmann, Basel (CH); Tingying Zhu, Pudong (CN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/199,736

(22) Filed: Mar. 12, 2021

Related U.S. Application Data

(60) Provisional application No. 63/013,836, filed on Apr. 22, 2020.

(30) Foreign Application Priority Data

Mar. 13, 2020 (WO) ................ PCT/CN2020/079271

(51) Int. Cl.
*A61K 31/724* (2006.01)
*A61K 31/381* (2006.01)
*C07D 339/04* (2006.01)
*A61K 47/38* (2006.01)
*A61K 47/02* (2006.01)
*C07C 309/72* (2006.01)

(52) U.S. Cl.
CPC .......... *A61K 31/724* (2013.01); *A61K 31/381* (2013.01); *A61K 47/02* (2013.01); *A61K 47/38* (2013.01); *C07C 309/72* (2013.01); *C07D 339/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,410,162 B2 | 4/2013 | Garner et al. |
| 8,647,612 B2 | 2/2014 | Garner et al. |
| 8,795,706 B2 | 8/2014 | Garner et al. |
| 9,044,439 B2 | 6/2015 | Garner et al. |
| 9,161,931 B2 | 10/2015 | Garner et al. |
| 9,284,305 B2 | 3/2016 | Garner et al. |
| 9,326,970 B2 | 5/2016 | Garner et al. |
| 9,517,225 B2 | 12/2016 | Garner et al. |
| 9,567,314 B2 | 2/2017 | Garner et al. |
| 10,039,743 B2 * | 8/2018 | Garner ............... A61K 31/5377 |
| 2010/0317608 A1 | 12/2010 | Garner et al. |
| 2020/0028189 A1 | 1/2020 | Rollag et al. |
| 2020/0037594 A1 | 2/2020 | Lohmeier |

FOREIGN PATENT DOCUMENTS

| | | |
|---|---|---|
| CN | 106967044 A | 7/2017 |
| CN | 107089967 A | 8/2017 |
| CN | 108586429 A | 9/2018 |
| CN | 108822077 A | 11/2018 |
| WO | 2009038656 A1 | 3/2009 |
| WO | 2015/134510 A1 | 9/2015 |
| WO | 2016/126662 A1 | 8/2016 |
| WO | 2016/164534 A1 | 10/2016 |
| WO | 2016/176089 A1 | 11/2016 |
| WO | 2017/053646 A1 | 3/2017 |
| WO | 2018/055572 A1 | 3/2018 |
| WO | 2019/150341 A1 | 8/2019 |

OTHER PUBLICATIONS

U.S. Appl. No. 15/118,910.
U.S. Appl. No. 15/762,630.
U.S. Appl. No. 13/851,355.
U.S. Appl. No. 15/091,389.
U.S. Appl. No. 15/837,171.
U.S. Appl. No. 16/791,265.
U.S. Appl. No. 16/578,368.
U.S. Appl. No. 16/812,661.
U.S. Appl. No. 16/335,762.
Zhuangzhuang et al., "Silver nanoparticles with pH induced surface charge switchable properties for anitbacterial and antiobiofilm applications," Journal of Materials Chemistry B, 7:830-840, 2019.
Parameshwaran et al., "Antioxidant-Mediated Reversal of Oxidative Damage in Mouse Modeling of Complex 1 Inhibition," Drug Development Research, 76:72-81, 2015.
Registry No. 2368996-34-1, Aug. 27, 2019.
Registry No. 2368996-30-7, Aug. 27, 2019.
Registry No. 2368996-26-1, Aug. 27, 2019.
Registry No. 2368996-23-8, Aug. 27, 2019.
Registry No. 2368996-16-9, Aug. 27, 2019.
Registry No. 2368996-13-6, Aug. 27, 2019.
Registry No. 2368996-09-0, Aug. 27, 2019.
Registry No. 2368996-05-6, Aug. 27, 2019.
Registry No. 2368996-03-4, Aug. 27, 2019.
Registry No. 2368996-00-1, Aug. 27, 2019.
Registry No. 2368995-94-0, Aug. 27, 2019.
Registry No. 2291271-32-2, Mar. 21, 2019.
Registry No. 2022211-88-5, Oct. 31, 2016.
Registry No. 1808266-58-1, Sep. 28, 2015.
Registry No. 1258491-58-5, Jan. 6, 2011.
Registry No. 1258436-42-8, Jan. 5, 2011.
Registry No. 1258436-41-7, Jan. 5, 2011.

(Continued)

*Primary Examiner* — Dale R Miller
(74) *Attorney, Agent, or Firm* — Sophie Binet Cross

(57) ABSTRACT

The present disclosure provides salts of lipoic acid choline ester (LACE), crystalline forms thereof, and methods of use thereof. The present disclosure further provides pharmaceutical compositions of LACE salts and methods of use thereof.

30 Claims, 16 Drawing Sheets

(56) References Cited

OTHER PUBLICATIONS

Registry No. 1135684-53-5, Apr. 17, 2009.
Registry No. 1135684-52-4, Apr. 17, 2009.
Registry No. 1135684-51-3, Apr. 17, 2009.
Registry No. 1135367-33-7, Apr. 16, 2009.
Registry No. 1135367-32-6, Apr. 16, 2009.
Registry No. 1135367-29-1, Apr. 16, 2009.
Registry No. 1135367-26-8, Apr. 16, 2009.
Registry No. 1135367-24-6, Apr. 16, 2009.
Registry No. 1135367-22-4, Apr. 16, 2009.
Registry No. 1135366-94-7, Apr. 16, 2009.
Registry No. 1135366-92-5, Apr. 16, 2009.
Registry No. 1135366-90-3, Apr. 16, 2009.
Registry No. 1135366-89-0, Apr. 16, 2009.
Registry No. 1135366-87-8, Apr. 16, 2009.
Registry No. 1135366-85-6, Apr. 16, 2009.
Registry No. 1135366-83-4, Apr. 16, 2009.
Registry No. 1135366-82-3, Apr. 16, 2009.
Registry No. 1062539-47-2, Oct. 17, 2008.
Registry No. 1020264-39-4, May 12, 2008.
Registry No. 945955-74-8, Sep. 4, 2007.
Registry No. 347147-94-8, Jul. 20, 2001.
Registry No. 347147-92-6, Jul. 20, 2001.
Registry No. 347147-91-5, Jul. 20, 2001.
Registry No. 326474-35-5, Mar. 8, 2001.
Registry No. 326474-34-4, Mar. 8, 2001.

* cited by examiner

PHARMACEUTICAL COMPOSITIONS OF LIPOIC ACID CHOLINE ESTER SALTS AND METHODS OF TREATMENT USING SAME

CLAIM OF PRIORITY

This application claims priority from International Patent Application No. PCT/CN2020/079271 filed Mar. 13, 2020 and U.S. Application Ser. No. 63/013,836 filed Apr. 22, 2020, each of which is incorporated herein by reference in its entirety.

FIELD

The present disclosure relates to salt forms of lipoic acid choline ester (LACE), crystalline forms thereof, and processes and methods for their manufacture. The invention also relates to pharmaceutical compositions of LACE and methods for treating ocular disorders using same.

BACKGROUND

Lipoic acid, also known as thioctic acid, is an eight carbon fatty acid with a disulfide linkage joining the carbons 6 and 8 to form an 1,2-dithiolane ring. The acid forms optical isomers of which the isomer R-α-lipoic acid is the naturally occurring isomer.

LACE is the choline ester of lipoic acid. It is believed that the choline group serves to aid permeability of lipoic acid into the eye. The bonds between lipoic acid and choline are hydrolyzed by esterases in the tear film and cornea after the eye drop is administered.

Presbyopia is an age-related inability to focus on near objects; this condition is caused by physiological changes in the microstructure of the lens resulting in loss of flexibility in the auto-adjustment of focal length and curvature of the lens to bring the visual object under focus. This condition is typically corrected by the use of corrective lenses. It has been reported that lipoic acid choline ester ("LACE") (see e.g., U.S. Pat. No. 8,410,462) may restore near vision.

Ex-vivo studies have demonstrated that lens softening can be induced pharmacologically in human donor lenses using the protein disulfide reducing agent dithiothreitol (DTT), and in mouse lenses with lipoic acid. Without being bound by theory, it is believed that this mechanism of action allows for treatment of multiple ocular diseases and disorders. These disorders include, but are not limited to, presbyopia, age-related macular degeneration, cataract and dry eye.

International Appl. Publ. No. WO 2018/055572 describes pharmaceutical compositions of LACE chloride and LACE iodide. However, as shown herein, LACE chloride, LACE iodide or both can be challenging for large scale manufacturing, can exhibit instability or combinations thereof. For example, LACE chloride has an amorphous character and high hygroscopicity. As a result, LACE chloride salt requires special handling conditions under low moisture and inert atmospheres. LACE iodide salt has a risk that it may catalyze oxidation of a redox-sensitive molecule like lipoic acid. Accordingly, there is a need for more stable salt forms of LACE, e.g., that can form crystalline forms that, for example, are even easier to manage in the chemical preparation process, and also in preparing pharmaceutical formulations.

SUMMARY

The present invention relates to salt forms of lipoic acid choline ester, crystalline forms thereof, and processes and methods for their manufacture, as well as to pharmaceutical compositions of LACE and methods for treating ocular disorders using same.

In one embodiment, the present invention provides lipoic acid choline ester tosylate having structure:

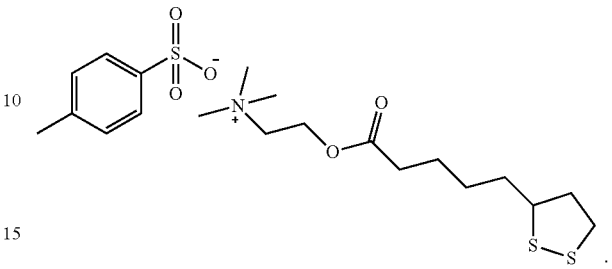

In some embodiments, the present invention provides (R) lipoic acid choline ester tosylate having structure:

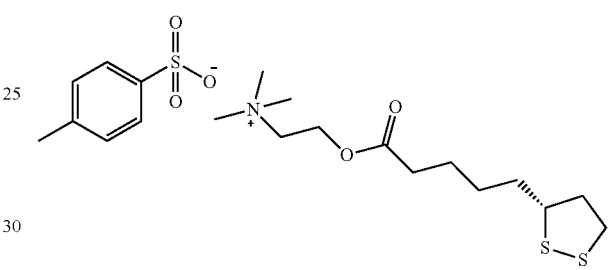

having at least about 90%, at least about 95%, at least about 96%, at least about 97%, at least about 98%, or at least about 99% enantiomeric excess of the R isomer.

In one embodiment, the present invention provides lipoic acid choline ester besylate having structure:

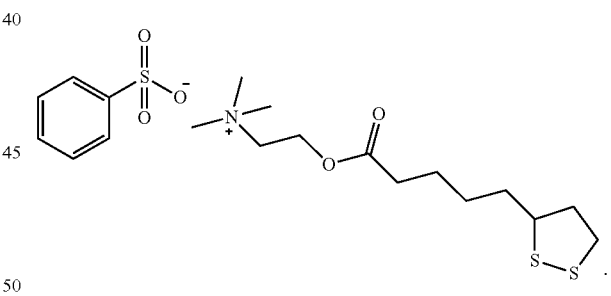

In some embodiments, the present invention provides (R) Lipoic acid choline ester besylate having structure:

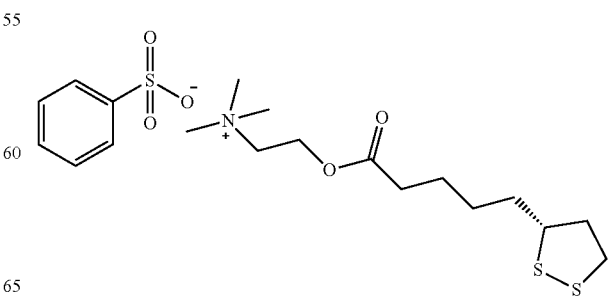

having at least about 90%, at least about 95%, at least about 96%, at least about 97%, at least about 98%, or at least about 99% enantiomeric excess of the R isomer.

In one embodiment, the present invention provides lipoic acid choline ester 3,4-dihydroxybenzoate, having structure:

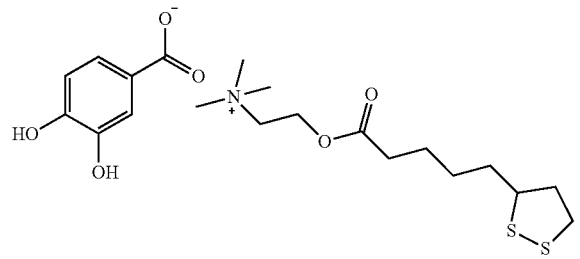

In some embodiments, the present invention provides (R) Lipoic acid choline ester 3,4-dihydroxybenzoate, having structure:

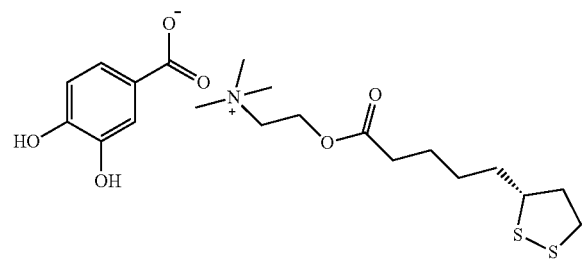 [SMILES: O=C([O-])c1ccc(O)c(O)c1 ; C[N+](C)(C)CCOC(=O)CCCC[C@@H]1CCSS1]

having at least about 90%, at least about 95%, at least about 96%, at least about 97%, at least about 98%, or at least about 99% enantiomeric excess of the R isomer.

In some embodiments, the present invention provides a crystal form A of lipoic acid choline ester (LACE) tosylate characterized by an X ray diffraction pattern having three or more peaks at 2θ values selected from 21.9, 24.9, 25.9, 26.7, 27.1, 30.4, and 32.1±0.2° 2θ.

In some embodiments, the crystal form A of LACE tosylate is characterized by an X ray diffraction pattern having four, five, six, or seven peaks at 2θ values selected from 11.4, 15.2, 18.4, 19.0, 19.4, 19.8, 21.9, 22.9, 24.9, 25.9, 26.7, 27.1, 29.6, 30.4, 32.1±0.2° 2θ. In some embodiments, the crystal form A of LACE tosylate has a X-ray diffraction pattern substantially the same as the X-ray powder diffraction pattern shown in FIG. 4. In some embodiments, the crystal form A of LACE tosylate has a FTIR spectrum substantially the same as shown in FIG. 7.

In some embodiments, the present invention provides a crystal form B of lipoic acid choline ester (LACE) tosylate characterized by an X ray diffraction pattern having three or more peaks at 2θ values selected from 7.7, 20.7, 21.4, 24.3, and 25.37±0.2° 2θ. In some embodiments, the crystal form B of LACE tosylate is characterized by an X ray diffraction pattern having four or five peaks at 2θ values selected from 7.7, 20.7, 21.4, 24.3, and 25.37±0.2° 2θ. In some embodiments, the crystal form B of LACE tosylate has an X-ray diffraction pattern substantially the same as the X-ray powder diffraction pattern shown in FIG. 8.

In some embodiments, the crystal form B of LACE tosylate has a FTIR spectrum substantially the same as shown in FIG. 9.

In some embodiments, the present invention provides a lipoic acid choline tosylate composition, comprising at least 90 weight % of LACE tosylate crystalline form B, based on the weight of the composition.

In some embodiments, the present invention provides a method of preparing a crystal form A of LACE tosylate, comprising adding an anti-solvent to a solution of LACE tosylate, to crystallize LACE tosylate as crystal form A. In some embodiments, the solution of LACE tosylate is at about 25° C.

In some embodiments, the present invention provides a method of preparing a crystal form B of LACE tosylate, comprising cooling a solution or suspension of LACE tosylate to lower than about 10° C., to crystallize LACE tosylate as crystal form B. In some embodiments, the method comprises cooling a solution or suspension of LACE tosylate to lower than 4° C., to crystallize LACE tosylate as crystal form B.

In some embodiments, the present invention provides a crystal form of lipoic acid choline ester besylate characterized by an X ray diffraction pattern having three, four, five, six, or more peaks at 2θ values selected from 4.3, 12.7, 18.4, 19.0, 19.9, 20.6, 20.8, 21.3, 23.3, 24.2, 25.5, 27.6, 31.4, 33.2, 35.0, 35.4±0.2° 2θ. In some embodiments, LACE besylate has an X-ray diffraction pattern substantially the same as the X-ray powder diffraction pattern shown in FIG. 1.

In some embodiments, the present invention provides a crystal form of lipoic acid choline ester 3,4-dihydroxy benzoate characterized by an X ray diffraction pattern having three, four, five, six, or more peaks at 2θ values selected from 6.2, 10.8, 12.5, 14.5, 15.5, 16.7, 17.4, 18.0, 18.6, 19.6, 19.9, 21.9, 24.2, 25.1, 25.8, 26.8, 27.4, 31.7±0.2° 2θ. In some embodiments, LACE 3,4-dihydroxy benzoate has an X-ray diffraction pattern substantially the same as the X-ray powder diffraction pattern shown in FIG. 13.

In some embodiments, the present invention provides a method of preparing a lipoic acid choline ester (LACE) salt, comprising reacting LACE chloride with an alkali metal salt of an acid. In some embodiments, the alkali metal salt is a sodium or potassium salt. In some embodiments, the acid is an organic acid selected from the group consisting of benzenesulfonic acid, toluenesulfonic acid, and 3,4-dihydroxybenzoic acid. In particular embodiments, the reacting is carried out in a suitable solvent. In further particular embodiments, the solvent is selected from the group consisting of acetone, acetonitrile, ethanol, and methanol. In some embodiments of the method of preparing a LACE salt, the reacting of LACE chloride with the alkali metal salt of an acid is performed at temperatures of 0° C. to about 30° C., or about room temperature, or about 20° C. to about 25° C.

In some embodiments, the present invention provides a method of preparing lipoic acid choline ester (LACE) tosylate, comprising reacting LACE chloride with sodium tosylate in an anhydrous solvent selected from the group consisting of anhydrous acetone, anhydrous methanol, and anhydrous acetonitrile. In some embodiments, the anhydrous solvent is anhydrous acetone. In alternative embodiments, the reaction is maintained at 25° C. for at least 24 hours, or at least 2, 3, 4, or 5 days.

In some embodiments, the present invention provides a method of preparing lipoic acid choline ester (LACE) tosylate, comprising:
reacting lipoic acid with an activating agent, optionally in a solvent, and optionally in the presence of a base, to yield an activated lipoic acid intermediate, reacting the activated lipoic acid intermediate with choline tosylate, optionally in a solvent, and optionally in the presence of a base, to yield LACE tosylate.

In some embodiments, the activating agent is carbonyldiimidazole. In some embodiments, the reaction of lipoic acid with the activating agent is carried out in a solvent and the presence of a base. In some embodiments, the reaction of lipoic acid with an activating agent is carried out at temperatures below 25° C. In some embodiments, the reaction of activated lipoic acid intermediate with the choline tosylate is carried out in a solvent and in the presence of a base. In some embodiments, the reaction of activated lipoic acid intermediate with choline tosylate is carried out at temperatures below 25° C., or below 30° C.

In some embodiments, lipoic acid imidazole intermediate is precipitated from the reaction by addition of an antisolvent and further isolated prior to reaction with the choline tosylate.

In particular embodiments, the reaction of lipoic acid with the activating agent is carried out in 2-methyltetrahydrofuran and the presence of N,N-diisopropylethylamine. In some embodiments, the reaction of activated lipoic acid intermediate with the choline tosylate is carried out in a solvent selected from the group consisting of acetone, acetonitrile, or a mixture thereof, and in the presence of N,N-diisopropylethylamine.

In some embodiments, the method further comprises treating LACE tosylate with activated charcoal, optionally wherein the LACE tosylate is dissolved in the solvent.

In some embodiments, the present invention provides a method of preparing a crystalline form B of LACE tosylate, comprising
dissolving LACE tosylate in a first solvent,
adding a second solvent to the solution of LACE tosyate in the first solvent,
cooling the mixture of LACE tosylate, first solvent, and second solvent to temperatures below 10° C.,
to crystallize crystalline form B of LACE tosylate.

In some embodiments, the first solvent is acetonitrile, ethanol, water, or mixtures thereof, and the second solvent is acetone, 2-butanone, methyl tert-butyl ketone, tetrahydrofuran, or mixtures thereof.

In some embodiments, the present invention provides a method of preparing LACE besylate, comprising reacting LACE chloride with sodium besylate in a solvent selected from the group consisting of anhydrous acetone, anhydrous methanol, and anhydrous acetonitrile.

In some embodiments, the present invention provides a method of preparing LACE 3,4-dihydroxybenzoate, comprising reacting LACE chloride with sodium 3,4-dihydroxybenzoate in solvent selected from the group consisting of anhydrous acetone, anhydrous methanol, or anhydrous acetonitrile.

In some embodiments, the reacting is carried out at 25° C. for at least 24 hours, or at least 2, 3, 4, or 5 days.

In some embodiments, the present invention provides a pharmaceutical composition, comprising an effective amount of lipoic acid choline ester tosylate or lipoic acid choline ester besylate, and a pharmaceutically acceptable excipient. In some embodiments, the pharmaceutical composition comprises the lipoic acid choline ester tosylate in substantially pure form. In some embodiments, pharmaceutical composition comprises the lipoic acid choline ester besylate in substantially pure form.

In some embodiments, the pharmaceutical composition is formulated for ocular use.

In some embodiments, the present invention provides a pharmaceutical composition, wherein the lipoic acid choline ester is in solution.

In some embodiments, the present invention provides a pharmaceutical composition as described herein, for use in the treatment of presbyopia.

In some embodiments, the present invention provides a pharmaceutical composition, comprising:
a lipoic acid choline ester salt,
hydroxypropyl-β-cyclodextrin,
optionally, a tonicity agent,
optionally, a viscosity modifying agent,
optionally, a buffer,
optionally, a preservative.

In some embodiments, the pharmaceutical composition comprises:
about 0.5% w/v to about 5% w/v (based on the lipoic acid choline ester) of the lipoic acid choline ester salt,
about 1.5% w/v to about 25% w/v of hydroxypropyl-β-cyclodextrin,
0% w/v to about 1% w/v of a tonicity agent,
0% w/v to about 1% w/v of a viscosity modifying agent,
0% w/v to about 1% w/v of a buffer,
0% w/v to about 0.5% w/v of a preservative.

In some embodiments, the lipoic acid choline ester salt is lipoic acid choline ester tosylate, lipoic acid choline ester iodide, lipoic acid choline ester besylate or lipoic acid choline ester chloride. In particular embodiments, the lipoic acid choline ester salt is lipoic acid choline ester tosylate. In any of the embodiments described herein, the lipoic acid choline ester is substantially (R)-lipoic acid choline ester.

In some embodiments, the pharmaceutical composition comprises about 0.01% w/v to about 20% w/v of a viscosity modifying agent. In some embodiments, the viscosity modifying agent is selected from the group consisting of polyethylene glycols, cellulosic agents, and mixtures thereof. In particular embodiments, the viscosity modifying agent is selected from the group consisting of cellulosic agents. In further particular embodiments, the viscosity modifying agent comprises hydroxypropylmethyl cellulose. In particular embodiments, the viscosity modifying agent is substantially all hydroxypropylmethyl cellulose.

In some embodiments, the pharmaceutical composition comprises about 1 mM to about 300 mM of a tonicity agent selected from the group consisting of ionic tonicity agents, nonionic tonicity agents, and mixtures thereof. In particular embodiments, the tonicity agent is sodium chloride, potassium chloride, or mixtures thereof, present in an amount of about 1 mM to about 150 mM, or a tonicity agent selected from the group consisting of mannitol, dextrose, and mixtures thereof in an amount of about 1 mM to about 300 mM. In particular embodiments, the tonicity agent is selected from the group consisting of sodium chloride, potassium chloride, mannitol, dextrose, glycerin, propylene glycol and mixtures thereof. In further particular embodiments, the tonicity agent comprises sodium chloride or potassium chloride in an amount of from 0.01% w/v to about 1% w/v. In further particular embodiments, the tonicity agent is substantially all sodium chloride in an amount of from 0.01% w/v to about 1% w/v.

In some embodiments, the pharmaceutical composition comprises about 0.01% w/v to about 1% w/v of a buffer. In particular embodiments, the buffer is selected from the group consisting of phosphate buffers (e.g., sodium phosphate monobasic monohydrate, sodium phosphate dibasic anhydrous), acetate buffer, citrate buffer, borate buffers, and HBSS (Hank's Balanced Salt Solution). In particular embodiments, the buffer comprises acetate, e.g., sodium acetate. In further particular embodiments, the buffer is substantially all acetate buffer.

In some embodiments, the pharmaceutical composition has a pH of about 4.3 to about 4.7.

In some embodiments, the pharmaceutical composition comprises 0% w/v to about 0.5% w/v of a preservative. In particular embodiments, the preservative is selected from the group consisting of benzalkonium chloride, sorbic acid, boric acid, and mixtures thereof. In particular embodiments, the pharmaceutical composition does not include benzalkonium chloride. In further particular embodiments, the pharmaceutical composition does not include any preservative.

In some embodiments, the pharmaceutical composition does not include a biochemical energy source, e.g., alanine.

In some embodiments, the pharmaceutical compositions described herein do not include benzalkonium chloride. In particular embodiments, the pharmaceutical composition does not include a preservative and wherein the pharmaceutical composition meets US Pharmacopoeia preservation standards for sterile parenteral multi-dose compositions.

In some embodiments, the pharmaceutical composition comprises hydroxypropyl-β-cyclodextrin in an amount about 1-2 molar equivalents of the lipoic acid choline ester salt. In particular embodiments, the pharmaceutical composition comprises hydroxypropyl-β-cyclodextrin in an amount equimolar to the lipoic acid choline ester salt.

In some embodiments, the pharmaceutical composition described herein has an osmolality of about 250 mOsm to about 425 mOsm, or about 250 mOsm to about 330 mOsm.

In particular embodiments, the present invention provides a pharmaceutical composition, comprising:

about 0.5% w/v, about 1.3% w/v, about 2.3% w/v, about 3% w/v, about 4% w/v, or about 5% w/v (based on the lipoic acid choline ester) of lipoic acid choline ester tosylate, hydroxypropyl-β-cyclodextrin in an amount about equimolar to the lipoic acid choline ester, about 0.1% w/v to about 1% w/v of sodium chloride, about 0.1% w/v to about 0.75% w/v of hydroxypropylmethyl cellulose, and about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

In some embodiments, the pharmaceutical composition comprises about 1.5% w/v, about 2.5% w/v, about 3.2% w/v, about 3.3% w/v, about 6.3% w/v, about 6.7% w/v, about 11.2% w/v, about 11.5% w/v, about 15.0% w/v, or about 19.6% w/v of hydroxypropyl-β-cyclodextrin.

In some embodiments, the pharmaceutical compositions described herein is a sterile, aqueous solution.

In any of the pharmaceutical compositions described herein, the lipoic acid choline ester salt is substantially all (R)-lipoic acid choline ester salt.

In some embodiments, the present invention provides a process of making a pharmaceutical composition by the process of:

adding to water an amount of lipoic acid choline ester salt and hydroxypropyl-beta-cyclodextrin to prepare a solution of lipoic acid choline ester and hydroxypropyl-beta-cyclodextrin, optionally adding a tonicity agent, a viscosity modifying agent, a buffer, and a preservative to the solution of lipoic acid choline ester and hydroxypropyl-beta-cyclodextrin, adjusting the pH with an acid or base, optionally adding water to adjust the concentration of LACE salt to the final concentration, and optionally sterilizing the solution to provide the pharmaceutical composition.

In some embodiments, provided herein is a pharmaceutical composition prepared by the process of:

adding to water an amount of lipoic acid choline ester salt and hydroxypropyl-beta-cyclodextrin to prepare a solution of lipoic acid choline ester and hydroxypropyl-beta-cyclodextrin, optionally adding a tonicity agent, a viscosity modifying agent, a buffer, and a preservative to the solution of lipoic acid choline ester and hydroxypropyl-beta-cyclodextrin, adjusting the pH with an acid or base, optionally adding water to adjust the concentration of LACE salt to the final concentration, and optionally sterilizing the solution to provide the pharmaceutical composition.

In some embodiments, the present invention provides a method for treating or preventing a disease or disorder associated with oxidative damage, comprising ocularly administering to a patient a pharmaceutical composition according to any of the embodiments described herein.

In some embodiments, the present invention provides a method for treating or preventing a disease or disorder associated with oxidative damage, comprising ocularly administering to a patient a lipoic acid choline ester salt at a total daily dose of about 0.1 mg to about 5 mg of lipoic acid choline ester, about 0.2 mg to about 3 mg of lipoic acid choline ester, about 0.4 mg to about 2.5 mg of lipoic acid choline ester, or of about 0.2 mg, about 0.4 mg, about 0.5 mg, about 0.8 mg, about 0.9 mg, about 1 mg, about 1.1 mg, about 1.2 mg, about 1.4 mg, about 1.5 mg, about 1.6 mg, about 2.1 mg, about 2.4 mg, about 2.8 mg, or about 3.2 mg, of lipoic acid choline ester, wherein the lipoic acid choline ester is in a salt form selected from the group consisting of lipoic acid choline ester tosylate, lipoic acid choline ester besylate, lipoic acid choline ester chloride or lipoic acid choline ester iodide.

In some embodiments, the lipoic acid choline ester is administered to the patient in the form of a pharmaceutical composition according to any of the embodiments described herein. In some embodiments, the method comprises ocularly administering to the patient a total daily dose of lipoic acid choline ester tosylate of about 0.2 mg to about 7 mg, or about 0.5 mg to about 5 mg, or about 0.7 mg to about 3.5 mg, or about 0.3 mg, about 0.6 mg, about 0.8 mg, about 1.0 mg, about 1.5 mg, about 1.7 mg, about 2.0 mg, about 2.2 mg, about 2.3 mg, about 2.5 mg, about 2.6 mg, about 3.0 mg, about 3.4, about 3.9, about 4.5, about 5.0, about 6.0, or about 6.7 mg.

In some embodiments, the present invention provides a method of improving distance corrected near vision acuity (DCNVA) in a subject in need thereof, comprising ocularly administering an effective amount of a pharmaceutical composition according to any of the embodiments described herein. In some embodiments, change from baseline in binocular DCNVA of the subject is assessed. In some embodiments, change from baseline in monocular DCNVA of the subject is assessed. In particular embodiments, the DCNVA is improved by at least 1 letter, at least 2 letters, at least 3 letters, at least 4 letters, or at least 5 letters.

In some embodiments, the present invention provides a method of increasing the accommodative amplitude of a lens by at least 0.1 diopters (D) in a subject in need thereof, comprising ocularly administering an effective amount of a pharmaceutical composition according to any of the embodiments described herein. In particular embodiments, the accommodative amplitude of the lens is increased by at least 0.2, 0.5, 1, 1.2, 1.5, 1.8, 2, 2.5, 3, or 5 diopters.

In any of the methods described herein, subject suffers from a disease or disorder associated with oxidative damage. In particular embodiments, the disease or disorder associated with oxidative damage is presbyopia or cataract e.g., early stage cataract or juvenile cataracts.

In some embodiments, the pharmaceutical compositions described herein meet one or more of the following conditions:
wherein the pharmaceutical composition comprises at least 95%, at least 96%, at least 97%, or at least 98% of the initial amount of lipoic acid choline ester after storage at 25° C. for 10 weeks;
wherein the pharmaceutical composition comprises at least 95%, at least 96%, at least 97%, or at least 98% of the initial amount of lipoic acid choline ester after storage at 25° C. for 13 weeks; or
wherein the pharmaceutical composition comprises at least 80%, at least 85%, at least 86%, at least 87%, or at least 88% of the initial amount of lipoic acid choline ester after storage at 40° C. for 13 weeks.

In some embodiments, the pharmaceutical compositions described herein, when administered to a rabbit, result in a maximum aqueous humor lipoic acid concentration (Cmax) that is at least 2 times, at least 2.5 times, at least 3 times, at least 3.5 times at least 4 times, at least 5 times at least 6 times, at least 7 times, at least 8 times, at least 9 times, or at least 10 times the aqueous humor lipoic acid concentration of an pharmaceutical composition that does not include a viscosity modifying agent.

In some embodiments, the pharmaceutical compositions described herein, when administered to a rabbit, results in a maximum corneal lipoic acid concentration (Cmax) that is at least 2 times, at least 2.5 times, at least 3 times, at least 3.5 times at least 4 times, at least 5 times at least 6 times, at least 7 times, at least 8 times, at least 9 times, or at least 10 times the aqueous humor lipoic acid concentration of a pharmaceutical composition that includes a viscosity modifying agent. In particular embodiments, the viscosity modifying agent is hydroxypropylmethyl cellulose.

In particular embodiments, the pharmaceutical compositions described herein include less than about 2%, less than about 1%, less than about 0.5%, less than about 0.4%, less than about 0.3%, less than about 0.2% or less than about 0.1% of associative species of LACE, when measured in terms of HPLC peak area relative to LACE.

Specific embodiments of the invention will become evident from the following more detailed description of certain specific embodiments and the claims.

DETAILED DESCRIPTION

Figure 1:
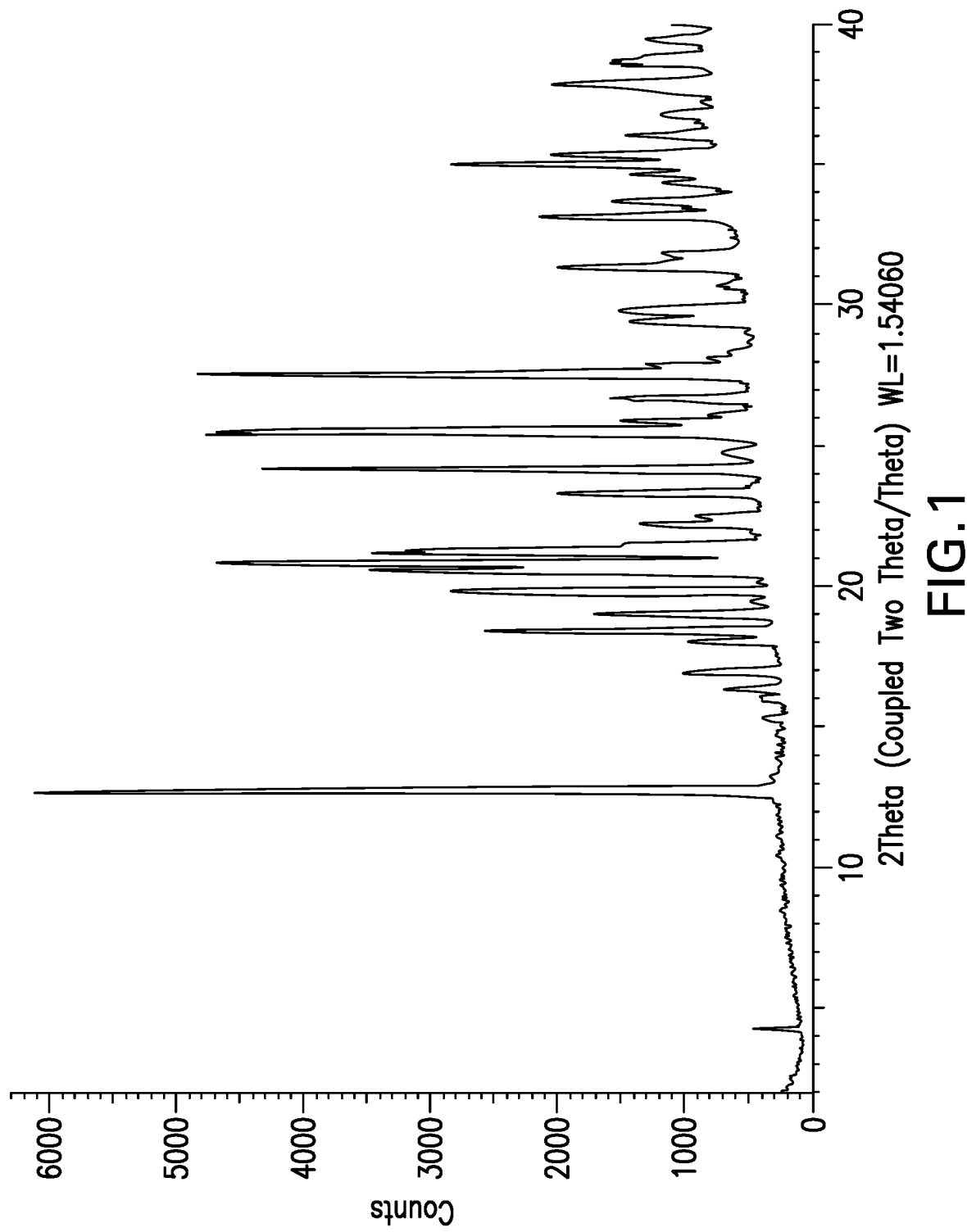
FIG. 1 provides the XRPD pattern of a crystalline form of lipoic acid choline ester besylate.
Figure 2:
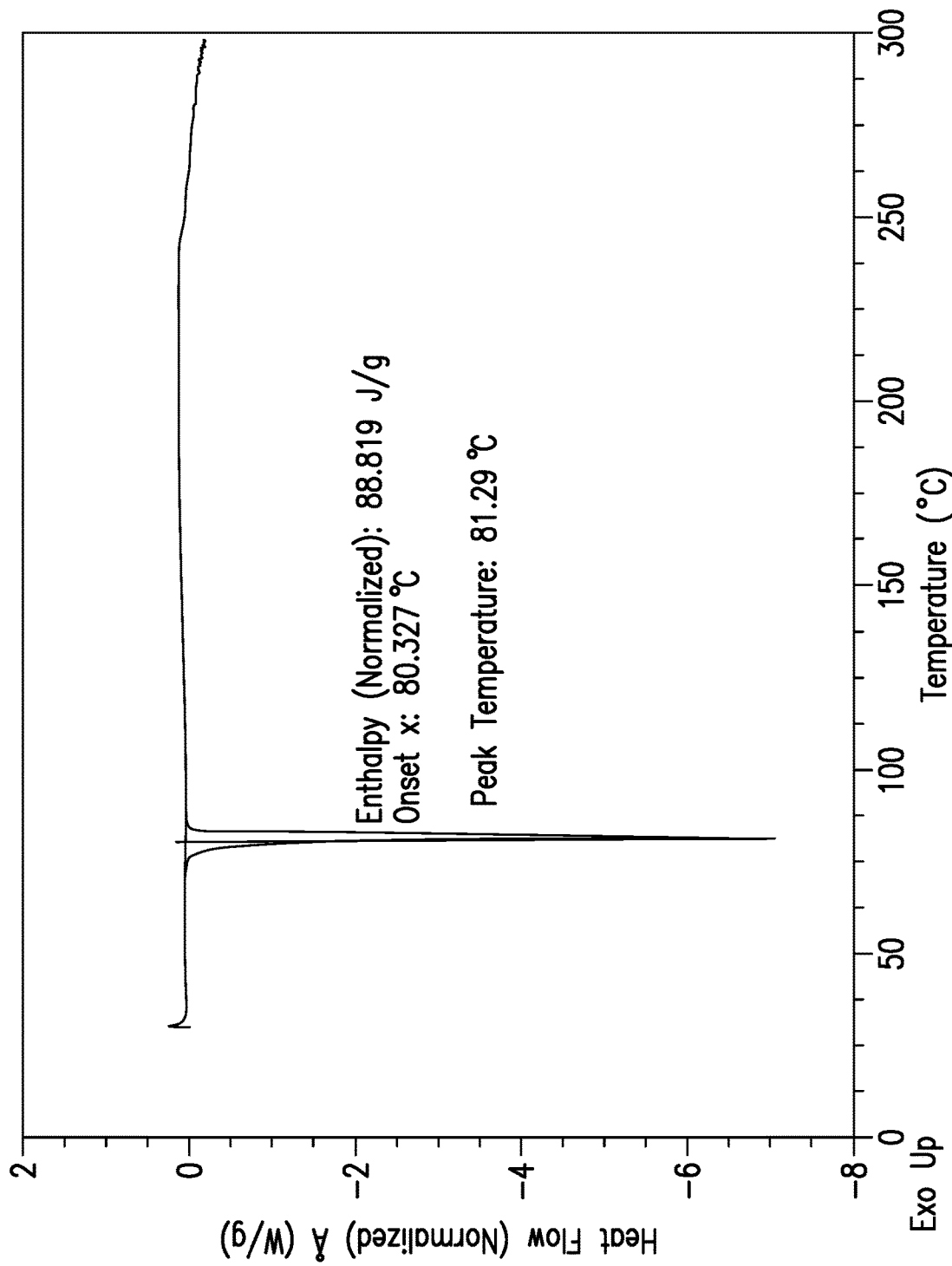
FIG. 2 provides differential scanning calorimetry thermogram of lipoic acid choline ester besylate salt.
Figure 3:
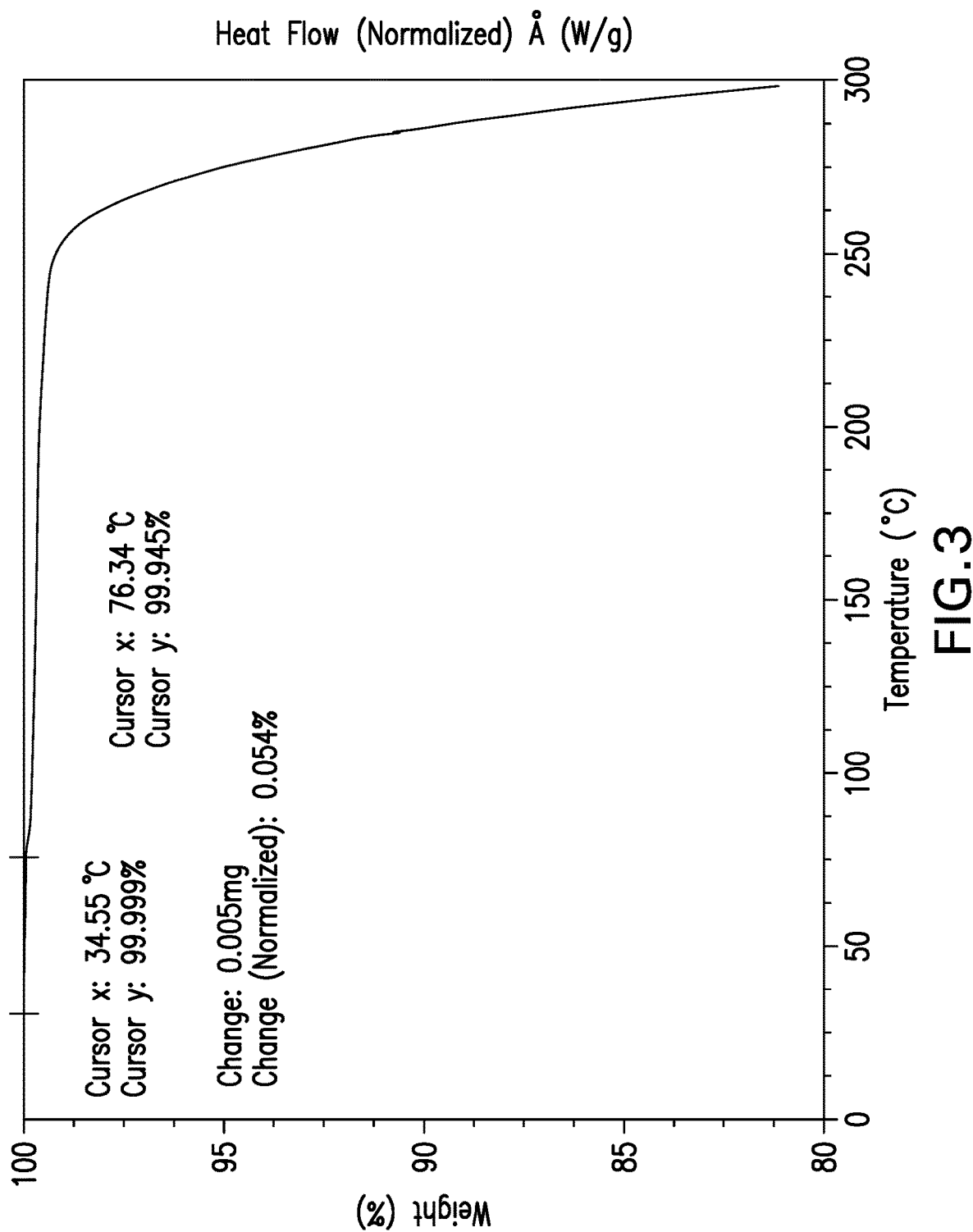
FIG. 3 provides thermogravimetric analysis thermogram of lipoic acid choline ester besylate salt.

The language "effective amount" of the compounds described herein, refers to that amount of a therapeutic compound necessary or sufficient to perform its intended function within a mammal (e.g., human). An effective amount of the therapeutic compound can vary according to factors such as the amount of the causative agent already present in the mammal, the age, sex, and weight of the mammal, and the ability of the therapeutic compounds of the present disclosure to treat the ocular surface disorder and/or symptoms thereof in the mammal.

The phrase "ophthalmically compatible" refers to formulations, polymers and other materials and/or dosage forms which are suitable for use in contact with the ocular tissues of human beings and animals without excessive toxicity, irritation, allergic response, or other problem or complication, commensurate with a reasonable benefit/risk ratio.

As used herein, the term "treat", "treating" or "treatment" in connection to a disease or disorder refers in some embodiments, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder or symptom thereof.

As used herein, the term "subject" or "patient" refers to human and non-human mammals, including but, not limited to, primates, rabbits, pigs, horses, dogs, cats, sheep, and cows. In particular embodiments, a subject or patient is a human. In some embodiments, the term "patient" or "subject" refers to a human being who is diseased with the condition (i.e., disease or disorder) described herein and who would benefit from the treatment. As used herein, a subject is "in need of" a treatment if such subject (patient) would benefit biologically, medically or in quality of life from such treatment. In particular embodiments, the subject is an adult human of at least about 18 years of age. In some embodiments, the subject is an adult human from about 40 years of age to about 85 years of age, about 45 to about 65 years of age, about 45 to about 55 years of age, about 55 to about 65 years of age, or about 65 to about 75 years of age.

As used herein, "ocular surface" refers to the outer surface of the eye, which anatomically comprises the cornea (with epithelium, bowman layer, stroma, descement membrane, endothelium), conjunctiva, cul de sac, and the corneo-scleral junction, i.e. limbus.

As used herein, ocular administration is synonymous with ophthalmic administration and includes administration to all parts of the eye including all parts of the ocular surface such as the cornea, conjunctiva, the cul de sac and the corneo-scleral junction, i.e., limbus.

As used herein, "placebo" refers to an ophthalmic formulation that includes all the components of the administered drug composition without the drug. In some embodiments, the placebo may include additional components other than the drug, such as preservatives, pH adjusting agents, tonicity modifiers, etc.

As used herein, the term "about" refers to a range of values+10% of a specified value.

As used herein, "polymorph" refers to crystalline forms having the same chemical composition but different spatial arrangements of the molecules, atoms, and/or ions forming the crystal.

As used herein, "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule of LACE within the crystalline lattice structure.

As used herein, "co-crystal" refers to a solid that is a neutral crystalline single phase material comprising two or more different molecules and/or ionic compounds that are neither solvates nor salts. The two or more different molecules and/or ionic compounds are generally in a stoichiometric ratio. For example, LACE: 3,4-dihydroxybenzoate may be a co-crystal with Na-3,4-dihydroxybenzoate and NaCl.

As used herein, arlipoic acid (R)-lipoic acid refers to arlipoic acid having the structure:

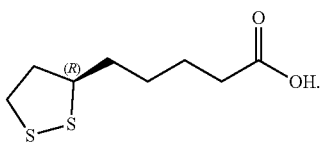

As used herein, (R)-lipoic acid choline ester refers to arlipoic acid choline ester or arlipoate choline ester having the formula:

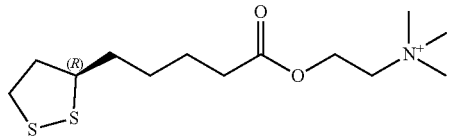

As used herein, (R)-lipoic acid choline ester salt refers to arlipoic acid choline ester salt or arlipoate choline ester salt having the formula, wherein X- is the counterion:

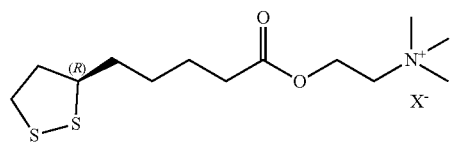

As used herein, "tosylate" refers to 4-toluenesulfonate and "besylate" refers to benzenesulfonate, having the following structures as anions:

tosylate besylate.

As used herein "amorphous" refers to a solid form of a molecule, atom, and/or ions that is not crystalline. An amorphous solid does not display a definitive X-ray diffraction pattern.

As used herein, "substantially pure," when used in reference to a form, means a form having a purity greater than 90 weight %, including greater than 90, 91, 92, 93, 94, 95, 96, 97, 98, and 99 weight %, and also including equal to about 100 weight % of LACE, based on the weight of the compound. The remaining material comprises other form(s) of the compound, and/or reaction impurities and/or processing impurities arising from its preparation. For example, a crystalline form of LACE salt may be deemed substantially pure in that it has a purity greater than 90 weight %, as measured by means that are at this time known and generally accepted in the art, where the remaining less than 10 weight % of material comprises other form(s) of LACE and/or reaction impurities and/or processing impurities.

As used herein, "substantially all" when used in reference to a component or composition means that the component forms at least 90 weight %, including greater than 90, 91, 92, 93, 94, 95, 96, 97, 98, and 99 weight % of the composition.

As used herein, "crystal form," "crystalline form," "modification," "polymorph," or "polymorphic form" in upper or lower case are used interchangeably and refer to crystalline or polymorphic forms of lipoic acid choline ester (LACE) salts, having the structure shown below, wherein X is the anionic counterion.

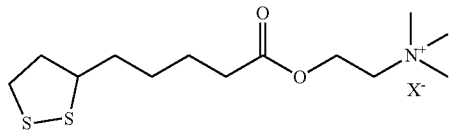

In particular embodiments, LACE has the R enantiomeric form, having the following structure:

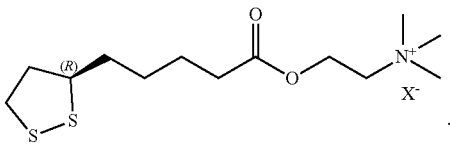

LACE salts may be in amorphous or crystalline forms. As used herein, "polymorphic forms," "polymorphs," or "co-crystal" is intended to encompass crystalline hydrates or other crystalline solvates of LACE salts.

The term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Any chemical formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, and oxygen, such as $^3$H, $^{11}$C, $^{13}$C, $^{14}$C, and $^{15}$N. Accordingly, it should be understood that methods of the present invention can or may involve compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. Isotopically-labeled compounds can generally be prepared by conventional techniques known to those skilled in the art, e.g., using an appropriate isotopically-labeled reagents in place of the non-labeled reagent previously employed.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Persons of skill in the art will appreciate that identical concentrations of any of the components in the pharmaceutical compositions described herein may be expressed in different units, for example, percent weight per volume (% w/v), milligram per milliliter (mg/ml), molar (M) or millimolar (mM).

Solid Forms of Lipoic Acid Choline Ester

The solid form of LACE chloride is amorphous, highly hygroscopic, thermally labile and highly oxygen sensitive. This results in an active pharmaceutical ingredient that is difficult to handle under normal conditions of manufacturing and storage. The novel salt forms described in the present disclosure overcome these challenges to provide a salt form that has good handling properties as described herein.

Accordingly, in one aspect, the present invention relates to salts of lipoic acid choline ester. In one aspect, the present invention relates to lipoic acid choline ester salts that absorbs moisture at less than about 5%, less than about 4%, less than about 3% or less than about 2%, under conditions of up to 60% RH and/or exhibits less than 2% degradation after a 1 week at 40° C. In particular embodiments, the lipoic acid choline ester salt is lipoic acid choline ester tosylate.

In some embodiments, the present invention relates to crystalline salts of lipoic acid choline ester. In some embodiments, the present invention relates to lipoic acid choline ester tosylate. In particular embodiments, the present invention relates to crystalline lipoic acid choline ester tosylate. In particular embodiments, the lipoic acid choline tosylate is in substantially pure form. In particular embodiments, the lipoic acid choline ester tosylate is (R) lipoic acid choline ester tosylate having structure:

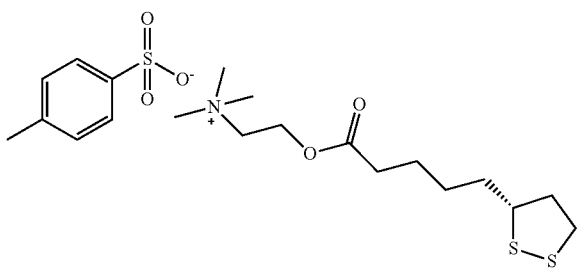 [SMILES: Cc1ccc(S(=O)(=O)[O-])cc1 ; C[N+](C)(C)CCOC(=O)CCCC[C@@H]1CCSS1]

having at least about 90%, at least about 95%, at least about 96%, at least about 97%, at least about 98%, or at least about 99% enantiomeric excess of the R isomer. In particular embodiments, the lipoic acid choline ester tosylate is substantially all (R) lipoic acid choline ester tosylate.

In some embodiments, the present invention relates to lipoic acid choline ester besylate. In particular embodiments, the present invention relates to crystalline lipoic acid choline ester besylate. In particular embodiments, the lipoic acid choline ester besylate is in substantially pure form. In particular embodiments, the lipoic acid choline ester besylate is (R) lipoic acid choline ester besylate having structure:

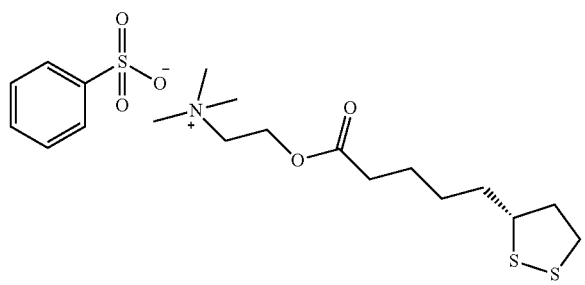 [SMILES: O=S(=O)([O-])c1ccccc1 ; C[N+](C)(C)CCOC(=O)CCCC[C@@H]1CCSS1]

having at least about 90%, at least about 95%, at least about 96%, at least about 97%, at least about 98%, or at least about 99% enantiomeric excess of the R isomer. In particular embodiments, the lipoic acid choline ester besylate is substantially all (R) lipoic acid choline ester besylate.

In some embodiments, the present invention relates to lipoic acid choline ester iodide or substantially all (R)-lipoic acid choline ester iodide. In particular embodiments, the present invention relates to crystalline salts of lipoic acid choline iodide. In some embodiments, the present invention relates to lipoic acid choline ester 3,4-dihydroxybenzoate or substantially all (R)-lipoic acid choline ester 3,4-dihydroxybenzoate. In particular embodiments, the present invention relates to crystalline form of lipoic acid choline 3,4-dihydroxybenzoate.

Figure 4:
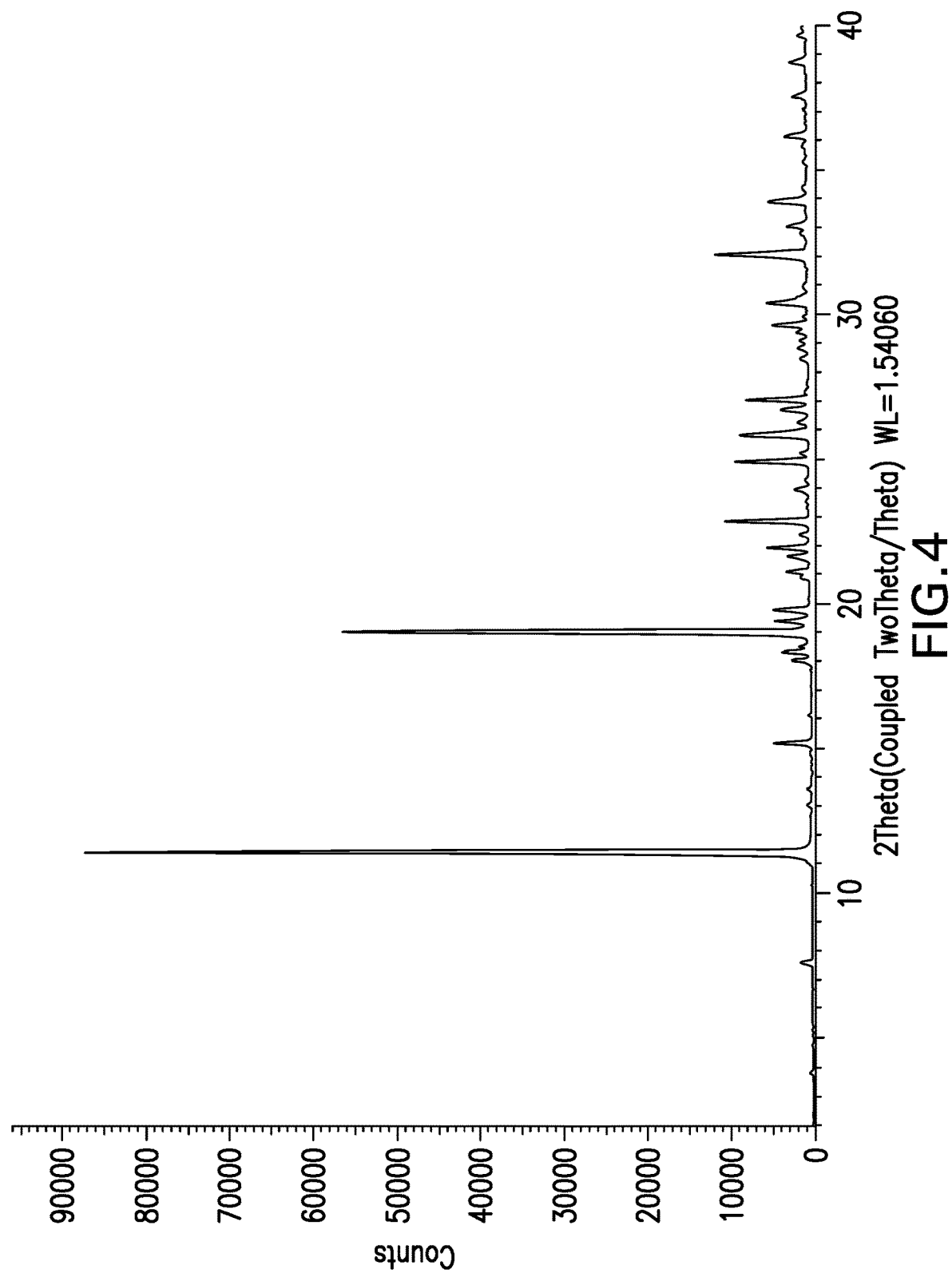
FIG. 4 provides the x-ray diffraction pattern for lipoic acid choline ester tosylate crystalline Form A.
Figure 5:
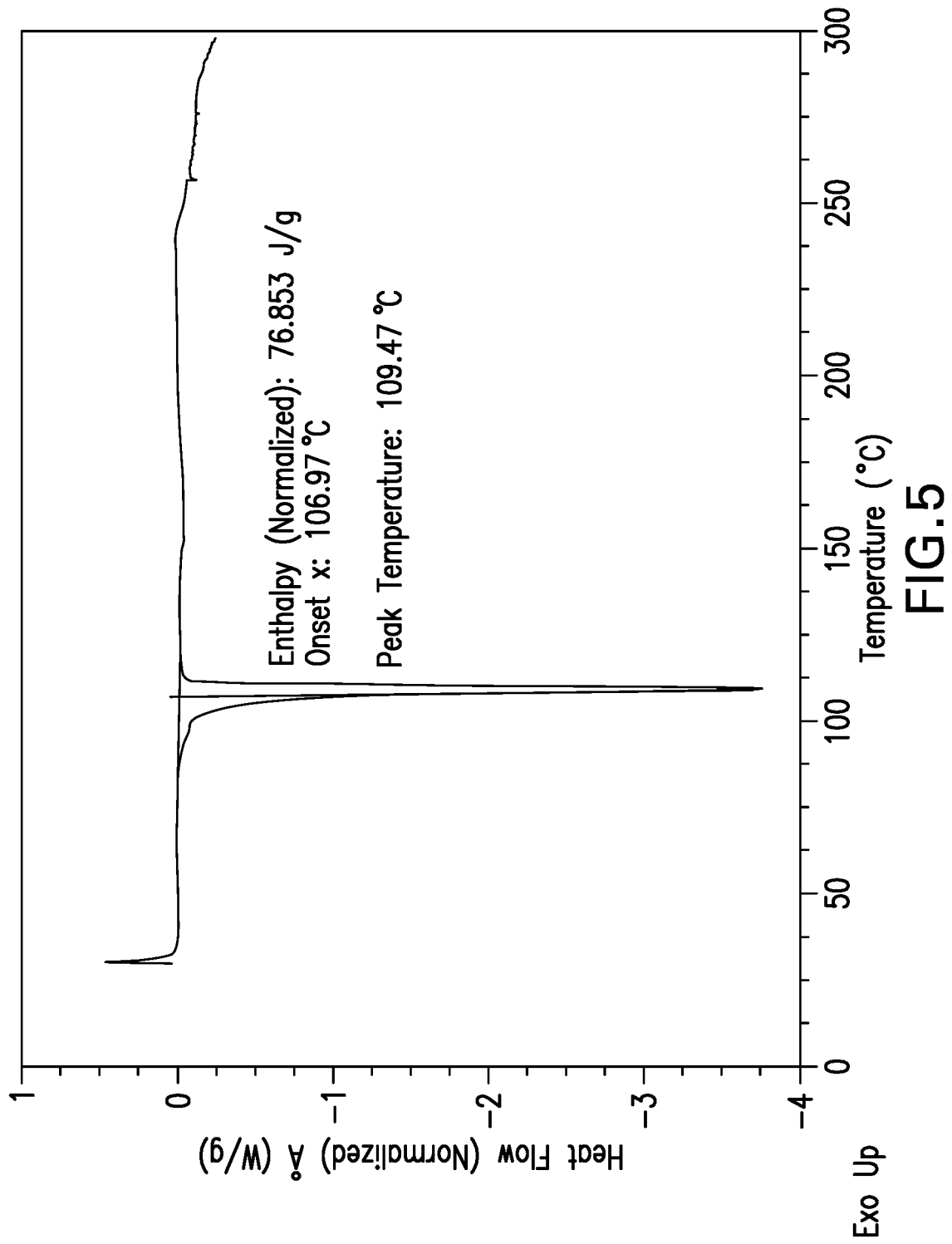
FIG. 5 provides the differential scanning calorimetry thermogram of LACE tosylate Form A.
Figure 6:
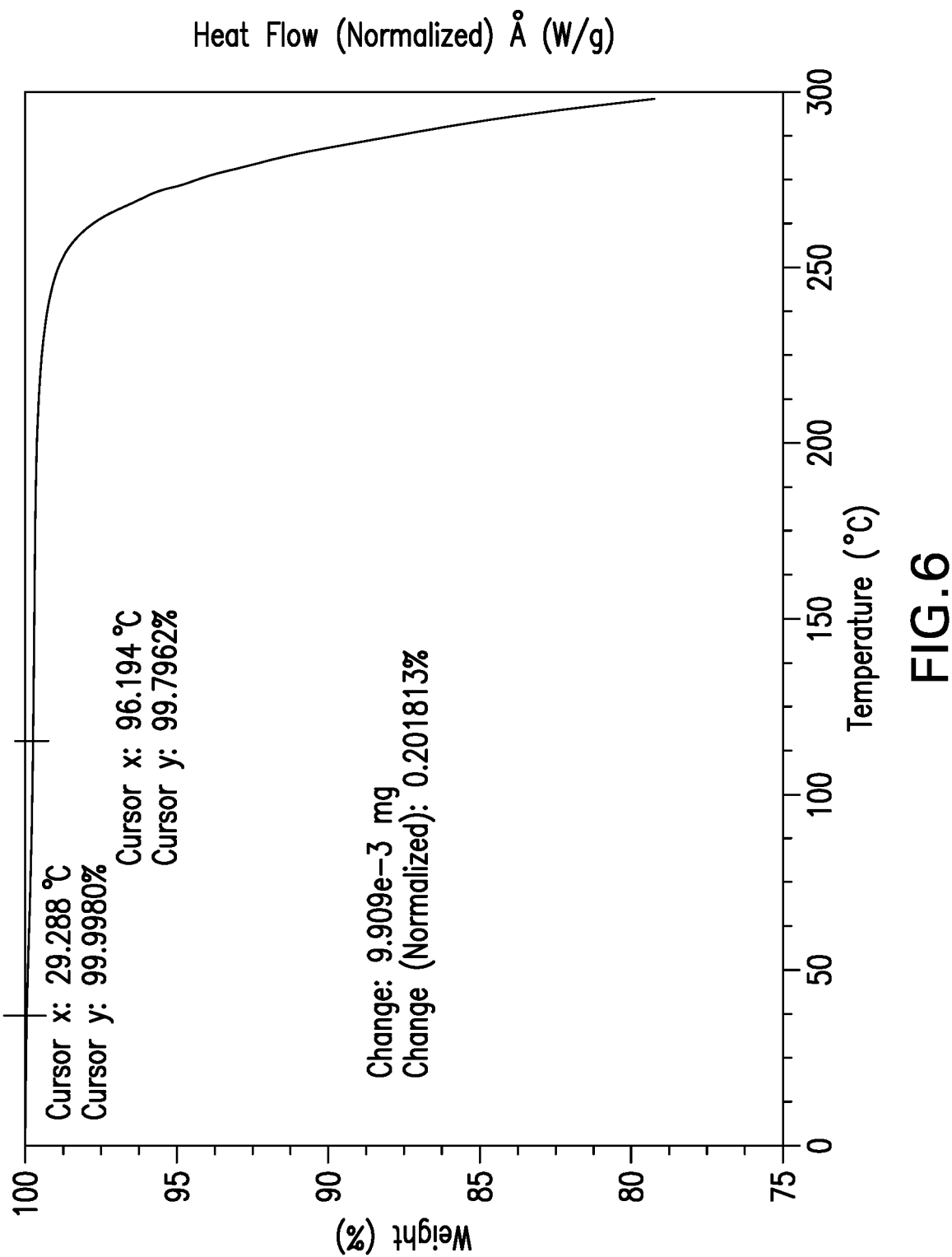
FIG. 6 provides the thermogravimetric analysis thermogram of LACE tosylate Form A.
Figure 7:
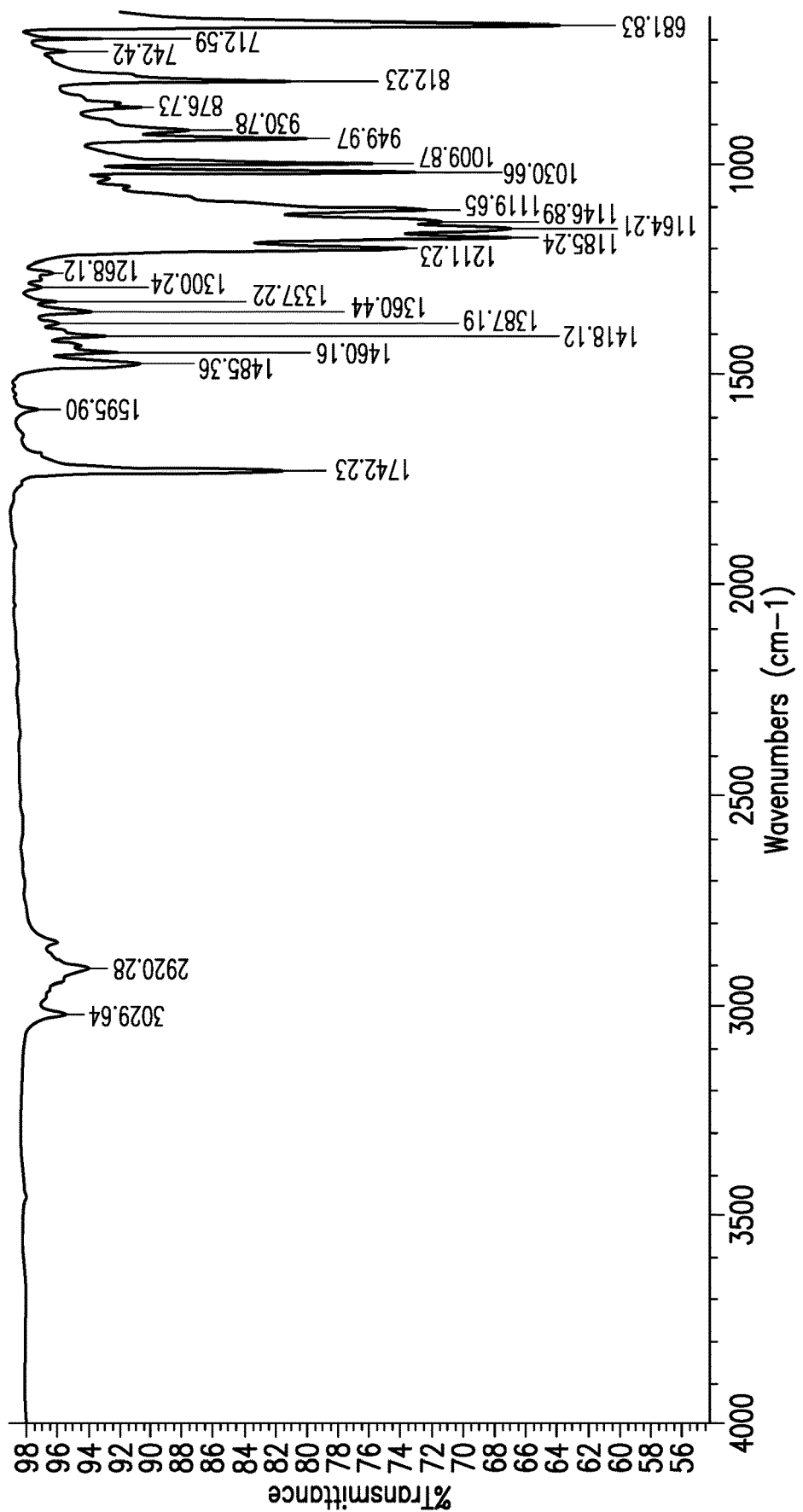
FIG. 7 provides the Fourier transform infrared (FTIR) spectrum of LACE tosylate Form A.

In some embodiments, the present invention provides a crystal form A of lipoic acid choline ester (LACE) tosylate characterized by an X ray diffraction pattern having three or more peaks at 2θ values selected from 21.9, 24.9, 25.9, 26.7, 27.1, 30.4, and 32.1±0.2° 2θ. In some embodiments, the present invention provides a crystal form A of LACE tosylate, characterized by an X ray diffraction pattern having three, four, five, six, seven or more peaks at 2θ values selected from 11.4, 15.2, 18.4, 19.0, 19.4, 19.8, 21.9, 22.9, 24.9, 25.9, 26.7, 27.1, 29.6, 30.4, 32.1±0.2° 2θ. In some embodiments, the present invention provides a crystal form A of LACE tosylate having a X-ray diffraction pattern substantially the same as the X-ray diffraction pattern shown in FIG. 4. In some embodiments, the crystal form A of LACE tosylate has a FTIR spectrum substantially the same as shown in FIG. 7.

Figure 8:
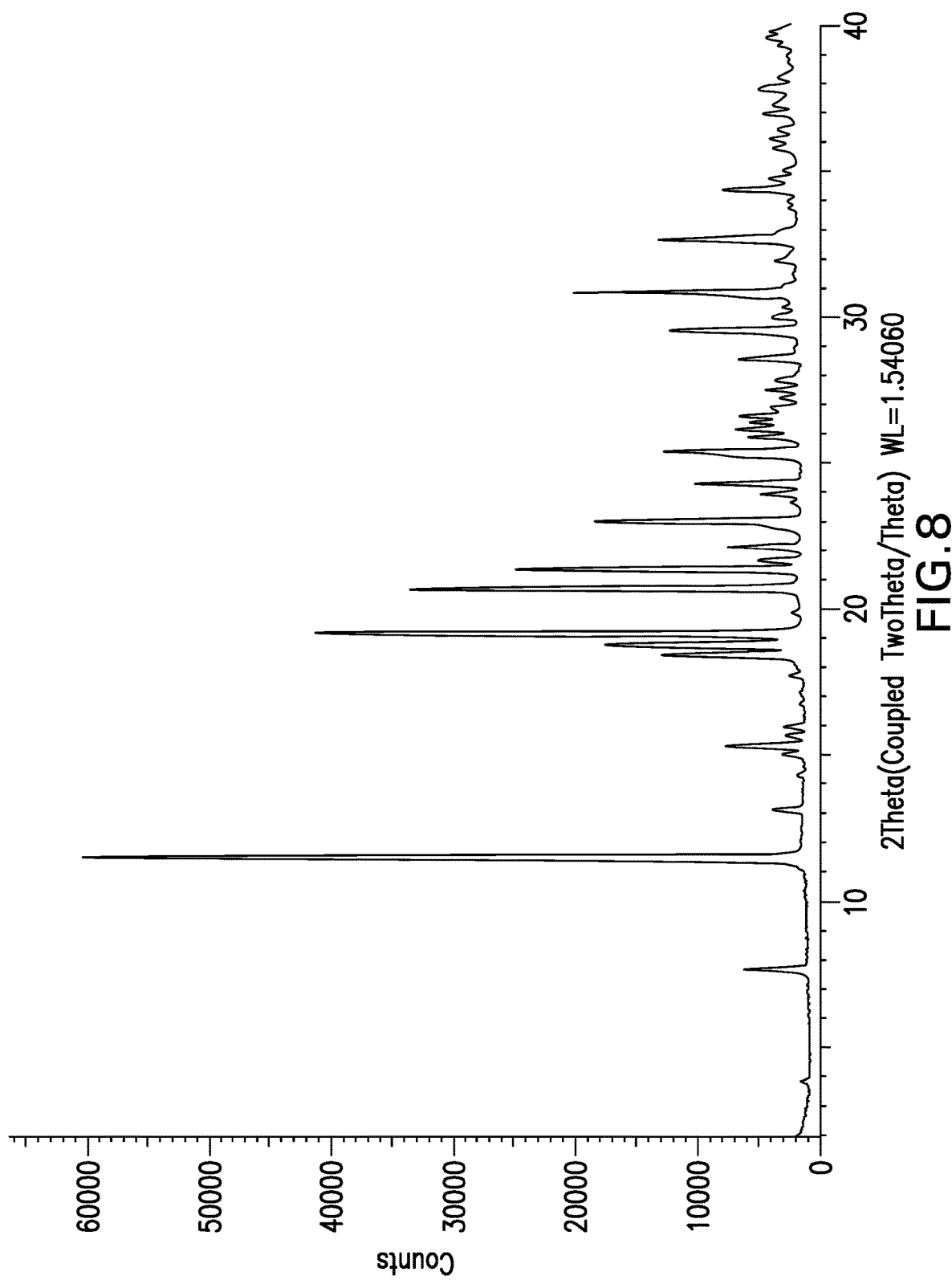
FIG. 8 provides the x-ray diffraction pattern for lipoic acid choline ester tosylate Form B.
Figure 9:
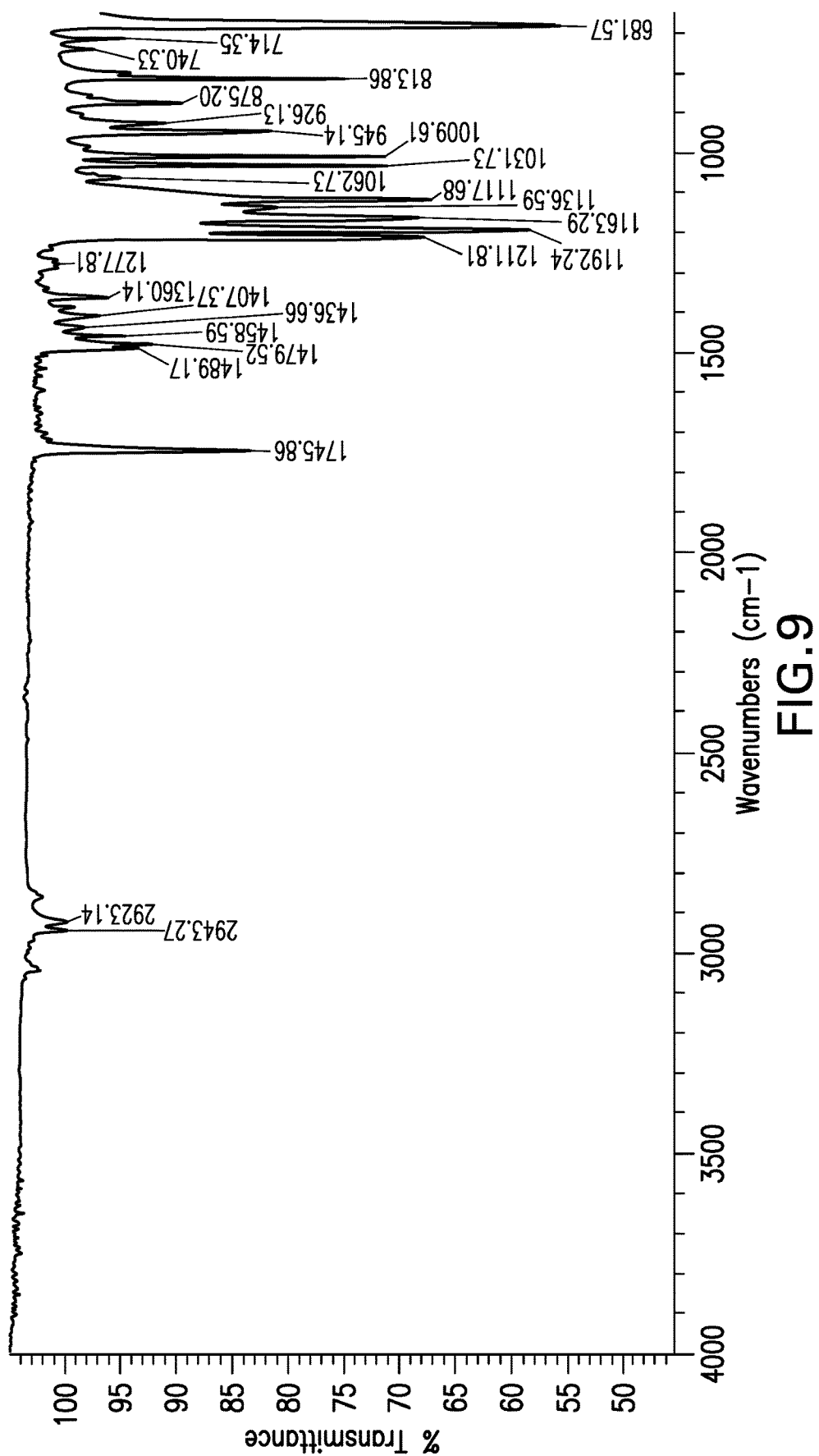
FIG. 9 provides the Fourier transform infrared (FTIR) spectrum of LACE tosylate Form B FIG. 10 provides the differential scanning calorimetry thermogram of LACE tosylate Form B.
Figure 10:
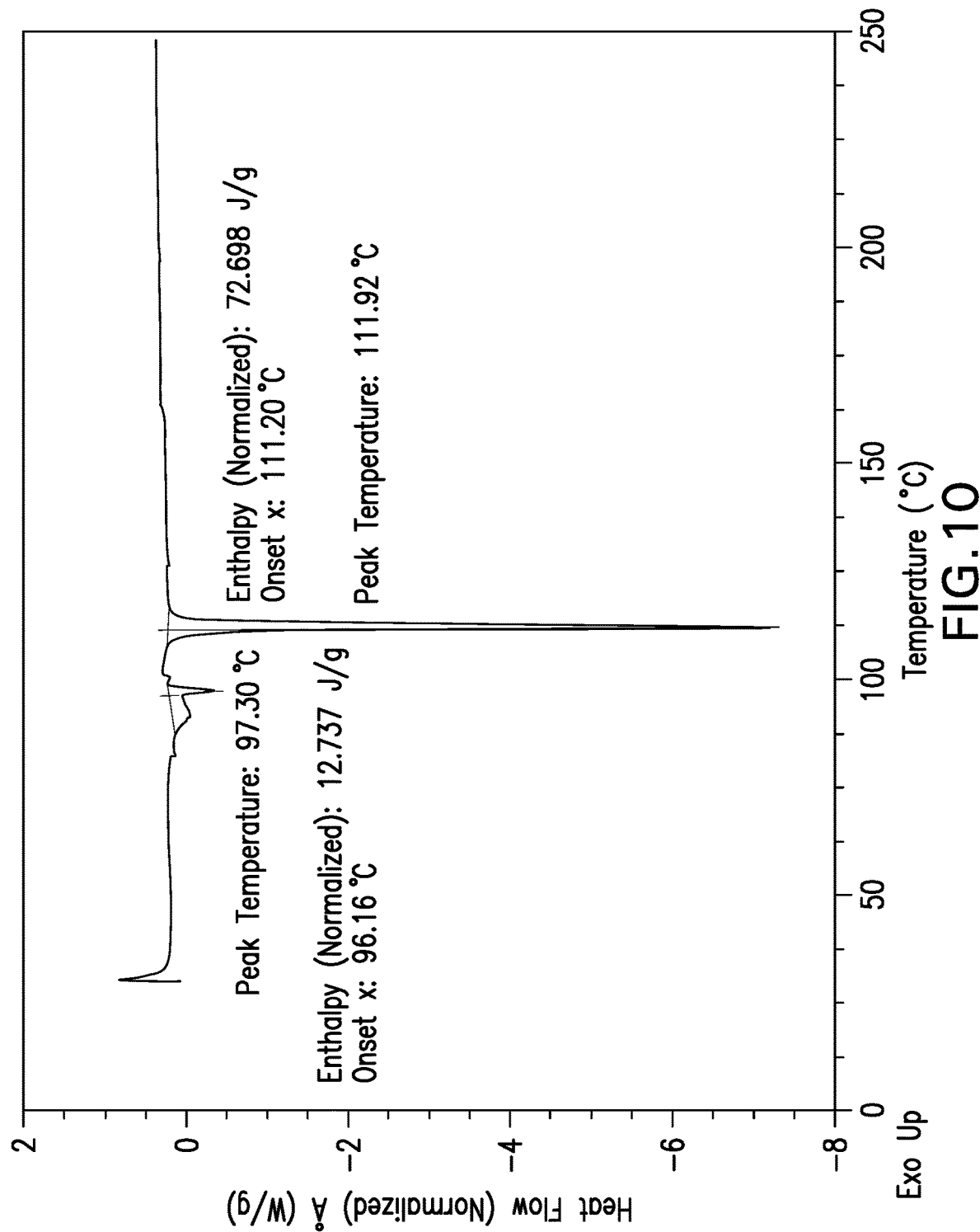
Figure 11:
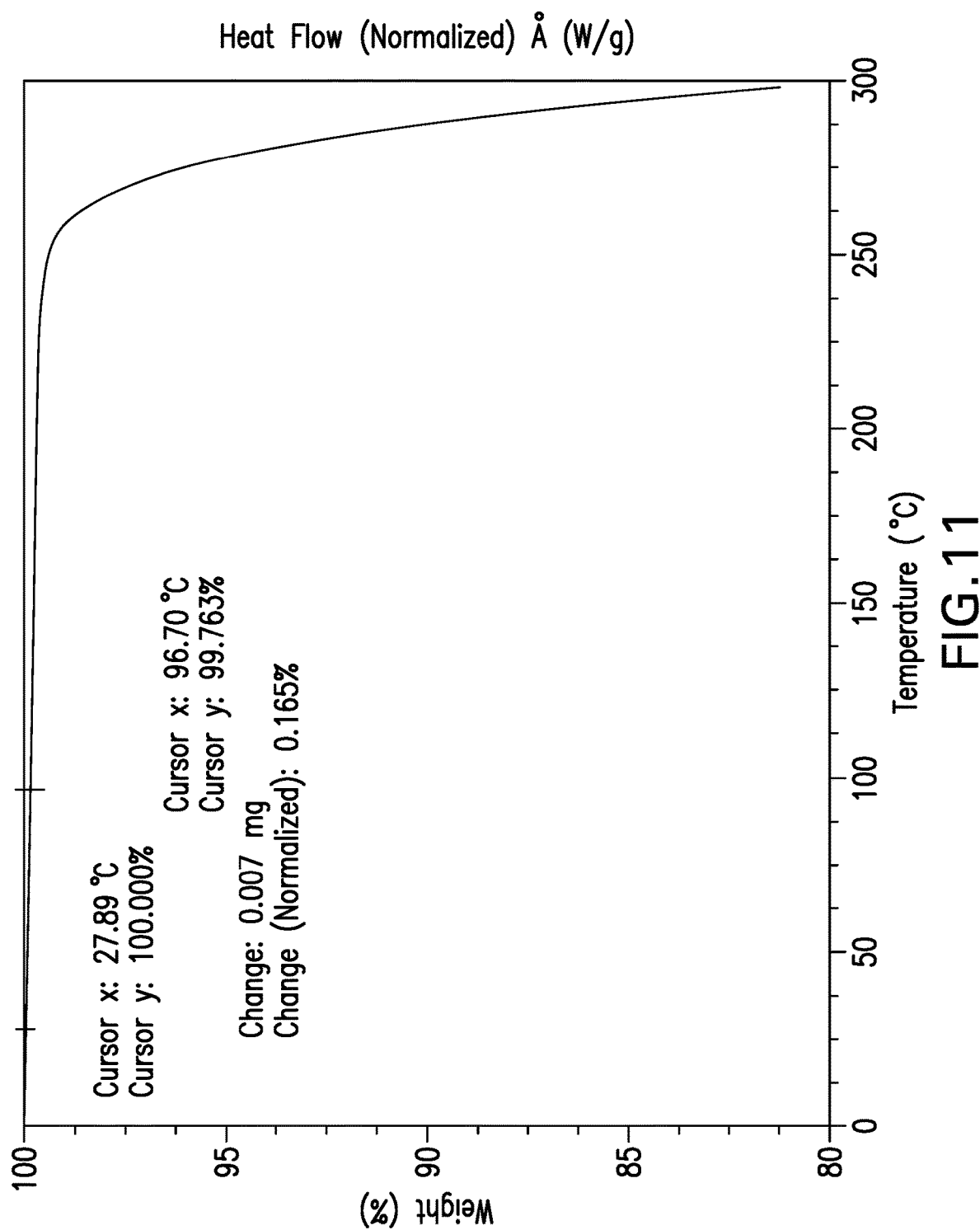
FIG. 11 provides the thermogravimetric analysis thermogram of LACE tosylate Form B.
Figure 12:
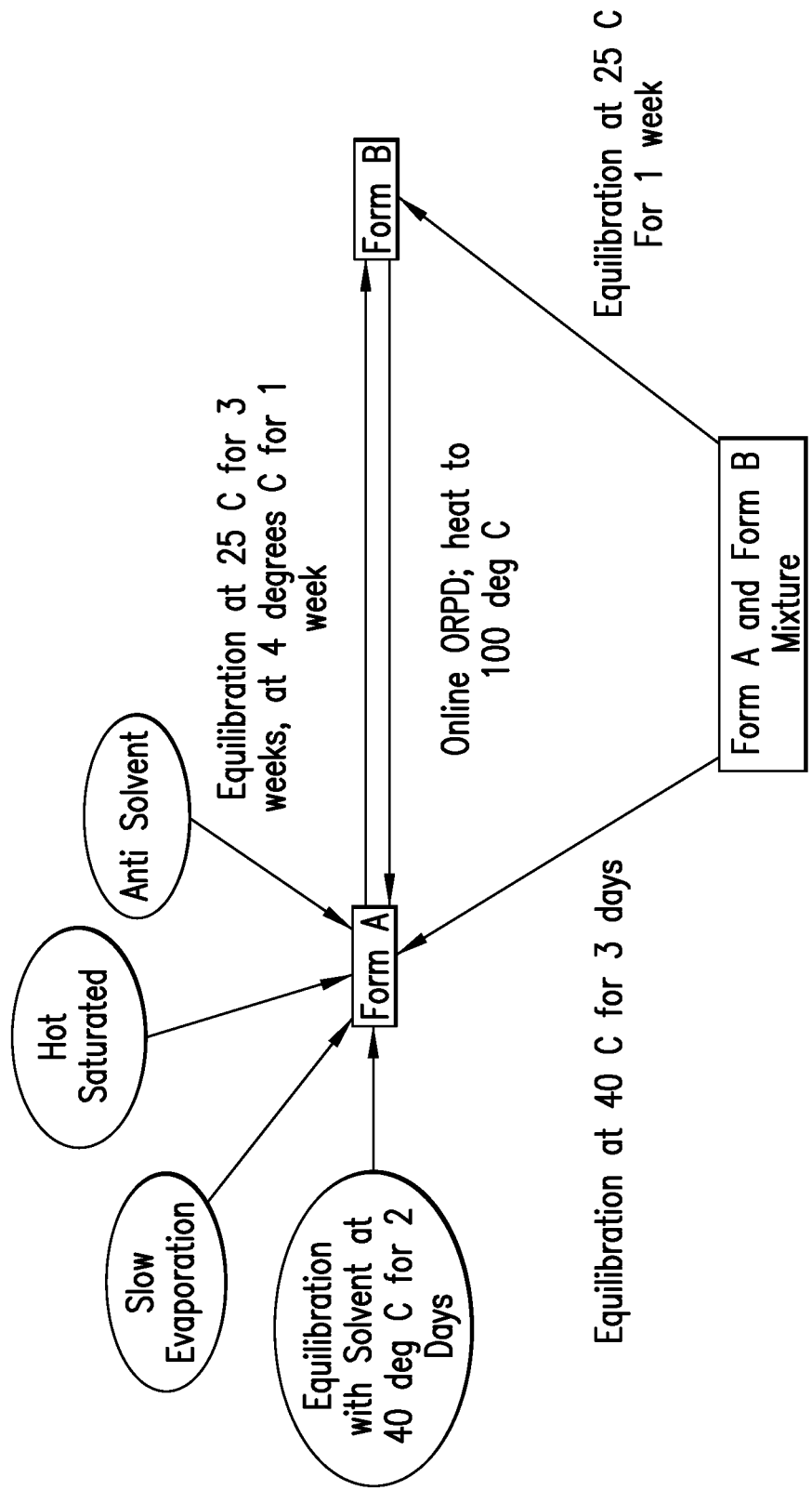
FIG. 12 provides the relationship between the two polymorphic forms of lipoic acid choline tosylate under different conditions and in variable temperature XRPD analysis.

In some embodiments, the present invention provides a crystal form B of lipoic acid choline ester (LACE) tosylate characterized by an X ray diffraction pattern having three or more peaks at 2θ values selected from 7.7, 20.7, 21.4, 24.3, and 25.37±0.2° 2θ. In some embodiments, the present invention provides a crystal form B of LACE tosylate, characterized by an X ray diffraction pattern having four or five peaks at 2θ values selected from 7.7, 20.7, 21.4, 24.3, and 25.37±0.2° 2θ. In some embodiments, the present invention provides a crystal form B of lipoic acid choline ester (LACE) tosylate characterized by an X ray diffraction pattern having three, four, five, six, seven or more peaks at 2θ values selected from 7.7, 11.5, 15.4, 18.5, 18.8, 19.2, 20.7, 21.4, 23.0, 24.3, 25.4, 29.6, 30.9, 32.7. In some embodiments, the present invention provides a crystal form B of LACE tosylate having a X-ray diffraction pattern substantially the same as the X-ray diffraction pattern shown in FIG. 8. In some embodiments, the crystal form B of LACE tosylate has a FTIR spectrum substantially the same as shown in FIG. 9.

In some embodiments, the present invention provides a crystal form of lipoic acid choline ester besylate characterized by an X ray diffraction pattern having three, four, five, six, seven or more peaks at 2θ values selected from 4.3, 12.7, 18.4, 19.0, 19.9, 20.6, 20.8, 21.3, 23.3, 24.2, 25.5, 27.6, 31.4, 33.2, 35.0, 35.4±0.2° 2θ. In some embodiments, LACE besylate has an X-ray diffraction pattern substantially the same as the X-ray powder diffraction pattern shown in FIG. 1.

Figure 14:
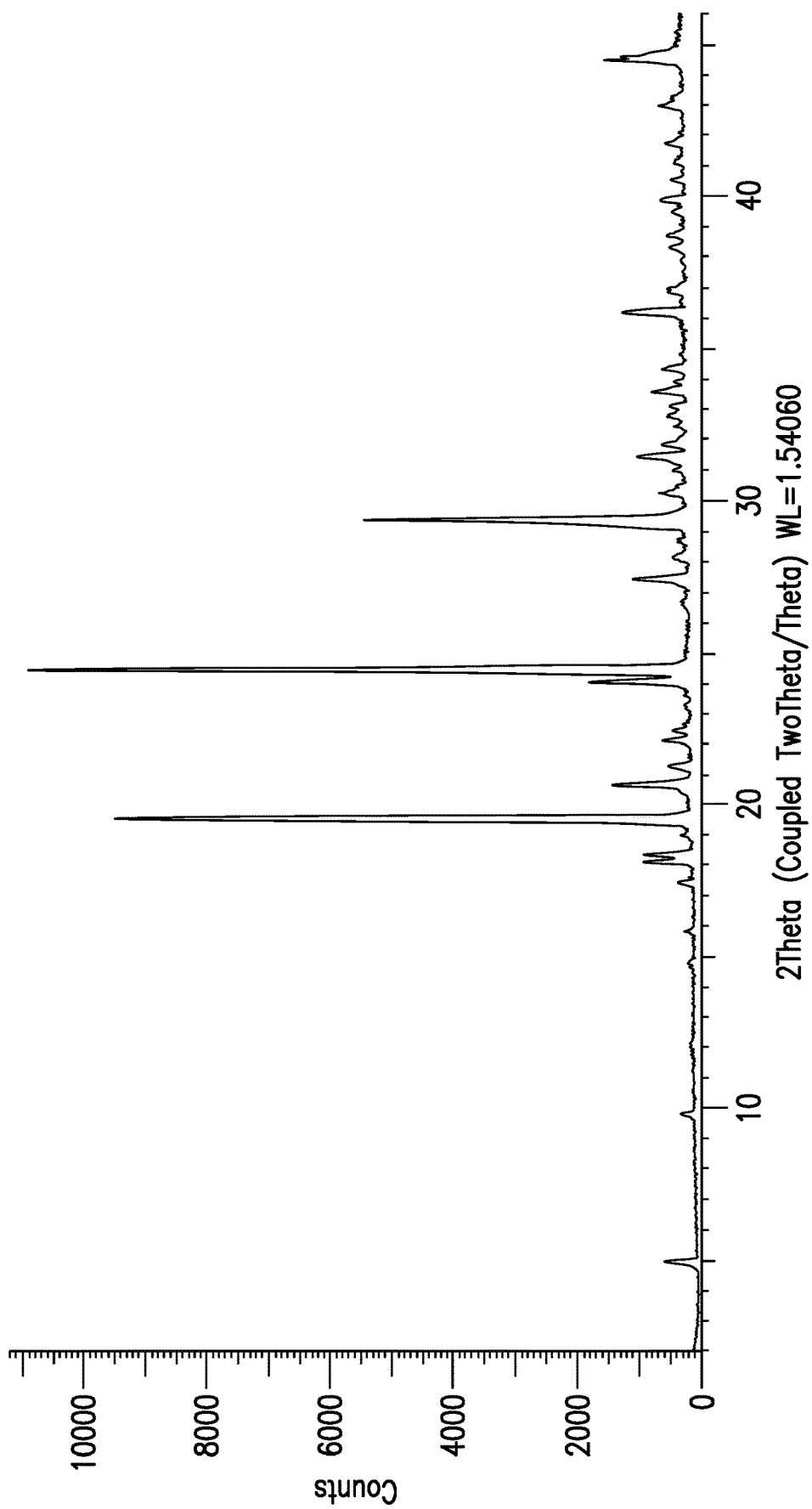
FIG. 14 provides the x-ray diffraction pattern for a crystalline form of lipoic acid choline ester iodide.

In some embodiments, the present invention provides a crystal form of lipoic acid choline ester iodide characterized by an X ray diffraction pattern having three, four, five, six, seven or more peaks at 2θ values selected from 4.9, 18.3, 19.5, 20.6, 22.1, 24.0, 24.4, 27.4, 29.4, 30.2, 31.5, 31.9, 33.6, 34.4, 36.2±0.2°2θ. In some embodiments, LACE iodide has an X-ray diffraction pattern substantially the same as the X-ray powder diffraction pattern shown in FIG. 14.

Figure 13:
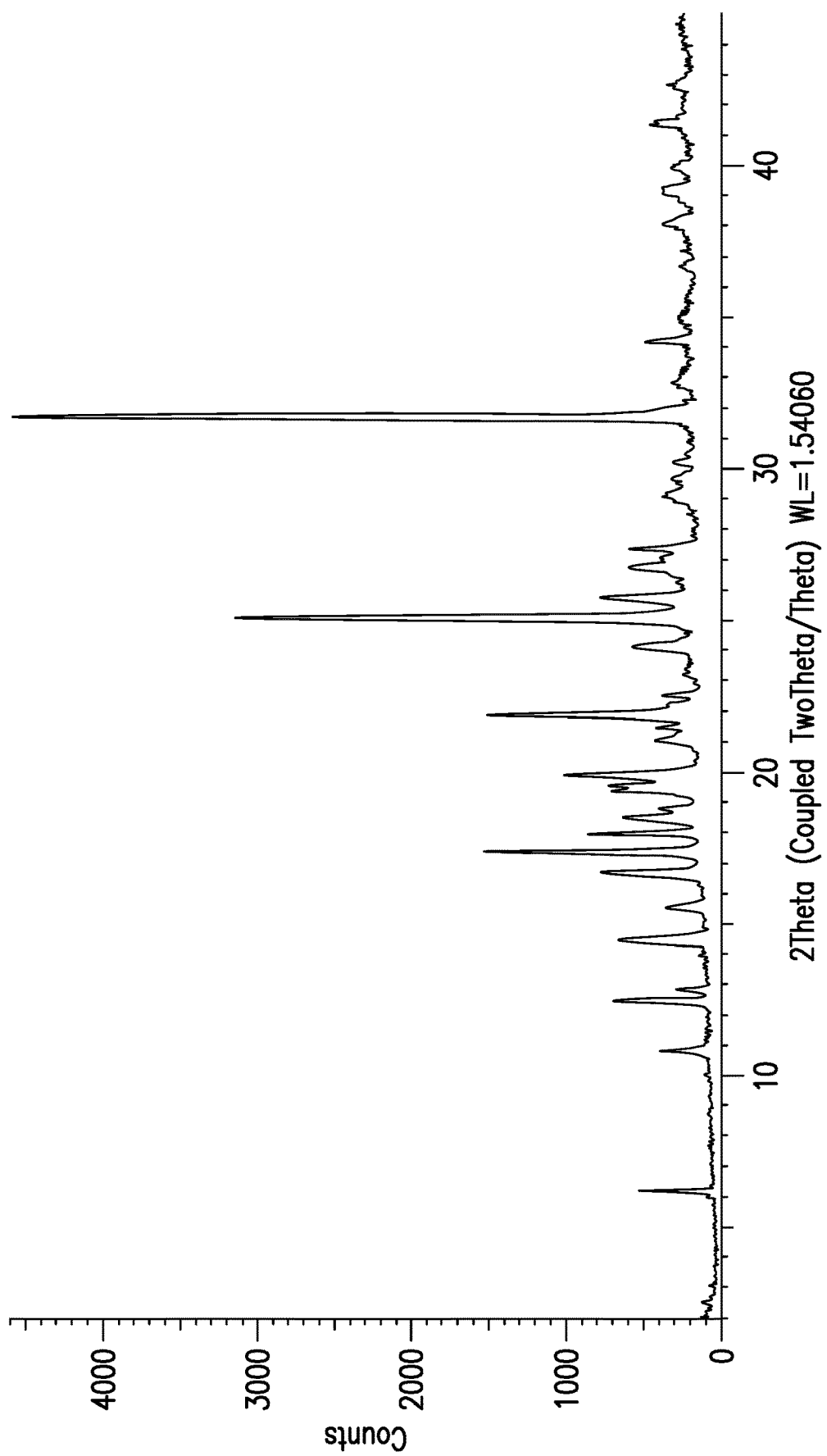
FIG. 13 provides the x-ray diffraction pattern for a crystalline form of lipoic acid choline ester 3,4-dihydroxybenzoate.

In some embodiments, the present invention provides a crystal form of lipoic acid choline ester 3,4-dihydroxy benzoate characterized by an X ray diffraction pattern having three, four, five, six, seven or more peaks at 2θ values selected from 6.2, 10.8, 12.5, 14.5, 15.5, 16.7, 17.4, 18.0, 18.6, 19.6, 19.9, 21.9, 24.2, 25.1, 25.8, 26.8, 27.4, 31.7±0.2° 2θ. In some embodiments, LACE 3,4-dihydroxy benzoate has an X-ray diffraction pattern substantially the same as the X-ray powder diffraction pattern shown in FIG. 13.

Methods of Making Solid Forms of LACE

In some embodiments, the present invention provides a method of preparing a crystal form A of LACE tosylate, comprising adding an anti-solvent to a solution of LACE tosylate, to crystallize LACE as crystal form A. In some embodiments, the solution of LACE tosylate is at about 25° C. In some embodiments, the present invention provides LACE tosylate crystal form A, made by adding an anti-solvent to a solution of LACE tosylate, to crystallize LACE as crystal form A.

In some embodiments, the present invention provides a method of preparing a crystal form B of LACE tosylate, comprising cooling a solution or suspension of LACE tosylate to lower than 10° C., to crystallize LACE as crystal form B. In some embodiments, the method includes cooling a solution or suspension of LACE tosylate to lower than 4° C., to crystallize LACE tosylate as crystal form B. In some embodiments, the present invention provides LACE tosylate crystal form B, made by cooling a solution or suspension of LACE tosylate to lower than 10° C., or lower than 4° C.

In some embodiments, the present invention provides a method of preparing a LACE salt, comprising reacting LACE chloride with an alkali metal salt of an acid. In some embodiments, the present invention provides a LACE salt, made by reacting LACE chloride with an alkali metal salt of an acid. In some embodiments, the alkali metal salt is a sodium or potassium salt. In some embodiments, the acid is an organic acid such as benzenesulfonic acid, toluenesulfonic acid, or 3,4-dihydroxybenzoic acid. In particular embodiments, the present invention provides a method of preparing LACE tosylate, LACE besylate, or LACE 3,4-dihydroxybenzoate, comprising reacting LACE chloride with sodium benzenesulfonate (besylate), sodium toluenesulfonate (tosylate), or sodium 3,4-dihydroxybenzoate, to provide LACE tosylate, LACE besylate, or LACE 3,4-dihydroxybenzoate, respectively. In some embodiments, the reaction is carried out in a suitable solvent. In particular embodiments, the solvent is selected from acetone, acetonitrile, ethanol, or methanol. In particular embodiments, the reaction is performed at temperatures of 0° C. to about 30° C., more particularly, about room temperature, or about 20° C. to about 25° C.

In particular embodiments, the present invention provides a method of preparing LACE tosylate, comprising reacting LACE chloride with sodium tosylate in a suitable solvent. In some embodiments, the present invention provides LACE tosylate, made by reacting LACE chloride with sodium tosylate in a suitable solvent. In particular embodiments, the reaction is carried out in an anhydrous solvent, such as anhydrous acetone, anhydrous methanol, or anhydrous acetonitrile. In particular embodiments, the solvent is anhydrous acetone and the reaction is maintained at 25° C. for at least 24 hours, or at least 2, 3, 4, or 5 days.

In some embodiments, LACE tosylate is prepared as shown in the scheme below. In particular embodiments, the present disclosure provides LACE tosylate made by the process shown below.

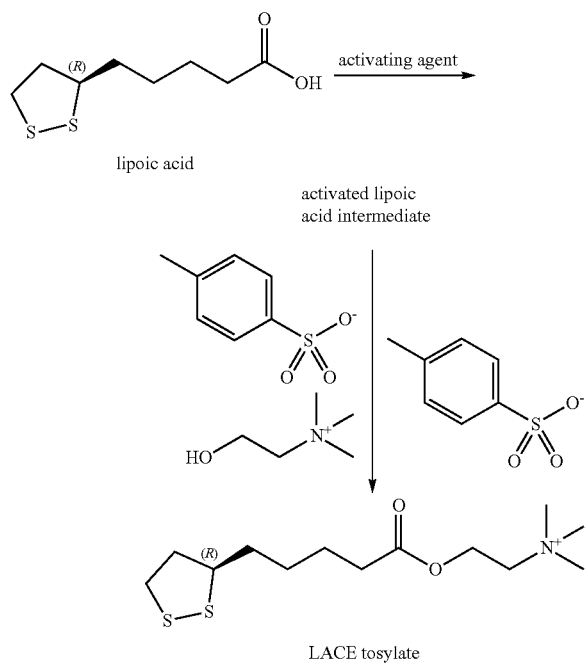

In some embodiments, LACE tosylate is prepared by a process of:
reacting lipoic acid with an activating agent to yield an activated lipoic acid intermediate, and
reacting the activated lipoic acid intermediate with choline tosylate to yield LACE tosylate.

In some embodiments, the activated lipoic acid intermediate is isolated prior to reaction with choline tosylate. In other embodiments, the activated lipoic acid intermediate is not isolated prior to reaction with choline tosylate.

In some embodiments, the reaction of lipoic acid with an activating agent is carried out in a suitable solvent. In particular embodiments, the solvent is tetrahydrofuran or 2-methyltetrahydrofuran. In some embodiments, the reaction of lipoic acid with an activating agent is carried out at temperatures below 25° C., or below 10° C. In particular embodiments the reaction of lipoic acid with an activating agent is carried out at temperatures below 0° C., or for a period of about 5 hours, about 4 hours, about 3 hours, about 2 hours, or about 1 hour. In some embodiments, the ratio of lipoic acid to activating agent is about 1:0.8—about 1:1.3, or about 1:1.2. In particular embodiments, the activating agent is a carbodiimide such as N,N'-dicyclohexylcarbodiimide, ethyl(dimethylaminopropyl) carbodiimide or N,N'-diisopropylcarbodiimide. In some embodiments, the activating agent is carbonyldiimidazole. In some embodiments, the reaction of lipoic acid with an activating agent is carried out in the presence of a base. In particular embodiments, the base is a non-nucleophilic base. In some embodiments, the base is, for example, dimethylaminopyridine, 1,8-diazabicycloundec-7-ene, 1,5-diazabicyclo(4.3.0)non-5-ene, 2,6-di-tert-butylpyridine, or N,N-diisopropylethylamine. In particular embodiments, the base is N,N-diisopropylethylamine. In particular embodiments, the lipoic acid is reacted with carbonyldiimidazole in 2-methyltetrahydrofuran, in the presence of N,N-diisopropylethylamine at temperatures of below 25° C. for about 2-3 hours to yield lipoic acid imidazole intermediate. In particular embodiments, the lipoic acid imidazole intermediate is precipitated from the reaction by addition of an antisolvent, optionally with cooling to below 0° C. In particular embodiments, the antisolvent is tert-butyl methyl ether. In particular embodiments, the lipoic acid imidazole intermediate is isolated from the reaction by a suitable method such as centrifugation or filtration.

In some embodiments, the activated lipoic acid intermediate is reacted with choline tosylate in a suitable solvent, optionally in the presence of a base to yield LACE tosylate. In some embodiments, the solvent is 2-butanone, acetone, acetonitrile, 2-methyltetrahydrofuran, tetrahydrofuran, or mixtures thereof. In some embodiments, the reaction of activated lipoic acid intermediate with choline tosylate is carried out at temperatures below 25° C., or below 30° C., or for about 12 hours, about 1 day, about 2 days, or up to 5 days. In some embodiments, the ratio of activated lipoic acid intermediate to choline tosylate is about 1:0.8—about 1:1.3, or about 1:1. In particular embodiments, the activated lipoic acid intermediate is lipoic acid imidazole intermediate and the solvent for reaction with choline tosylate is acetone, acetonitrile, or a mixture thereof. In some embodiments, the LACE tosylate is precipitated from the reaction by addition of an antisolvent. In particular embodiments, the antisolvent is tert-butyl methyl ether. In particular embodiments, the LACE tosylate is isolated from the reaction by a suitable method such as centrifugation or filtration.

In some embodiments, the LACE tosylate is further treated with activated charcoal in a suitable solvent. In some embodiments, the LACE tosylate is dissolved in the solvent. In some embodiments, the solvent is 2-butanone, acetone, acetonitrile, water, or mixtures thereof. In particular embodiments, during the treatment with activated charcoal the temperature is maintained below 30° C. In some embodiments, the time for treatment with activated charcoal is up to 5 hours, about 1-3 hours, about 1 hour, about 2 hours, about 3 hours, about 4 hours, or about 5 hours. In some embodiments, the activated charcoal is separated from the mixture by suitable method such as filtration or centrifugation.

In some embodiments, the present disclosure provides a method of preparing a crystalline form B of LACE tosylate by dissolving LACE tosylate in a first solvent and adding a second solvent to crystallize LACE tosylate form B from the solution. Optionally, the mixture of LACE tosylate, first solvent, and second solvent is cooled to temperatures below 10° C., or below 0° C. In particular embodiments, the first solvent is acetonitrile, ethanol, water, or mixtures thereof. In particular embodiments, the second solvent is acetone, 2-butanone, methyl tert-butyl ketone, tetrahydrofuran, or mixtures thereof. In particular embodiments, the first solvent is a mixture of 2-butanone and water, and the second solvent is 2-butanone. In other particular embodiments, the first solvent is acetonitrile and the second solvent is acetone.

In some embodiments, the present disclosure provides LACE tosylate having less than about 10%, less than about 9%, less than about 8%, less than about 7%, less than about 6%, less than about 5%, less than about 4%, less than about 3%, less than about 2%, less than about 1%, or less than about 0.5% of associative species of LACE.

In some embodiments, the present disclosure provides LACE tosylate having less than about 1%, less than about 0.9%, less than about 0.8%, less than about 0.7%, less than about 0.6%, less than about 0.5%, less than about 0.4%, less than about 0.3%, less than about 0.2%, less than about 0.1%, less than about 0.05%, less than about 0.02%, of genotoxic impurities. In particular embodiments, the genotoxic impurity is methyl tosylate.

In particular embodiments, the present invention provides a method of preparing LACE besylate, comprising reacting LACE chloride with sodium besylate in a suitable solvent. In particular embodiments, the reaction is carried out in an anhydrous solvent, such as anhydrous acetone, anhydrous methanol, or anhydrous acetonitrile. In particular embodiments, the solvent is anhydrous acetonitrile and the reaction is maintained at 25° C. for up to 24 hours.

In particular embodiments, the present invention provides a method of preparing LACE 3,4-dihydroxybenzoate, comprising reacting LACE chloride with sodium 3,4-dihydroxybenzoate in a suitable solvent. In particular embodiments, the reaction is carried out in an anhydrous solvent, such as anhydrous acetone, anhydrous methanol, or anhydrous acetonitrile. In particular embodiments, the solvent is anhydrous methanol and the reaction is maintained at 25° C. for at least 24 hours, or at least 2, 3, 4, or 5 days. In yet particular embodiments, the sodium 3,4-dihydroxybenzoate is generated in situ by the reaction of 3,4-dihydroxybenzoic acid and the sodium salt of an organic acid such as 2-ethylhexanoic acid.

Pharmaceutical Compositions of LACE Salts

In some embodiments, provided herein are pharmaceutical compositions of lipoic acid choline ester salts. In particular embodiments, the lipoic acid choline ester salt is lipoic acid choline ester tosylate, lipoic acid choline ester besylate, lipoic acid choline ester iodide, or lipoic acid choline ester chloride. In particular embodiments, provided herein are pharmaceutical compositions of lipoic acid choline ester tosylate.

In some embodiments, the concentration of the lipoic ester salt in the pharmaceutical composition is about 0, % w/v to 10% w/v, based on the lipoic acid choline ester cation, about 1% w/v to about 5% w/v or about 0.5% w/v, 1% w/V, about 1.1% w/v, about 1.2% w/v, about 1.3% w/v, about 1.4% w/v, about 1.5% w/v about 2.0% w/v, about 2.3% w/v, about 2.5% w/v, about 3.0% w/v, about 3.5% w/v, about 4.0% w/v, about 4.5% w/v, about 5% w/v, about 6% w/v, about 7% w/v, about 8% w/v, about 9% w/v, or about 10% w/v. It will be understood that the actual percent amounts of the salt will depend on the salt form used. For example, 2.2% w/v of lipoic acid choline ester tosylate corresponds to 1.3% w/v of lipoic acid choline ester. Unless otherwise indicated, the percentages herein are expressed in units of weight/volume, i.e., % w/v. It will be appreciated that % w/v can alternatively be expressed as mg/ml. Thus, 1.3% w/v corresponds to 13 mg/ml. In particular embodiments, the pharmaceutical composition includes lipoic acid choline ester tosylate at a concentration of about 0.8% w/v, about 2.1% w/v, about 2.2% w/v, about 3.7% w/v, about 4.8% w/v, or about 6.4% w/v, which corresponds to about 0.5% w/v, about 1.3% w/v, about 1.4% w/v, about 2.3% w/v, about 3.0% w/v, and about 4.0% w/v of lipoic acid choline ester cation.

In some embodiments, the pharmaceutical composition includes a cyclodextrin. In some embodiments, the cyclodextrin is hydroxypropyl β-cyclodextrin (HPBCD). In particular embodiments, the cyclodextrin is present in an amount of about 1% w/v to about 30% w/v, or about 2.5% w/v, about 5% w/v, about 6% w/v, about 10% w/v, about 15% w/v, about 19% w/v, about 20% w/v, about 25% w/v, or about 30% w/v. In particular embodiments, the pharmaceutical composition includes HPBCD in an amount about 1 to about 2 molar equivalents, or about 1 to about 1.5 molar equivalents to the lipoic acid choline ester. In particular embodiments, the pharmaceutical composition includes about 1.5% w/v, 2.5% w/v, 6.5% w/v, about 15% w/v, or about 19.6% w/v of HPBCD. In some embodiments, the pharmaceutical composition comprises about 1.5% w/v, about 2.5% w/v, about 3.3% w/v, about 6.7% w/v, about 11.5% w/v, about 15.0% w/v, or about 19.6% w/v of HPBCD.

In some embodiments, the pharmaceutical composition includes a viscosity modifying agent. In some embodiments, the viscosity modifying agent is carbopol gels, cellulosic agents (e.g., hydroxypropyl methylcellulose, hydroxyethyl cellulose), polycarbophil, polyvinyl alcohol, dextran, gelatin, glycerin, polyethylene glycol, poloxamer 407, polyvinyl alcohol and polyvinyl pyrrolidone or mixtures thereof. Suitable amount of viscosity modifying agent can be in the range of 0.1% w/v to 20% w/v, or about 0.1% w/v, about 0.2% w/v, about 0.3% w/v, about 0.4% w/v, about 0.5% w/v, about 1% w/v, about 2% w/v, about 3% w/v, about 4% w/v, about 5% w/v, about 8% w/v, about 10% w/v, about 12% w/v, about 14% w/v, about 16% w/v, about 18% w/v, or about 20% w/v. In particular embodiments, the viscosity modifying agent is a cellulosic agent that is hydroxypropyl methyl cellulose (HPMC) or hydroxyethyl cellulose or mixtures thereof, in an amount of from 0.1% w/v to about 1% w/v, or about 0.5% w/v. In particular embodiments, the viscosity modifying agent is HPMC. In other embodiments, the viscosity modifying agent is polyethylene glycol in an amount of about 2% w/v, about 3% w/v, about 4% w/v, about 5% w/v, about 6% w/v, about 7% w/v, about 8% w/v, or about 9% w/v, or about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In particular embodiments, the polyethylene glycol is PEG300 or PEG400. In particular embodiments, the viscosity modifying agent is substantially all HPMC or substantially all PEG 300.

In some embodiments, the pharmaceutical compositions described herein have a viscosity of at least 1 cP, at least 5 cP, at least 10 cP, at least 20 cP to at most about 200 cP.

In some embodiments, the pharmaceutical composition includes a buffer. Suitable buffers can be any of those known in the art that can achieve a desired pH (e.g., described herein) for the formulation. Non-limiting examples include phosphate buffers (e.g., sodium phosphate monobasic monohydrate, sodium phosphate dibasic anhydrous), acetate buffer, citrate buffer, borate buffers, and HBSS (Hank's Balanced Salt Solution). Suitable amounts of a buffer agent can be readily calculated based on a desired pH. In particular embodiments, the buffer is an acetate buffer. However, in some embodiments, the pharmaceutical composition does not include a buffer agent. In some embodiments, the pH of the aqueous solution or the final pharmaceutical composition is adjusted with an acid (e.g., hydrochloride acid) or a base (e.g., sodium hydroxide) to the desired pH range (e.g., as described herein).

In some embodiments, the pharmaceutical composition has a pH of 4 to 8. In some embodiments, the pharmaceutical composition has a pH of about 4 to about 5, about 4 to about 6, about 4.2 to about 4.8, about 4.3 to about 4.7, or about 4.25 to about 4.75. In particular embodiments, the pharmaceutical composition has a pH of about 4.5. In some embodiments, the pH of the aqueous solution or the final pharmaceutical composition is adjusted with an acid (e.g., hydrochloric acid) or a base (e.g., sodium hydroxide) to the desired pH range (e.g., as described herein).

In some embodiments, the pharmaceutical composition includes a tonicity agent. Suitable tonicity agents can be any of those known in the art and may include ionic or nonionic tonicity agents. Non-limiting examples of ionic tonicity agents include sodium chloride, potassium chloride, and other salts that are pharmaceutically acceptable, and mixtures thereof. Non limiting examples of nonionic tonicity agents include mannitol, dextrose, glycerin, propylene glycol, polyethylene glycol, and mixtures thereof. In particular embodiments, the tonicity agent is an ionic tonicity agent present in an amount of up to 150 mM, or about 5 to about 150 mM, about 50 to about 150 mM, about 100 to about 150 mM, or about 50 to about 100 mM, or a nonionic tonicity agent present in an amount of up to 100 mM, up to 150 mM, up to 200 mM, up to 250 mM, or up to 300 mM. In some embodiments, the tonicity agent is sodium chloride or potassium chloride in an amount of from about 0.01% w/v to about 1% w/v, or about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v. A person of ordinary skill in the art will appreciate that the concentrations in % w/v can also be expressed in mM. In particular embodiments, the tonicity agent is sodium chloride. In specific embodiments, the sodium chloride is present in an amount from about 0.01% w/v to about 1% w/v, about 0.1% w/v to about 0.5% w/v, or about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v. In specific embodiments, the sodium chloride is present in an amount of about 0.1% w/v, about 0.2% w/v, or about 0.5% w/v. In specific embodiments, the sodium chloride is present in an amount of about 0.25% w/v, about 0.5% w/v, or about 0.6% w/v. In specific embodiments, the sodium chloride is present in an amount of about 0.1% w/v, about 0.28% w/v, or about 0.53% w/v.

In some embodiments, the pharmaceutical compositions described herein have an osmolality of about 200 to about 450 milliosmoles per kilogram (mOsm/kg). In particular embodiments, the pharmaceutical compositions described herein are isotonic, or have an osmolality of about 250 to about 425 mOsm/kg, or about 250 to about 330 mOsm/kg, or about 260 to about 300 mOsm/kg.

In some embodiments, the pharmaceutical composition includes a preservative. Suitable preservatives can be any of those known in the art. Non-limiting examples include benzalkonium chloride (BAC), sorbic acid, boric acid, cetrimonium, chlorobutanol, edetate disodium (EDTA), polyquaternium-1 (Polyquad®), polyhexamethylene biguanide (PHMB), stabilized oxychloro complex (PURITE®), sodium perborate, SofZia®, or combinations thereof. Suitable amount of a preservative in the pharmaceutical composition can be in an amount of about 0.005% w/v to 0.1% w/v, about 0.005% w/v, about 0.01% w/v, about 0.02% w/v, about 0.05% w/v, or about 0.1% w/v. In some embodiments, the preservative is benzalkonium chloride. In some embodiments, the benzalkonium chloride is in the amount of about 0.003% w/v to about 0.1% w/v, or 0.003% w/v, 0.01% w/v, 0.02% w/v, 0.05% w/v, 0.1% w/v. In some embodiments, the benzalkonium chloride is in the amount of about 0.01% w/v or 0.02% w/v. In some embodiments, the pharmaceutical composition includes boric acid or sorbic acid in an amount of about 0.1% w/v to about 0.5% w/v, or about 0.1% w/v to about 0.4% w/v, or about 0.1% w/v, about 0.2% w/v, about 0.3% w/v, about 0.4% w/v, or about 0.5% w/v. In some embodiments, the pharmaceutical composition includes a mixture of boric acid and benzalkonium chloride in the amounts described above. In some embodiments, the pharmaceutical composition includes sorbic acid in an amount of about 0.1% w/v, or boric acid in and amount of about 0.3% w/v. In any of the embodiments described herein, the preservative is in an amount that is ophthalmically acceptable. In some embodiments, the pharmaceutical composition is free of a preservative.

In some embodiments, the pharmaceutical compositions disclosed herein may include a surfactant. Suitable surfactants can be any of those known in the art, including ionic surfactants and nonionic surfactants. Non-limiting examples of nonionic surfactants include polyoxyethylene fatty esters (e.g., polysorbate 80 [poly(oxyethylene)sorbitan monooleate], polysorbate 60 [poly(oxyethylene)sorbitan monostearate], polysorbate 40 [poly(oxyethylene)sorbitan monopalmitate], poly(oxyethylene)sorbitan monolaurate, poly(oxyethylene)sorbitan trioleate, or polysorbate 65 [poly (oxyethylene)sorbitan tristearate]), polyoxyethylene hydrogenated castor oils (e.g., polyoxyethylene hydrogenated castor oil 10, polyoxyethylene hydrogenated castor oil 40, polyoxyethylene hydrogenated castor oil 50, or polyoxyethylene hydrogenated castor oil 60), polyoxyethylene polyoxypropylene glycols (e.g., polyoxyethylene (160) polyoxypropylene (30) glycol [Pluronic F681], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Pluronic F1271], or polyoxyethylene (20) polyoxypropylene (20) glycol [Pluronic L-441]), polyoxyl 40 stearate, sucrose fatty esters, and a combination thereof. In some embodiments, the surfactant is polysorbate 80. Suitable amount of surfactant in the pharmaceutical composition can be in the range of about 0.01% w/v to about 5% w/v (e.g., about 0.05% w/v, about 0.1% w/v, about 0.2% w/v, about 0.5% w/v, about 1% w/v, about 2% w/v, about 3% w/v, about 4% w/v, or about 5% w/v, or any ranges based on these specified numeric values). In some embodiments, the surfactant is polysorbate 80, and the amount of polysorbate 80 is in the range of 0.05% to 5% (e.g., 0.05%, 0.1%, 0.2%, 0.5%, 1%, 2%, 3%, 4%, 5%, or any ranges based on these specified numeric values) by weight of the composition. In some embodiments, the amount of polysorbate 80 is 0.5% by weight of the composition. In any of the embodiments described herein, the surfactant is in an amount that is ophthalmically acceptable. In some embodiments, the pharmaceutical composition is free of a surfactant.

In some embodiments, the pharmaceutical composition contains an anti-oxidant. In some embodiments, the anti-oxidant is comprised of ascorbate. In another embodiment, the anti-oxidant contains glutathione. Suitable antioxidant can be any of those known in the art. Non-limiting examples include ascorbic acid, L-ascorbic acid stearate, alphathioglycerin, ethylenediaminetetraacetic acid, erythorbic acid, cysteine hydrochloride, N-acetylcysteine, L-carnitine, citric acid, tocopherol acetate, potassium dichloroisocyanurate, dibutylhydroxytoluene, 2,6-di-t-butyl-4-methylphenol, soybean lecithin, sodium thiosulfate, sodium thioglycollate, sodium thiomalate, natural vitamin E, tocopherol, ascorbyl pasthyminate, sodium pyrosulfite, butylhydroxyanisole, 1,3-butylene glycol, pentaerythtyl tetrakis[3-(3,5-di-t-butyl-4-hydroxyphenyl)]propionate, propyl gallate, 2-mercaptobenzimidazole and oxyquinoline sulfate. Suitable amount of antioxidant can be in the range of about 0.1% to about 5% (e.g., about 0.1%, about 0.5%, about 1%, about 2%, about 3%, about 4%, or about 5%, or any ranges based on these specified numeric values) by weight of the composition. In any of the embodiments described herein, the antioxidant is in an amount that is ophthalmically acceptable. In some embodiments, the pharmaceutical composition does not include an anti-oxidant.

In some embodiments, the pharmaceutical composition contains a biochemical energy source. Suitable biochemically acceptable energy source can be any of those known in the art. For example, the biochemical acceptable energy source can be any of those that can facilitate reduction by participating as an intermediate of energy metabolic pathways, particularly the glucose metabolic pathway. Non-limiting examples of suitable biochemically acceptable energy source include amino acids or derivative thereof (e.g., alanine, glycine, valine, leucine, isoleucine, 2-oxoglutarate, glutamate, and glutamine, etc.), a sugar or metabolites thereof (e.g., glucose, glucose-6-phosphate (G6P)), pyruvate (e.g., ethyl pyruvate), lactose, lactate, or derivatives thereof), a lipid (e.g., a fatty acid or derivatives thereof such as mono-, di-, and tri-glycerides and phospholipids), and others (e.g., NADH). Suitable amount of a biochemically acceptable energy source can be in the range of 0.01% w/v to 5% w/v (e.g., 0.05% w/v, 0.1% w/v, 0.2% w/v, 0.5% w/v, 1% w/v, 2% w/v, 3% w/v, 4% w/v, or 5% w/v). In some embodiments, the biochemical energy source is ethyl pyruvate. In some embodiments, the biochemical energy source is alanine. In some embodiments, the amount of ethyl pyruvate or alanine is in the range of 0.05% w/v to 5% w/v (e.g., 0.05% w/v, 0.1% w/v, 0.2% w/v, 0.5% w/v, 1% w/v, 2% w/v, 3% w/v, 4% w/v, or 5% w/v). In some embodiments, the amount of alanine is 0.5% by weight of the composition. In any of the embodiments described herein, the pharmaceutical compositions described herein do not include a biochemical energy source.

In some embodiments, provided herein are pharmaceutical compositions comprising
  a lipoic acid choline ester salt,
  hydroxypropyl-β-cyclodextrin,
  optionally a tonicity agent,
  optionally a viscosity modifying agent,
  optionally, a buffer, and
  optionally, a preservative.

In some embodiments, the pharmaceutical compositions are aqueous.

In some embodiments, provided herein are pharmaceutical compositions comprising
  about 0.5% w/v to about 5% w/v (based on the lipoic acid choline ester) of a lipoic acid choline ester salt,
  about 2% w/v to about 25% w/v of hydroxypropyl-β-cyclodextrin,
  up to 300 mM of a tonicity agent,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of a lipoic acid choline ester salt,
  about 2% w/v to about 25% w/v of hydroxypropyl-β-cyclodextrin,
  up to 300 mM of a tonicity agent selected from the group consisting of ionic tonicity agents, nonionic tonicity agents, and mixtures thereof,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of lipoic acid choline ester tosylate,
  about 2% w/v to about 25% w/v of hydroxypropyl-β-cyclodextrin,
  up to 150 mM of a ionic tonicity agent or up to 300 mM of a nonionic tonicity agent,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of lipoic acid choline ester iodide,
  about 2% w/v to about 25% w/v of hydroxypropyl-β-cyclodextrin,
  up to 150 mM of a ionic tonicity agent or up to 300 mM of a nonionic tonicity agent,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of lipoic acid choline ester besylate,
  about 2% w/v to about 25% w/v of hydroxypropyl-β-cyclodextrin,
  up to 150 mM of a ionic tonicity agent or up to 300 mM of a nonionic tonicity agent,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of lipoic acid choline ester chloride,
  about 2% w/v to about 25% w/v of hydroxypropyl-β-cyclodextrin,
  up to 150 mM of a ionic tonicity agent or up to 300 mM of a nonionic tonicity agent,
  0% w/v to about 20% w/v of a viscosity modifying agent,
  0% w/v to about 1% w/v of a buffer, and
  0% w/v to about 0.5% w/v of a preservative.

In some embodiments, provided herein are pharmaceutical compositions comprising
  about 0.5% w/v to about 5% w/v (based on the lipoic acid choline ester) of lipoic acid choline ester tosylate,
  about 2% w/v to about 25% w/v of hydroxypropyl-β-cyclodextrin,
  up to 150 mM of a ionic tonicity agent or up to 300 mM of a nonionic tonicity agent,
  0% w/v to about 20% w/v of a viscosity modifying agent,
  0.01% w/v to about 1% w/v of a buffer, and
  0% w/v to about 0.5% w/v of a preservative.

In some embodiments, provided herein are pharmaceutical compositions comprising about 0.5% w/v to about 5% w/v (based on the lipoic acid choline ester) of lipoic acid choline ester tosylate, about 2% w/v to about 25% w/v of hydroxypropyl-β-cyclodextrin, up to 150 mM of a ionic tonicity agent or up to 300 mM of a nonionic tonicity agent, 0.01% w/v to about 20% w/v of a viscosity modifying agent, 0.01% w/v to about 1% w/v of a buffer, and 0% w/v to about 0.5% w/v of a preservative selected from the group consisting of benzalkonium chloride, sorbic acid, boric acid, and mixtures thereof.

In some embodiments, provided herein are pharmaceutical compositions comprising about 0.5% w/v to about 5% w/v (based on the lipoic acid choline ester) of lipoic acid choline ester tosylate, about 2% w/v to about 25% w/v of hydroxypropyl-β-cyclodextrin, up to 150 mM of a ionic tonicity agent or up to 300 mM of a nonionic tonicity agent, 0% w/v to about 20% w/v of a viscosity modifying agent, 0% w/v to about 1% w/v of a buffer, and 0% w/v to about 0.5% w/v of a preservative selected from the group consisting of sorbic acid, boric acid, and mixtures thereof, wherein the pharmaceutical composition does not include a biochemical energy source.

In some embodiments, provided herein are pharmaceutical compositions comprising about 0.5% w/v to about 5% w/v (based on the lipoic acid choline ester) of lipoic acid choline ester tosylate, about 2% w/v to about 25% w/v of hydroxypropyl-β-cyclodextrin, up to 150 mM of a ionic tonicity agent or up to 300 mM of a nonionic tonicity agent, 0% w/v to about 20% w/v of a viscosity modifying agent, 0% w/v to about 1% w/v of a buffer, and 0% w/v to about 0.5% w/v of a preservative, wherein the pharmaceutical composition does not include benzalkonium chloride and does not include a biochemical energy source.

In some embodiments, provided herein are pharmaceutical compositions comprising about 0.5% w/v to about 5% w/v (based on the lipoic acid choline ester) of lipoic acid choline ester tosylate, about 2% w/v to about 25% w/v of hydroxypropyl-β-cyclodextrin, about 1 mM to about 150 mM of a tonicity agent selected from the group consisting of sodium chloride, potassium chloride, and mixtures thereof, or about 1 mM to about 300 mM of a tonicity agent selected from the group consisting of mannitol, dextrose, glycerin, propylene glycol and mixtures thereof, about 0.01% w/v to about 20% w/v of a viscosity modifying agent selected from the group consisting of polyethylene glycols, cellulosic agents, and mixtures thereof, about 0.01% w/v to about 1% w/v of a buffer selected from the group consisting of phosphate buffers (e.g., sodium phosphate monobasic monohydrate, sodium phosphate dibasic anhydrous), acetate buffer, citrate buffer, borate buffers, and HBSS (Hank's Balanced Salt Solution), wherein the pharmaceutical composition has a pH of about 4.3 to about 4.7, and 0% w/v to about 0.5% w/v of a preservative, wherein the pharmaceutical composition does not include benzalkonium chloride and does not include a biochemical energy source, e.g., alanine.

In some embodiments, provided herein are pharmaceutical compositions comprising about 0.5% w/v to about 5% w/v (based on the lipoic acid choline ester) of lipoic acid choline ester tosylate, about 2% w/v to about 25% w/v of hydroxypropyl-β-cyclodextrin, about 1 mM to about 150 mM of a tonicity agent selected from the group consisting of sodium chloride, potassium chloride, and mixtures thereof, or about 1 mM to about 300 mM of a tonicity agent selected from the group consisting of mannitol, dextrose, and mixtures thereof, about 0.01% w/v to about 20% w/v of a viscosity modifying agent selected from the group consisting of polyethylene glycols, cellulosic agents, and mixtures thereof, about 0.01% w/v to about 1% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, and 0% w/v to about 0.5% w/v of a preservative, wherein the pharmaceutical composition does not include benzalkonium chloride and does not include a biochemical energy source, e.g., alanine.

In some embodiments, provided herein are pharmaceutical compositions comprising about 0.5% w/v to about 5% w/v (based on the lipoic acid choline ester) of lipoic acid choline ester tosylate, hydroxypropyl-β-cyclodextrin in an amount equimolar to the lipoic acid choline ester tosylate, about 0.2% w/v to about 1% w/v of a tonicity agent selected from the group consisting of sodium chloride, and potassium chloride, or about 1 mM to about 300 mM of a tonicity agent selected from the group consisting of mannitol, dextrose, and mixtures thereof, about 0.01% w/v to about 1% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include a biochemical energy source, e.g., alanine, and wherein the pharmaceutical composition meets US Pharmacopoeia preservation standards for sterile parenteral multi-dose compositions.

In some embodiments, provided herein are pharmaceutical compositions comprising about 0.5% w/v to about 5% w/v (based on the lipoic acid choline ester) of lipoic acid choline ester tosylate, hydroxypropyl-β-cyclodextrin in an amount equimolar to the lipoic acid choline ester tosylate, about 0.2% w/v to about 1% w/v of a tonicity agent selected from the group consisting of sodium chloride, and potassium chloride, or about 1 mM to about 300 mM of a tonicity agent selected from the group consisting of mannitol, dextrose, and mixtures thereof, about 0.01% w/v to about 1% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include a biochemical energy source, e.g., alanine, and wherein the pharmaceutical composition meets European Pharmacopoeia preservation standards for sterile parenteral multi-dose compositions.

In some embodiments, provided herein are pharmaceutical compositions comprising about 0.5% w/v to about 5% w/v (based on the lipoic acid choline ester) of lipoic acid choline ester tosylate, hydroxypropyl-β-cyclodextrin in an amount about equimolar to the lipoic acid choline ester tosylate, about 0.2% w/v to about 1% w/v of a tonicity agent selected from the group consisting of sodium chloride, potassium chloride, or about 1 mM to about 300 mM of a tonicity agent selected from the group consisting of mannitol, dextrose, and mixtures thereof, about 0.01% w/v to about 1% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, hydroxypropyl-β-cyclodextrin in an amount about equimolar to the lipoic acid choline ester tosylate, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.2% w/v, about 6.3% w/v, about 11.2% w/v, about 15% w/v, or about 19.6% w/v of hydroxypropyl-β-cyclodextrin, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.3% w/v, about 6.7% w/v, about 11.5% w/v, about 15.0% w/v, or about 19.6% w/v of hydroxypropyl-β-cyclodextrin, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, hydroxypropyl-β-cyclodextrin in an amount about equimolar to the lipoic acid choline ester, about 0.1% w/v to about 1% w/v of sodium chloride, about 0.1% w/v to about 0.75% w/v of hydroxypropylmethyl cellulose or hydroxyethyl cellulose, and about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.2% w/v, about 6.3% w/v, about 11.2% w/v, about 15% w/v, or about 19.6% w/v of hydroxypropyl-β-cyclodextrin, about 0.1% w/v to about 1% w/v of sodium chloride, about 0.1% w/v to about 0.75% w/v of hydroxypropylmethyl cellulose, about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

In some embodiments, provided herein are pharmaceutical compositions comprising about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.3% w/v, about 6.7% w/v, about 11.5% w/v, about 15.0% w/v, or about 19.6% w/v of hydroxypropyl-β-cyclodextrin, about 0.1% w/v to about 1% w/v of sodium chloride, about 0.1% w/v to about 0.75% w/v of hydroxypropylmethyl cellulose, about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

US, EP, or JP Pharmacopoeia preservation standards for sterile parenteral multi-dose compositions are known to those of skill in the art and are described, for example, in Moser, C L et al., *AAPS Pharm Sci Tech*. 2011 March; 12(1): 222-226. In some embodiments, the pharmaceutical composition meets European (EP) Pharmacopoeia preservation standards for sterile parenteral multi-dose compositions. In some embodiments, the pharmaceutical composition meets Japanese (JP) Pharmacopoeia preservation standards for sterile parenteral multi-dose compositions.

In some embodiments, the pharmaceutical compositions described herein when incubated with bacterial challenge organisms, achieve not less than 1.0 log reduction from the initial calculated count of the challenge organism at 7 days, and/or not less than 3.0 log reduction from the initial count of the challenge organism at 14 days, and/or no increase from the 14 days' count of the challenge organism at 28 days. In some embodiments, the pharmaceutical compositions described herein when incubated with yeast or mold challenge organisms, achieve no increase from the initial calculated count of the challenge organism at 7, 14, and 28 days.

In additional or alternative embodiments, the pharmaceutical compositions described herein when incubated with bacterial challenge organisms, achieve not less than 1 log reduction from the initial calculated count of the challenge organism at 24 hours, and/or not less than 3 log reduction from the initial count of the challenge organism at 7 days, and/or no increase from the 14 days' count of the challenge organism at 28 days. In particular embodiments, the pharmaceutical compositions described herein when incubated with bacterial challenge organisms, achieve not less than 2 log reduction from the initial calculated count of the challenge organism at 6 hours, and/or not less than 3 log reduction from the initial count of the challenge organism at 24 hours, and/or no recovery of the bacterial count of the challenge organism at 28 days. In some embodiments, the pharmaceutical compositions described herein when incubated with yeast or mold challenge organisms, achieve not less than 1 log reduction from the initial calculated count of the challenge organism at 14 days and/or no increase from the 14 days' count of the challenge organism at 28 days. In some embodiments, the pharmaceutical compositions described herein when incubated with yeast or mold challenge organisms, achieve not less than 2 log reduction from the initial calculated count of the challenge organism at 7 days and/or no increase from the 14 days' count of the challenge organism at 28 days.

In additional or alternative embodiments, the pharmaceutical compositions described herein when incubated with bacterial challenge organisms, achieve a reduction of 0.1% of inoculum count or less 14 days, and a bacterial count at 28 days that is same or less than level after 14 days. In additional or alternative embodiments, the pharmaceutical compositions described herein when incubated with yeast or mold challenge organisms, achieve a microbial count at 28 days that is same or less than level after 14 days.

In any of the microorganism challenge tests described herein, the bacterial challenge organisms are *Staphylococcus aureus, Pseudomonas aeruginosa, Escherichia coli*, or combinations thereof. In particular embodiments, the yeast and mold challenge organisms are *Candida albicans, Aspergillus brasiliensis*, or combinations thereof. In any of the microorganism challenge tests described herein, the challenge organism are incubated at a concentration of $10^5$ to $10^6$ colony forming unit/ml. As described herein, "no increase" in the microbial count means not more than 0.5 log higher than the previous measured level.

In some embodiments, the pharmaceutical compositions described herein contain at least 95%, at least 96%, at least 97%, or at least 98% of the initial amount of lipoic acid choline ester after storage at 25° C. for 10 weeks. In some embodiments, the pharmaceutical compositions described herein contain at least 95%, at least 96%, at least 97%, or at least 98% of the initial amount of lipoic acid choline ester after storage at 25° C. for 13 weeks. In some embodiments, the pharmaceutical compositions described herein contain at least 95%, at least 96%, at least 97%, or at least 98% of the initial amount of lipoic acid choline ester after storage at 25° C. for at least 10 weeks, including, for example, 10 weeks, 3 months, 13 weeks, 6 months, 9 months, 12 months, 15 months, 18 months, 21 months, and 24 months. In some embodiments, the pharmaceutical compositions described herein contain at least 80%, at least 85%, at least 86%, at least 87%, or at least 88% of the initial amount of lipoic acid choline ester after storage at 40° C. for 13 weeks. In some embodiments, the pharmaceutical compositions described herein contain at least 80%, at least 85%, at least 86%, at least 87%, or at least 88% of the initial amount of lipoic acid choline ester after storage at 40° C. for at least 10 weeks, including, for example, 10 weeks, 3 months, 13 weeks, 6 months, 9 months, 12 months, 15 months, 18 months, 21 months, and 24 months.

In alternative or additional embodiments, the pharmaceutical compositions described herein, when administered to a rabbit, result in a maximum aqueous humor lipoic acid concentration (Cmax) that is at least 2 times, at least 2.5 times, at least 3 times, at least 3.5 times at least 4 times, at least 5 times at least 6 times, at least 7 times, at least 8 times, at least 9 times, or at least 10 times the aqueous humor lipoic acid concentration of a pharmaceutical composition that does not include a viscosity modifying agent. In particular embodiments, the viscosity modifying agent is hydroxypropylmethyl cellulose.

In some embodiments, the pharmaceutical compositions described herein, when administered to a rabbit, result in a maximum corneal lipoic acid concentration (Cmax) that is at least 2 times, at least 2.5 times, at least 3 times, at least 3.5 times at least 4 times, at least 5 times at least 6 times, at least 7 times, at least 8 times, at least 9 times, or at least 10 times the aqueous humor lipoic acid concentration of an pharmaceutical composition that does not include a viscosity modifying agent. In particular embodiments, the viscosity modifying agent is hydroxypropylmethyl cellulose.

In some embodiments, the pharmaceutical compositions described herein are suitable for ocular administration. For example, the pharmaceutical compositions described herein do not cause ocular irritation or cause minimal levels of ocular irritation. In particular embodiments, the pharmaceutical compositions described herein include less than about 2, less than about 1%, less than about 0.5%, less than about 0.4%, less than about 0.3%, less than about 0.2% or less than about 0.1% of associative species of LACE, when measured in terms of HPLC peak area relative to LACE.

Method of Making LACE Salt Formulations

In some embodiments, described herein are LACE salt pharmaceutical compositions prepared by the process of:

adding to water an amount of lipoic acid choline ester salt and hydroxypropyl-beta-cyclodextrin to prepare a solution of lipoic acid choline ester and hydroxypropyl-beta-cyclodextrin, optionally adding a tonicity agent, a viscosity modifying agent, a buffer, and a preservative to the solution of lipoic acid choline ester and hydroxypropyl-beta-cyclodextrin, adjusting the pH with an acid or base, optionally adding water to adjust the concentration of LACE salt to the final concentration, and optionally sterilizing the solution to provide a final formulation.

In some embodiments, the LACE salt is LACE tosylate. In some embodiments, the viscosity modifying agent, the LACE salt, and/or the hydroxypropyl-beta-cyclodextrin are added as stock solutions. In some embodiments, the temperature of mixing of lipoic acid choline ester and hydroxypropyl-beta-cyclodextrin is lower than 30° C., or between 20-25° C.

In some embodiments, the mixing is carried out in an inert gas (e.g., nitrogen) atmosphere.

In some embodiments, the pH is adjusted using concentrated sodium hydroxide or concentrated hydrochloric acid. In particular embodiments, the pharmaceutical composition is sterilized by sterile filtration. In further embodiments, the stock solutions and/or the solution of lipoic acid choline ester and hydroxypropyl-beta-cyclodextrin are sterilized by sterile filtration. In particular embodiments, the water is Water for Injection.

In some embodiments, the final pharmaceutical composition is filled in an ophthalmic bottle. In some embodiments, the ophthalmic bottle is selected from the group consisting of Type 1 pharmaceutical glass, high density polyethylene (HDPE), polypropylene (PP), low density polyethylene (LDPE), polyethylene terephthalate (PET), and polytetrafluoroethylene (PTFE). In some embodiments, the ophthalmic bottle is a blow-fill-seal unit. In some embodiments, the ophthalmic bottle is a multi-dose unit. In some embodiments, the ophthalmic bottle is further packaged into a pouch of gas impermeable material. In further embodiments, the gas impermeable material is foil. In further embodiments, the pouch further includes an oxygen scavenger.

Methods of Use

The lipoic acid choline ester salt forms (e.g., as described herein) can be employed in a method for treating or preventing a disease or disorder associated with oxidative damage. Diseases or disorders associated with oxidative damage are known.

In some embodiments, the invention provides a method of treating an ocular disease in a subject in need thereof, comprising administering to an eye of the subject a therapeutically effective amount of any of the LACE salt forms described herein.

In some embodiments, the ocular diseases are presbyopia, dry eye, cataract, macular degeneration (including age-related macular degeneration), retinopathies (including diabetic retinopathy), glaucoma, or ocular inflammations. In particular embodiments, the ocular disease is presbyopia.

In some embodiments, the invention provides a method of treating an ocular disease in a subject in need thereof, comprising administering a pharmaceutical composition comprising lipoic acid choline ester salt at a concentration of about 0.1% to 10% (e.g., 0.1%, 1.0%, 1.5%, 3%, 4%, 5%, or any ranges between the specified numeric values) by weight of the composition, as measured using the LACE cation, without considering the anion. For example, LACE chloride 1.5% w/v corresponds to 1.3% LACE. In particular embodiments, the invention provides a method of treating an ocular disease in a subject in need thereof, comprising administering a pharmaceutical composition comprising lipoic acid choline ester tosylate at a concentration of about 0.1% to 10% (e.g., 0.1%, 1.0%, 1.5%, 3%, 4%, 5%, or any ranges between the specified numeric values) by weight of the composition, as measured using the LACE cation, without considering the anion. In particular embodiments, the ocular disease is presbyopia.

In some embodiments, the invention provides a method of improving distance corrected near vision acuity (DCNVA) in a subject by at least 1 letter, at least 2 letters, at least 3 letters, at least 4 letters, or at least 5 letters, by administering an effective amount of LACE tosylate to the subject. In some embodiments, change from baseline in binocular DCNVA of the subject is assessed. In some embodiments, change from baseline in monocular DCNVA of the subject is assessed.

In some embodiments, the invention provides a method of increase the accommodative amplitude of the lens by at least 0.1 diopters (D) (e.g., 0.1, 0.2, 0.5, 1, 1.2, 1.5, 1.8, 2, 2.5, 3, or 5 diopters) in a subject, by administering an effective amount of LACE tosylate to the subject. In some embodiments, the invention provides a method of treating oxidative damage to cells, by contacting the cells with an effective amount of LACE tosylate.

In some embodiments, the invention provides a method of reducing disulfide bonds in the ocular lens in a subject in need thereof, by administering to the subject an effective amount of LACE tosylate.

Dosages

In some embodiments, provided herein is a method for treating or preventing a disease or disorder associated with oxidative damage, e.g., presbyopia, comprising administering to a patient a total daily dose of about 0.001 mg to about 50 mg of lipoic acid choline ester, in a salt form, e.g., lipoic acid choline ester tosylate, lipoic acid choline ester besylate, lipoic acid choline ester chloride or lipoic acid choline ester iodide. In further embodiments, provided herein is a method for treating or preventing a disease or disorder associated with oxidative damage, e.g., presbyopia, comprising ocularly administering to a patient a total daily dose of about 0.1 mg to about 5 mg of lipoic acid choline ester, about 0.2 mg to about 3 mg of lipoic acid choline ester, about 0.4 mg to about 2.5 mg of lipoic acid choline ester, in a salt form, e.g., lipoic acid choline ester tosylate, lipoic acid choline ester besylate, lipoic acid choline ester chloride or lipoic acid choline ester iodide. In further embodiments, provided herein is a method for treating or preventing a disease or disorder associated with oxidative damage, e.g., presbyopia, comprising ocularly administering to a patient a total daily dose of about 0.2 mg, about 0.4 mg, about 0.5 mg, about 0.8 mg, about 0.9 mg, about 1 mg, about 1.1 mg, about 1.2 mg, about 1.4 mg, about 1.5 mg, about 1.6 mg, about 2.1 mg, about 2.4 mg, about 2.8 mg, or about 3.2 mg, of lipoic acid choline ester, in a salt form, e.g., lipoic acid choline ester tosylate, lipoic acid choline ester besylate, lipoic acid choline ester chloride or lipoic acid choline ester iodide. In some embodiments, the lipoic acid choline ester salt is lipoic acid choline ester tosylate. In particular embodiments, the lipoic acid choline ester comprises (R)-lipoic acid choline ester salt. In further embodiments, the lipoic acid choline ester salt comprises substantially all (R)-lipoic acid choline ester tosylate. In particular embodiments, provided herein is a method for treating or preventing a disease or disorder associated with oxidative damage, e.g., presbyopia, comprising ocularly administering to a patient a total daily dose of lipoic acid choline ester tosylate of about 0.2 mg to about 7 mg, or about 0.5 mg to about 5 mg, or about 0.7 mg to about 3.5 mg, or about 0.3 mg, about 0.8 mg, about 0.6 mg, about 1.0 mg, about 1.5 mg, about 1.7 mg, about 2.0 mg, about 2.2 mg, about 2.3 mg, about 2.5 mg, about 2.6 mg, about 3.0 mg, about 3.4, about 3.9, about 4.5, about 5.0, about 6.0, or about 6.7 mg. In further embodiments, the lipoic acid choline ester salt comprises substantially all (R)-lipoic acid choline ester tosylate. A skilled artisan will appreciate that the total daily dose will be divided by the total number of doses per day to yield the amount per dose.

Routes of Administration and Dosage Regimens

In particular embodiments, the lipoic acid choline ester salt is administered to the eye of the patient. In further embodiments, the administration is to the ocular surface, e.g., cornea, conjunctiva, cul-de-sac, or the corneo-scleral junction, i.e., limbus.

In some embodiments, the lipoic acid choline ester salt, e.g., lipoic acid choline ester tosylate, lipoic acid choline ester besylate, lipoic acid choline ester chloride or lipoic acid choline ester iodide may be administered to the subject in one, two, three, four, or five divided doses per day. In particular embodiments, the LACE salt is administered one, two, or three times daily. In some embodiments, the LACE salt is administered two times daily. In particular embodiments, the LACE salt may be administered to the subject once every one, two, three, four, five, six, or seven days. In some embodiments, the LACE salt may be administered for up to about 12 weeks, or greater than about 12 weeks, e.g., at least four months, at least five months, at least 6 months, at least 9 months, or at least 1 year.

In some embodiments, a drug holiday follows the LACE salt administration period. In some embodiments, the drug holiday period is for at least about two weeks, including, e.g., about two weeks, about three weeks, about one month, about two months, about three months, about four months, about five months, about 6 months, about 9 months, about 12 months, about 18 months, or about 24 months.

Methods of Use

In some embodiments, provided herein is a method for treating or preventing a disease or disorder associated with oxidative damage, e.g., presbyopia, comprising ocularly administering to a patient a pharmaceutical composition comprising:
a lipoic acid choline ester salt,
hydroxypropyl-β-cyclodextrin,
optionally a tonicity agent,
optionally a viscosity modifying agent,
optionally, a buffer,
optionally, a preservative.

In some embodiments, the pharmaceutical compositions are aqueous.

In some embodiments, provided herein a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of a lipoic acid choline ester salt,
about 2% w/v to about 25% w/v of hydroxypropyl-β-cyclodextrin,
up to 300 mM of a tonicity agent,
0% w/v to about 20% w/v of a viscosity modifying agent,
0% w/v to about 1% w/v of a buffer, and
0% w/v to about 0.5% w/v of a preservative.

In some embodiments, provided herein a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of a lipoic acid choline ester salt,
about 2% w/v to about 25% w/v of hydroxypropyl-β-cyclodextrin,
up to 300 mM of a tonicity agent selected from the group consisting of ionic tonicity agents, nonionic tonicity agents, and mixtures thereof,
0% w/v to about 20% w/v of a viscosity modifying agent,
0% w/v to about 1% w/v of a buffer, and
0% w/v to about 0.5% w/v of a preservative.

In some embodiments, provided herein a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 1.5% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0% w/v to about 1% w/v of a buffer, and
0% w/v to about 0.5% w/v of a preservative.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester iodide,
about 2% w/v to about 25% w/v of hydroxypropyl-β-cyclodextrin,
up to 150 mM of a ionic tonicity agent or up to 300 mM of a nonionic tonicity agent, 0% w/v to about 20% w/v of a viscosity modifying agent,
0% w/v to about 1% w/v of a buffer, and
0% w/v to about 0.5% w/v of a preservative.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester besylate,
about 2% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0% w/v to about 1% w/v of a buffer, and
0% w/v to about 0.5% w/v of a preservative.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester chloride,
about 2% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0% w/v to about 1% w/v of a buffer, and
0% w/v to about 0.5% w/v of a preservative.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 2% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0.01% w/v to about 1% w/v of a buffer, and
0% w/v to about 0.5% w/v of a preservative selected from the group consisting of benzalkonium chloride, sorbic acid, boric acid, and mixtures thereof.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 2% w/v to about 25% w/v of hydroxypropyl-β-cyclodextrin,
up to 150 mM of a ionic tonicity agent or up to 300 mM of a nonionic tonicity agent,
0.01% w/v to about 20% w/v of a viscosity modifying agent,
0.01% w/v to about 1% w/v of a buffer, and
0% w/v to about 0.5% w/v of a preservative selected from the group consisting of benzalkonium chloride, sorbic acid, boric acid, and mixtures thereof.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 2% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0% w/v to about 1% w/v of a buffer, and
0% w/v to about 0.5% w/v of a preservative selected from the group consisting of sorbic acid, boric acid, and mixtures thereof,
wherein the pharmaceutical composition does not include a biochemical energy source.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 2% w/v to about 25% w/v of hydroxypropyl-β-cyclodextrin,
up to 150 mM of a ionic tonicity agent or up to 300 mM of a nonionic tonicity agent,
0% w/v to about 20% w/v of a viscosity modifying agent,
0% w/v to about 1% w/v of a buffer, and
0% w/v to about 0.5% w/v of a preservative,
wherein the pharmaceutical composition does not include benzalkonium chloride and does not include a biochemical energy source.

In some embodiments, provided herein is a method for treating or preventing a disease or disorder associated with oxidative damage, e.g., presbyopia, comprising ocularly administering to a patient a pharmaceutical composition comprising:
about 0.5% w/v to about 5% w/v (based on the lipoic acid choline ester) of lipoic acid choline ester tosylate,
about 2% w/v to about 25% w/v of hydroxypropyl-β-cyclodextrin,
about 1 mM to about 150 mM of a tonicity agent selected from the group consisting of sodium chloride, potassium chloride, and mixtures thereof, or about 1 mM to about 300 mM of a tonicity agent selected from the group consisting of mannitol, dextrose, glycerin, propylene glycol and mixtures thereof,
about 0.01% w/v to about 20% w/v of a viscosity modifying agent selected from the group consisting of polyethylene glycols, cellulosic agents, and mixtures thereof,
about 0.01% w/v to about 1% w/v of a buffer selected from the group consisting of phosphate buffers (e.g., sodium phosphate monobasic monohydrate, sodium phosphate dibasic anhydrous), acetate buffer, citrate buffer, borate buffers, and HBSS (Hank's Balanced Salt Solution), and
0% w/v to about 0.5% w/v of a preservative,
wherein the pharmaceutical composition has a pH of about 4.3 to about 4.7, and
wherein the pharmaceutical composition does not include benzalkonium chloride and does not include a biochemical energy source.

In some embodiments, provided herein is a method for treating or preventing a disease or disorder associated with oxidative damage, e.g., presbyopia, comprising ocularly administering to a patient a pharmaceutical composition comprising:

about 0.5% w/v to about 5% w/v (based on the lipoic acid choline ester) of lipoic acid choline ester tosylate, about 1.5% w/v to about 25% w/v of hydroxypropyl-β-cyclodextrin, about 1 mM to about 150 mM of a tonicity agent selected from the group consisting of sodium chloride, potassium chloride, and mixtures thereof, or about 1 mM to about 300 mM of a tonicity agent selected from the group consisting of mannitol, dextrose, and mixtures thereof, about 0.01% w/v to about 20% w/v of a viscosity modifying agent selected from the group consisting of polyethylene glycols, cellulosic agents, and mixtures thereof, about 0.01% w/v to about 1% w/v of a buffer selected from the group consisting of phosphate buffers (e.g., sodium phosphate monobasic monohydrate, sodium phosphate dibasic anhydrous), acetate buffer, and mixtures thereof, and 0% w/v to about 0.5% w/v of a preservative, wherein the pharmaceutical composition has a pH of about 4.3 to about 4.7, and wherein the pharmaceutical composition does not include benzalkonium chloride and does not include a biochemical energy source.

In some embodiments, provided herein is a method for treating or preventing a disease or disorder associated with oxidative damage, e.g., presbyopia, comprising ocularly administering to a patient a pharmaceutical composition comprising:

about 0.5% w/v to about 5% w/v (based on the lipoic acid choline ester) of lipoic acid choline ester tosylate, hydroxypropyl-β-cyclodextrin in an amount equimolar to the lipoic acid choline ester tosylate, about 0.2% w/v to about 1% w/v of a tonicity agent selected from the group consisting of sodium chloride, and potassium chloride, or about 1 mM to about 300 mM of a tonicity agent selected from the group consisting of mannitol, dextrose, and mixtures thereof, about 0.01% w/v to about 1% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include a biochemical energy source, and wherein the pharmaceutical composition meets US Pharmacopoeia preservation standards for sterile parenteral multi-dose compositions.

In some embodiments, provided herein is a method for treating or preventing a disease or disorder associated with oxidative damage, e.g., presbyopia, comprising ocularly administering to a patient a pharmaceutical composition comprising:

about 0.5% w/v to about 5% w/v (based on the lipoic acid choline ester) of lipoic acid choline ester tosylate, hydroxypropyl-β-cyclodextrin in an amount about equimolar to the lipoic acid choline ester tosylate, about 0.2% w/v to about 1% w/v of a tonicity agent selected from the group consisting of sodium chloride, potassium chloride, or about 1 mM to about 300 mM of a tonicity agent selected from the group consisting of mannitol, dextrose, and mixtures thereof, about 0.01% w/v to about 1% w/v of a viscosity modifying agent selected from the group consisting of cellulosic agents, about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, and 0% w/v to about 0.5% w/v of a preservative selected from the group consisting of sorbic acid, boric acid, and mixtures thereof, wherein the pharmaceutical composition has a pH of about 4.3 to about 4.7.

In some embodiments, provided herein is a method for treating or preventing a disease or disorder associated with oxidative damage, e.g., presbyopia, comprising ocularly administering to a patient a pharmaceutical composition comprising:

about 0.5% w/v, about 1.3% w/v, about 2.3% w/v, about 3% w/v, or about 4% w/v (based on the lipoic acid choline ester) of lipoic acid choline ester tosylate, hydroxypropyl-β-cyclodextrin in an amount about equimolar to the lipoic acid choline ester tosylate, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein is a method for treating or preventing a disease or disorder associated with oxidative damage, e.g., presbyopia, comprising ocularly administering to a patient a pharmaceutical composition comprising:

about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.2% w/v, about 6.3% w/v, about 11.2% w/v, about 15% w/v, or about 19.6% w/v of hydroxypropyl-β-cyclodextrin, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein is a method for treating or preventing a disease or disorder associated with oxidative damage, e.g., presbyopia, comprising ocularly administering to a patient a pharmaceutical composition comprising:

about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.3% w/v, about 6.7% w/v, about 11.5% w/v, about 15.0% w/v, or about 19.6% w/v of hydroxypropyl-β-cyclodextrin, about 0.1% w/v to about 1% w/v of a tonicity agent selected from the group consisting of sodium chloride and potassium chloride, about 0.1% w/v to about 0.75% w/v of a viscosity modifying agent selected from the group consisting of cellulosic agents, and about 0.01% w/v to about 0.5% w/v of a buffer selected from the group consisting of phosphate buffers (e.g., sodium phosphate monobasic monohydrate, sodium phosphate dibasic anhydrous), acetate buffer, and mixtures thereof, wherein the pharmaceutical composition has a pH of about 4.3 to about 4.7, wherein the pharmaceutical composition does not include a preservative and does not include alanine, and wherein the pharmaceutical composition meets US Pharmacopoeia preservation standards for sterile parenteral multi-dose compositions.

In some embodiments, provided herein is a method for treating or preventing a disease or disorder associated with oxidative damage, e.g., presbyopia, comprising ocularly administering to a patient a pharmaceutical composition comprising:

about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.2% w/v, about 6.3% w/v, about 11.2% w/v, about 15% w/v, or about 19.6% w/v of hydroxypropyl-β-cyclodextrin, about 0.1% w/v to about 1% w/v of sodium chloride, about 0.1% w/v to about 0.75% w/v of hydroxypropylmethyl cellulose or hydroxyethylcellulose, and about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

In some embodiments, provided herein is a method for treating or preventing a disease or disorder associated with oxidative damage, e.g., presbyopia, comprising ocularly administering to a patient a pharmaceutical composition comprising:

about 0.5% w/v, about 1.3% w/v, about 2.3% w/v, about 3% w/v, or about 4% w/v (based on the lipoic acid choline ester) of lipoic acid choline ester tosylate, about 1.5% w/v, about 2.5% w/v, about 3.3% w/v, about 6.7% w/v, about 11.5% w/v, about 15.0% w/v, or about 19.6% w/v of hydroxypropyl-β-cyclodextrin, about 0.1% w/v to about 1% w/v of sodium chloride, about 0.1% w/v to about 0.75% w/v of hydroxypropylmethyl cellulose or hydroxyethylcellulose, and about 0.01% w/v to about 0.5% w/v of acetate buffer, wherein the pharmaceutical composition has a pH of about 4.3 to about 4.7, wherein the pharmaceutical composition has an osmolality of about 250 mOsm to about 425 mOsm, wherein the pharmaceutical composition does not include a preservative and does not include alanine, and wherein the pharmaceutical composition meets US Pharmacopoeia preservation standards for sterile parenteral multi-dose compositions.

EXAMPLES

Abbreviations
ACN=Acetonitrile
MeOH=methanol
EtOH=ethanol
EtOAc=ethyl acetate
Boc=tert-butyloxy carbonyl
DCM=dichloromethane
DCE=1,2-dichloroethane
DMA=N,N-dimethyl acetamide
DMF=N,N-dimethyl formamide
DMSO=dimethyl sulfoxide
DTT=dithiothreitol
MEK=methylethyl ketone
MTBE=methyl tert-butyl ether
TFA=trifluoroacetic acid
THF=tetrahydrofuran
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaOH=sodium hydroxide
Pd=palladium
Pd/C=palladium on carbon
min=minute(s)
μl=microliter
ng=nanogram
μM=micromolar
nM=nanomolar
mM=millimolar
L=liter
ml or mL=milliliter
μL or μl=microliter
g=gram(s)
mg=milligram(s)
mol=moles
mmol=millimole(s)
meq=milliequivalent
RT or rt=room temperature
ret. t.=HPLC retention time (minutes)
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
XRPD=X Ray powder diffraction
PLM=polarized light microscopy
TGA=thermogravimetric analysis
DVS=Differential vapor sorption
mp=melting point
RH=relative humidity
SEM=scanning electron microscopy The following examples are included to demonstrate non-limiting embodiments of the present invention.

Examples 1-3 demonstrate the difficulty in preparation of a crystalline form of LACE chloride and handling LACE chloride under ambient conditions.

Example 1. Equilibration of LACE Chloride in Solvents

In order to test the solubility of LACE chloride in a number of polar and non-polar solvents, LACE-Cl (100 mg) was weighed into a 4 mL glass vial and 1 mL of solvent added.

The mixture was equilibrated for 7 days, with visual observations at days 1, 2, and 7. If a slurry resulted, it was filtered and clear solutions were either cooled or evaporated. Results are presented in Table 1 below.

TABLE 1

Equilibration at 25° C. for 7 days

| Solvent | Comments |
| --- | --- |
| MeOH | Clear solution after 7 days |
| Acetone | initial suspension, with particles stuck on wall after 7 days |
| ACN | Clear solution after 7 days |
| Dioxane | initial suspension, with particles stuck on wall after 7 days |
| Water | Clear solution after 7 days |
| EtOAc | suspension |
| THF | initial suspension turning sticky |
| DCM | Clear solution after 7 days |
| MEK | initial suspension, with particles stuck on wall after 7 days |
| MTBE | initial suspension, with particles stuck on wall after 7 days |
| Anisole | sticky solid |
| Acetic acid | almost dissolved |
| Benzyl alcohol | Clear solution after 7 days |
| Chloroform | clear solution that yielded an oil after evaporation of solvent |
| Cumene | undissolved solid after 7 days |
| Cyclohexane | undissolved solid after 7 days |
| EtOH | Clear solution after 7 days |
| Ethyl formate | suspension |
| IPAc | undissolved solid after 7 days |
| Nitromethane | Clear solution after 7 days |
| Toluene | sticky solid |
| Pyridine | almost dissolved |
| Xylene | undissolved solid after 7 days |
| 2 Methyl 2 butanone | Clear solution after 7 days |
| 2-Me-THF | sticky solid |
| Petroleum ether | undissolved solid after 7 days |
| Diethyl ether | undissolved solid after 7 days |
| Propylene glycol | Clear solution after 7 days |

As seen in Table 1, LACE chloride is soluble in most polar solvents and does not dissolve in many nonpolar solvents. Further, LACE chloride yielded a sticky solid in a number of solvents.

Example 2. Crystallization of LACE Chloride by Addition of Anti-Solvent

Concentrated solutions of LACE-Cl were prepared by dissolving sufficient amount of LACE-Cl in solvents at room temperature. To these solutions, sufficient volume of select anti-solvents was added until cloudy, layer separation or precipitation occurred. These experiments are summarized below in Table 2.

TABLE 2

Anti-solvent addition results

| Solvent | Anti-solvent | Observation | Comments |
| --- | --- | --- | --- |
| Water | acetone | cloudy | — |
| ACN | | cloudy | — |
| MeOH | | clear | — |
| DCM | | cloudy | — |
| Water | | suspension then oil separates out | |
| MeOH | EtOAc | cloudy | — |
| ACN | | precipitate | PLM: LACE-Cl as @ 0% RH |
| DCM | cyclohexane | separated layer | — |
| MeOH | | separated layer | — |
| DMF | | separated layer | — |
| DMF | hexane | separated layer | — |

As seen in Table 2, a LACE chloride crystalline solid only formed in ACN/EtOAc at 0% RH.

Example 3. Crystallization of LACE Chloride with Water

In order to determine if any stable crystalline hydrate form of LACE chloride can be isolated, a crystallization experiment using 5 equivalents of water to LACE in organic solvents was conducted. LACE chloride was dissolved in 5 equivalents of water, and the solvent added to the LACE chloride aqueous solution. These experiments are summarized in Table 3 below. As seen from the results, no solid form of LACE chloride was obtained.

TABLE 3

Crystallization with 5 equiv. of water in organic solvents

| Solvent | Observation over 1 day | Observation over 14 days |
| --- | --- | --- |
| Acetone/EtOH (75 mg/mL) | clear | clear |
| ACN | clear | clear |
| IPA | clear | clear |
| EtOH | clear | clear |
| Acetone | suspension | oil out |
| MEK | clear | clear |
| EtOAc | oil on the bottom | oil out |

Example 4. Anion Exchange Screening

LACE chloride was subjected to anion exchange with a number of anions, using the sodium salt of the anion. The reactions were carried out on 100 mg scale, in different solvents and at room temperature in the dark due to stability of LACE-Cl and the resultant products. The solvents were ethanol, aqueous isopropyl alcohol, acetone/ethanol, aqueous acetonitrile. LACE chloride was subjected to anion exchange with sodium acetate, sodium maleate, sodium hydrogen maleate, sodium hydrogen tartarate, sodium fumarate, sodium hydrogen fumarate, mono sodium citrate, disodium citrate, trisodium citrate, sodium succinate, sodium hydrogen succinate, sodium phosphate ($Na_3PO_4$), sodium hydrogen phosphate ($Na_2HPO_4$), sodium dihydrogen phosphate ($NaH_2PO_4$), sodium sulfate ($Na_2SO_4$), and sodium ascorbate. Equal equivalents of LACE chloride and sodium salt of the tested anions were equilibrated in different solvents by slurrying for 24 hours to 7 days. The slurry was evaluated to determine if the mixture formed a suspension. Formation of NaCl indicated completion of the reaction. The suspension was filtered and concentrated to isolate the the LACE salt product. Results shown in Table 4 below indicated that none of the experiments led to crystalline salt formation.

TABLE 4

Salt screening

| LACE Salt form desired (Reagent used) | EtOH | Isopropyl alcohol add 20 µL water | Acetone/ EtOH (3:1 v/v) | ACN add 20 µL water | Ratio of LACE-Cl: Base |
|---|---|---|---|---|---|
| LACE-acetate (Na-acetate) | NaCl | sodium acetate + NaCl | sodium acetate + NaCl | sodium acetate + NaCl | 1:1 |
| LACE-hydrogen maleate (Na-hydrogen maleate) | NaCl | NaCl | NaCl | NaCl | 1:1 |
| LACE-tartrate (Na-tartrate) | disodium tartrate | disodium tartrate | disodium tartrate | disodium tartrate | 2:1 |
| LACE-hydrogen tartrate (Na-hydrogen tartrate) | suspension XRPD: Na-bitartrate | suspension XRPD: Na-bitartrate | suspension XRPD: Na-bitartrate | suspension XRPD: Na-bitartrate | 1:1 |
| LACE-fumarate (Na-fumarate) | disodium fumarate | disodium fumarate | disodium fumarate | disodium fumarate | 2:1 |
| LACE-hydrogen fumarate | sodium hydrogen fumarate | sodium hydrogen fumarate | sodium hydrogen fumarate | sodium hydrogen fumarate | 1:1 |
| LACE-citrate (mono-Na-citrate) | mono-Na-citrate | mono-Na-citrate | mono-Na-citrate | mono-Na-citrate | 1:1 |
| LACE-citrate (di-Na-citrate) | di-Na-citrate | gel like | di-Na-citrate | di-Na-citrate | 2:1 |
| LACE-citrate (tri-Na-citrate) | suspension (small amount of solid) XRPD: tri-Na citrate | tri-Na citrate | tri-Na citrate | tri-Na citrate | 3:1 |
| LACE-succinate (Na-succinate) | disodium succinate | disodium succinate | disodium succinate | disodium succinate | 2:1 |
| LACE-hydrogen succinate (Na-hydrogen succinate) | sodium hydrogen succinate + trace amount of NaCl | sodium hydrogen succinate + trace amount of NaCl | sodium hydrogen succinate + trace amount of NaCl | sodium hydrogen succinate + NaCl | 1:1 |
| LACE-phosphate ($Na_3PO_4$) | $Na_3PO_4$ + trace amount of NaCl | $Na_3PO_4$ + trace amount of NaCl | $Na_3PO_4$ + trace amount of NaCl | Na3PO4 | 3:1 |
| LACE-hydrogen phosphate ($Na_2HPO_4$) | $Na_2HPO_4$ | $Na_2HPO_4$ | $Na_2HPO_4$ | gel like | 2:1 |
| LACE-dihydrogen phosphate ($NaH_2PO_4$) | no NaCl | no NaCl | no NaCl | no NaCl | 1:1 |
| LACE-sulfate ($Na_2SO_4$) | $Na_2SO_4$ | amorphous | $Na_2SO_4$ | $Na_2SO_4$ | 2:1 |
| LACE-ascorbate (sodium ascorbate) | sodium ascorbate | suspension XRPD: sodium ascorbate | sodium ascorbate | suspension + 150 µl water sticky XRPD: sodium ascorbate | 1:1 |

In addition to the above experiments, 100 mg LACE chloride was subjected to anion exchange with sodium bromide, sodium iodide, sodium benzenesulfonate, and sodium tosylate, in the following anhydrous solvents: ethanol, acetone, acetonitrile. The reactions were monitored for formation of residual sodium chloride and absence of the reagent by XRPD. Results shown in Table 5 indicate that after one week, only LACE bromide and LACE tosylate salts formed, but LACE bromide was found to be hygroscopic and unsuitable for further development.

TABLE 5

Salt screening results in anhydrous solvents

| LACE salt form (Reagent used) | EtOH | Acetone | ACN | Ratio of LACE: Base |
|---|---|---|---|---|
| LACE-Br (Sodium bromide) | suspension, solids NaCl, solution LACE-Br: XRPD, not pursued | not performed | not performed | 1:1 |

TABLE 5-continued

Salt screening results in anhydrous solvents

| LACE salt form (Reagent used) | EtOH | Acetone | ACN | Ratio of LACE: Base |
|---|---|---|---|---|
| LACE-I (Sodium iodide) | further due to hygroscopicity suspension, solids NaCl, solution LACE-I: XRPD | suspension acetone: XRPD: LACE-I | not performed | 1:1 |
| LACE-OBs (Sodium besylate) | not performed | not performed | NaCl and product | 1:1 |
| LACE-OTs (Sodium tosylate) | not performed | not performed | mixture of product, sodium tolunenesulfonate and NaCl; after 1 week, only product | 1:1 |

Further anion exchange experiments of LACE chloride were carried out with disodium tartarate, sodium hydrogen tartarate, sodium fumarate, monosodium citrate, trisodium citrate, sodium succinate, sodium hydrogen succinate, sodium ascorbate, and sodium tosylate in acetone, methanol, and water. Results are shown in Table 6.

TABLE 6

Additional salt screening in different solvents

| LACE-Salt form (Reagent used) | Acetone | MeOH | Water | Ratio: LACE: Base |
|---|---|---|---|---|
| LACE tartrate (diNa-tartrate) | not performed | not performed | 200 μL water + counter ion + 1 mL ACN no reaction | 2:1 |
| LACE-hydrogen tartrate (Na-hydrogen tartrate) | not performed | suspension counter ion | slurry in water for 1 day, added acetone as anti-solvent, white precipitate XRPD: new form NMR: mainly counter ion. | 1:1 |
| LACE-fumarate (Na-fumarate) | suspension, solids XRPD: mixture of LACE-CL and Na-fumarate | not performed | not performed | 1:1 |
| LACE-citrate (mono-Na-citrate) | suspension XRPD: mono-Na-citrate | not performed | not performed | 1:1 |
| LACE-citrate (tri-Na-citrate) | suspension XRPD: mixture of LACE-CL and tri-Na-citrate | not performed | not performed | 3:1 |
| LACE-succinate (Na-succinate) | not performed | suspension XRPD: counter ion | not performed | 2:1 |
| LACE-hydrogen succinate | not performed | suspension XRPD: counter ion | not performed | 1:1 |
| LACE-ascorbate (sodium ascorbate) | suspension, sticky material | Suspension, XRPD: counter ion + 100 μL water changed color | 200 μL water + counter ion + 1 mL ACN solid: sodium ascorbate + small amount NaCl oil part: NMR: LACE trace amount | 1:1 |
| LACE-ascorbate (sodium ascorbate) | not performed | not performed | LACE-Cl and Na L-ascorbate + 200 μL water, slurry for 4 h, added acetone, sticky precipitate oiled out | 1:1 |
| Sodium tosylate | Incomplete reaction | not performed | not performed | 1:1 |

In addition to the above salts, LACE chloride was treated with aromatic carboxylates niacin sodium, sodium benzoate, and sodium 3,4-dihydroxybenzoate to obtain LACE niacin, benzoate, or 3,4-dihydroxybenzoate salt of LACE. The salt screening was carried out in methanol at 20-25° C. under nitrogen and in the dark.

Results from these experiments showed that the niacin sodium resulted in decomposition of LACE chloride. Anion exchange with sodium benzoate and sodium 3,4-dihyroxybenzoate resulted in oils, which were not the desired product. Additionally, reaction with sodium 3,4-dihydroxybenzoate resulted in a complex product mixture of LACE 3,4-dihydrobenzoate, residual sodium 3,4-dihyroxybenzoate, and NaCl, which was hygroscopic.

Based on the various salt screening experiments, only LACE tosylate, LACE besylate, and LACE iodide were obtained as crystalline materials and selected for further stability testing.

Details on the methodology, instruments, and standards used for stability testing are as follows.

| TGA (thermogravimetric analysis) method | |
|---|---|
| Instrument | TA Discovery |
| Temperature range | 30 to 300° C. |
| Scan rate | 10° C./min |
| Nitrogen flow | 20 mL/min |
| Sample mass | ~2-10 mg |
| DSC (Differential scanning calorimetry) method | |
| Instrument | TA Discovery |
| Temperature range | 30 to 250 or 300° C. |
| Scan rate | 10° C./min |
| Nitrogen flow | 50 mL/min |
| Sample mass | ~2 mg |
| XRPD (X-ray powder diffraction) method 1 (transmission mode) | |
| Instrument | Bruker D8 Advance |
| Detector | LYNXEYE (1D mode), open angle: 1.597°, slit opening: 5.0 mm |
| Radiation | CuKα (0.15406 nm) |
| X-ray generator power | 40 kV, 40 mA |
| Step size, resolution | 0.020 degrees |
| Scan range | 2° to 45° (2 theta value) |
| Slits | primary soller slit: 2.5°, secondary soller slit: 2.5° |
| XRPD method 2 (reflection mode) | |
| Instrument | Bruker D8 Advance |
| Detector | LYNXEYE (1D mode), open angle: 1.198°, slit opening: 5.0 mm |
| Radiation | CuKα (0.15406 nm) |
| X-ray generator power | 40 kV, 40 mA |
| Step size, resolution | 0.020 degrees |
| Scan range | 2° to 45° (2 theta value) |
| Slits | primary soller slit: 2.5°, secondary soller slit: 2.5° |
| DVS (Differential vapor sorption) | |
| Instrument | Advantage |
| Sample mass temperature 25° C. or 60° C. | ~10 mg |
| dm/dt | 0.002%/min |
| NMR (nuclear magnetic resonance) | |
| Instrument | Bruker AVANCE III 400 MHZ |
| Probe | 5 mm PABBO BB-1H/D Z-GRD Z108618/0226 |
| Temperature | 295.7K |
| Relaxation delay | 1 second |
| UPLC (ultra performance liquid chromatography) method | |
| Instrument | Water Acquity UPLC |
| Column Chemistry | Agilent Poroshell |
| Column Manufacture | Agilent |
| Particle Size (um) | 1.7 |
| Dimensions (mm) | 2.1 × 100 |
| Column Temperature (° C.) | 45 |
| Flow Rate (mL/minute) | 0.50 |
| Injection Volume (uL) | 1 |
| Sample Solvent | 5 mL of acetonitrile, add 10 mL 100 mM methanesulfonic acid (Mobile Phase A) and 10 mL 20 mM Tetramethylammonium Chloride. |
| Sample Concentration (ug/mL) | 800 |
| Wavelength (nm) | 210 |
| Mobile Phase A | 100 mM methanesulfonic acid (pH 2.3) |
| Mobile Phase B | Acetonitrile |
| Run Time (minutes) | 13 |
| Gradient | minutes | % B |
| | 0.00 | 10.0 |
| | 11.25 | 70.0 |
| | 12.50 | 70.0 |
| | 13.00 | 10.0 |

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions, sample texture, and wavelength of X-ray radiation used. The agreement in the 2-theta-diffraction angles between specimen and reference is within 0.2° for the same crystal form and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Example 5. Preparation of LACE-Benzenesulfonate (LACE-OBs)

To 4153.0 mg (MW 327.93, 12.66 mmol) of LACE-Cl in a Easymax workstation reactor was added 2350.2 mg sodium benzenesulfonate (MW 180.16, purity 97%, 13.05 mmol). To the solids 50 mL of acetonitrile (dried over molecular sieve) was added. The resulting mixture was stirred at 25° C. for 20 hours, resulting in a suspension.

An aliquot of the suspension was filtered. The filter cake was checked by XRPD. It confirmed to be exclusively sodium chloride indicating a complete anion exchange reaction. The reaction mixture was filtered and filtrate was concentrated on rotary evaporator, providing a yellow solid. To this mixture about 10 mg of seed crystal obtained as described in Table 5 above was added. The solution was evaporated until it turned to deeper yellow thicker mixture. About 50 mL of acetone (anhydrous) was slowly added to the mixture and the mixture was concentrated, repeating this process twice to obtain a yellow solid. About 50 mL of anhydrous acetone was added to the solid to obtain slurry, which was kept at 4° C. for 3 days. The mixture was filtered and filter cake was washed with 10 mL anhydrous acetone. The solid was dried under vacuum at room temperature overnight. LACE-benzenesulfonate was obtained as yellow solid 3.673 g (64.53%). The x-ray diffraction peaks for LACE besylate are presented below in Table 7.

TABLE 7

X-Ray diffraction peaks for LACE besylate

| Angle | d value |
|---|---|
| 4.3 | 20.76 |
| 12.7 | 6.95 |
| 18.4 | 4.81 |
| 19.0 | 4.66 |
| 19.9 | 4.47 |
| 20.6 | 4.31 |
| 20.8 | 4.26 |
| 21.3 | 4.18 |
| 23.3 | 3.81 |
| 24.2 | 3.68 |
| 25.5 | 3.49 |
| 27.6 | 3.23 |
| 31.4 | 2.85 |
| 33.2 | 2.70 |
| 35.0 | 2.56 |
| 35.4 | 2.54 |

Example 6. Preparation of LACE-Toluenesulfonate (LACE-OTs)

To 500 mg (1.52 mmol) of LACE-Cl in a glass bottle was added 329 mg of sodium toluenesulfonate (1.52 mmol) and 10 mL of anhydrous acetone. The resulting mixture was stirred at 25 degree C. for 5 days and centrifuged. To the resulting solids 10 mL of anhydrous acetonitrile was added and the resulting mixture was stirred at 25° C. for 6 hours. The suspension was filtered, filter cake was checked by XRPD to indicate that it was only sodium chloride. The suspension was filtered, and the concentrate was filtered on a rotary evaporator.

When the solution precipitated out a yellow solid, 10 mL acetone was added, and the resulting suspension was stirred in acetone for 1 day at room temperature. The yellow solid was filtered and the solid was dried overnight in a vacuum oven at room temperature. Approximately 300 mg of LACE-toluenesulfonate in Form A was obtained.

Example 7. Crystallization of LACE Tosylate from Saturated Solutions

Approximately 100-300 mg of LACE tosylate (or an appropriate amount to ensure saturation) was dissolved in minimal amount of solvent until no remaining crystals were visible. The solutions were subjected to ambient temperature for slow cooling under agitation.

Eight solvents or solvent mixtures were chosen, depending on the solubility of LACE tosylate. If no suspension was obtained after cooling to room temperature or the suspension was too light to collect enough material for analysis, the vial were stored at 5° C. for at least 5 days or for at least 72 h at −20° C.

The resulting suspension was filtered and the remaining solids were examined by XRPD.

TABLE 8

Crystallization of LACE tosylate from saturated solvents

| Solvent | XRPD | Comments |
|---|---|---|
| acetone | Form A | precipitate out SEM: flake like |
| Acetonitrile | // | clear solution |
| Benzyl alcohol | // | clear solution |
| Water | // | clear solution |
| 2-Butanone | Form A | precipitate out flake like |
| Methyl Isobutyl Ketone | Form A | precipitate out |
| Acetone:Acetonitrile (4:1. v/v) | Form A | precipitate out flake like |
| 2-Butanone:Acetonitrile (4:1, v/v) | Form A | precipitate out |

Explanation "//": not carried out because substance is too soluble in the solvent As seen in Table 8, crystallization from acetone, 2-butanone, acetone/acetonitrile mixture, and 2-butanone/acetonitrile mixture resulted in a crystalline form A of LACE tosylate.

Example 8. Precipitation of LACE Tosylate by Addition of Anti-Solvent

Based on solubility studies, four good solvents were identified for LACE tosylate. In order to determine if crystalline forms of LACE tosylate can be obtained, a near saturated solution of LACE tosylate at 25° C. was directly added under vigorous agitation into an excess of anti-solvent. If there was no immediate precipitation/crystallization, the mixture was kept under stirring at room temperature for a maximum of 24 hours.

The resulting suspension was filtered and the remaining solids were examined by XRPD. If the XRPD differed from the starting material, the solids were further analyzed by DSC and TGA.

TABLE 9

Precipitation of LACE tosylate by addition of anti-solvent

| Good solvent | Anti-solvent | XRPD | Comments |
|---|---|---|---|
| Acetonitrile | EtOAc | Form A | Needle-like crystals after 10 min |
|  | Acetone | clear solution |  |
|  | Toluene | clear solution |  |
| Benzyl alcohol | EtOAc | clear solution |  |
|  | Heptane | clear solution |  |
| DCM | EtOAc | Form A |  |
|  | Heptane | Form A |  |
| EtOH | MTBE | Form A |  |
|  | EtOAc | clear solution |  |
|  | Heptane | clear solution |  |

As seen in Table 9, anti-solvent addition at 25° C. resulted in a crystalline Form A of LACE tosylate.

Example 9. Equilibration with Solvents at 4° C. for 24 Days

About 50 mg of LACE tosylate was suspended in 1.0 mL of solvent (or an amount to ensure a saturated solution) and vibrated at 4° C. for 7 and 24 days.

The resulting suspension was filtered and the remaining solids were examined by XRPD. If the XRPD differed from the starting material, the solids were further analyzed by DSC and TGA. As seen in Table 10, after equilibration at lower temperatures, a second crystalline form (Form B) was identified.

TABLE 10

Equilibration with solvents at 4° C. for 7 days and 24 days

| Solvent | 7 days XRPD | 7 days Comments | 24 days XRPD | 24 days Comments |
|---|---|---|---|---|
| Acetone | + | Form B NMR: no decomposition | + | Form B + small amount of Form A |
| Acetonitrile | // | | // | // |
| Benzyl alcohol | // | | // | // |
| Dichloromethane | // | | // | // |
| Ethanol | // | | + | suspension at 4° C. converted to clear solution at room temperature, solution evaporation resulted in Form A in 10 min |
| Ethyl Acetate | − | | + | Form B |
| Heptane | − | | − | Form A, poor solubility |
| Isopropyl acetate | − | | − | Form A, poor solubility |
| Methanol | // | | // | |
| MTBE | + | Form B | + | Form B |
| Toluene | + | Form B | + | Form B |
| Tetrahydrofuran | + | Form B + NMR: no decomposition | + | Form B + Form A |
| Water | // | | // | // |
| Acetone:Heptane, 1:1 v/v | − | | + | Form B |
| Acetone:water, 95:5 v/v | // | | // | // |
| Acetone:water, 90:10 v/v | // | | // | // |
| Acetonitrile:water, 95:5 v/v | // | | // | // |
| Acetonitrile:water, 90:10 v/v | // | | // | // |
| 2-Butanone | − | | − | Form A |
| Methyl Isobutyl Ketone | − | | − | Form A |
| Acetone:Acetonitrile (4:1. v/v) | + | Form B | + | Form B + trace amount of Form A |
| 2-Butanone:Acetonitrile (4:1, v/v) | + | Form B | + | Form B + trace amount of Form A |
| MIBK:Acetonitrile (4:1, v/v) | + | Form B | + | Form B |
| Acetone:Water (99:1 v/v) | + | Form B | + | Form B |
| 2-Butanone:Water (99:1 v/v) | − | | Form A | + | Form A + Form B |
| MIBK:Water (99:1 v/v) | − | | Form A | + | Form B |

Explanation "−": no change detected
"+": change detected
"//": not carried out because substance is too soluble in the solvent
"blank" not conducted Variable temperature XRPD showed that Form B converts to Form A at 100° C. Conversely, the conversion of Form A to Form B was also observed in solid state during storage at −20° C. over 3 months.

In addition to formation at low temperatures, Form B was also observed to be formed when LACE tosylate was suspended in 1.0 ml of the following solvents followed by vibration at 25° C. for either 7 or 21 days. Results are shown in Table 11 below. Results from solvents in which LACE tosylate is highly soluble are not shown as the compound did not crystallize out of the solution.

TABLE 11

Equilibration with solvents at 25° C. for 7 days or 21 days

| Solvent | 7 days | 21 days |
|---|---|---|
| 1,4-Dioxane | | Form B |
| Acetone | | Form B + trace Form A |
| Ethyl Acetate | | Form B |
| Heptane | | Form A |
| Isopropyl acetate | Form A + trace amount of Form B | Form B + small amount of Form A |
| MTBE | Form A + trace amount of Form B | Form B + Form A |
| Toluene | | Form B + Form A |
| Tetrahydrofuran | | Form A |
| Acetone: Heptane (1:1 v/v) | | Form B |
| 2-Butanone | | Form B |
| Methyl Isobutyl Ketone | | Form A low solubility |
| Acetone:Acetonitrile (4:1. v/v) | Form B | Form B |
| 2-Butanone:Acetonitrile (4:1, v/v) | | Form B |
| MIBK:Acetonitrile (4:1, v/v) | | Form A low solubility |
| Acetone:Water (99:1 v/v) | | Form B |
| 2-Butanone:Water (99:1 v/v) | | Form A |
| MIBK:Water (99:1 v/v) | | Form A low solubility |

Explanation "blank" not conducted

A summary of the properties of Form A and Form B is shown in Table 12.

TABLE 12

Characterization of Form A and Form B

| Parameter | Method | Form A | Form B |
|---|---|---|---|
| DSC melting onset | DSC, 10 K/min | 110.9° C. 88.5 J/g | 80.8° C., 17 J/g
110.7° C., 79 J/g |
| X-ray diffraction | 2-40° (2 theta) | High | High |

TABLE 12-continued

Characterization of Form A and Form B

| Parameter | Method | Form A | Form B |
|---|---|---|---|
| Thermogravimetry | TGA, 20 K/min | 0.13% @ 97.6° C. | 0.16% @ 96.7° C. |
| Morphology | SEM | irregular | irregular, small particle |
| Hygroscopicity | DVS | 0.64% water uptake until 70% RH deliquescent >70% RH | 0.55% water uptake until 70% RH deliquescent >70% RH |
|  | XRPD after DVS | deliquescence leading to dissolution and (partial) recrystallization of form A occurred during desorption phase | deliquescence led to dissolution and (partial) recrystallization of form A occurred during desorption phase |

The x-ray diffraction peaks for LACE tosylate Form A are shown in Table 13.

TABLE 13

X-Ray diffraction peaks for LACE tosylate Form A

| Angle | d value |
|---|---|
| 11.4 | 7.75 |
| 15.2 | 5.82 |
| 18.4 | 4.83 |
| 19.0 | 4.66 |
| 19.4 | 4.57 |
| 19.8 | 4.48 |
| 21.9 | 4.05 |
| 22.9 | 3.89 |
| 24.9 | 3.57 |
| 25.9 | 3.44 |
| 26.7 | 3.33 |
| 27.1 | 3.29 |
| 29.6 | 3.01 |
| 30.4 | 2.94 |
| 32.1 | 2.79 |

The x-ray diffraction peaks for LACE tosylate Form B are shown in Table 14.

TABLE 14

X-Ray diffraction peaks for LACE tosylate Form B

| Angle | d value |
|---|---|
| 7.7 | 11.49 |
| 11.5 | 7.69 |
| 15.4 | 5.77 |
| 18.5 | 4.79 |
| 18.8 | 4.71 |
| 19.2 | 4.63 |
| 20.7 | 4.28 |
| 21.4 | 4.15 |
| 23.0 | 3.86 |
| 24.3 | 3.66 |
| 25.4 | 3.51 |
| 29.6 | 3.02 |
| 30.9 | 2.90 |
| 32.7 | 2.74 |

Example 10, Alternative Synthesis of LACE Tosylate

In an alternative procedure, LACE tosylate was prepared as depicted in the synthetic scheme below.

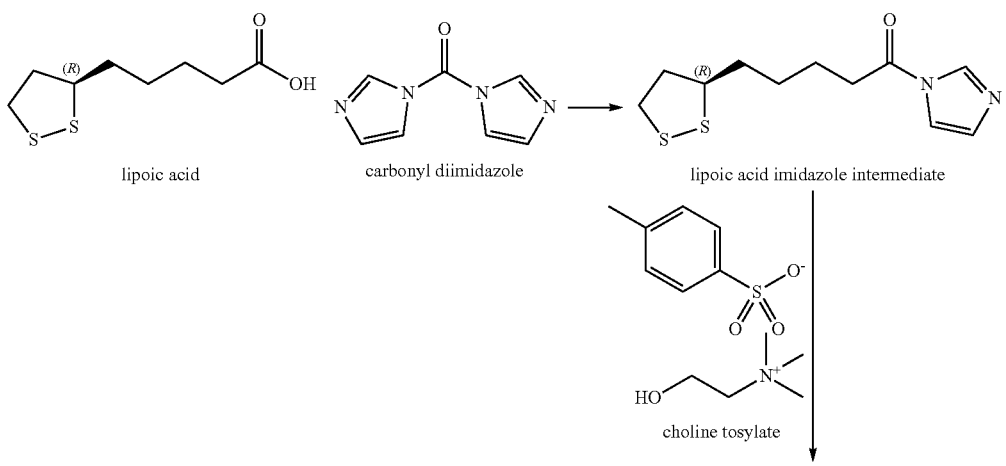

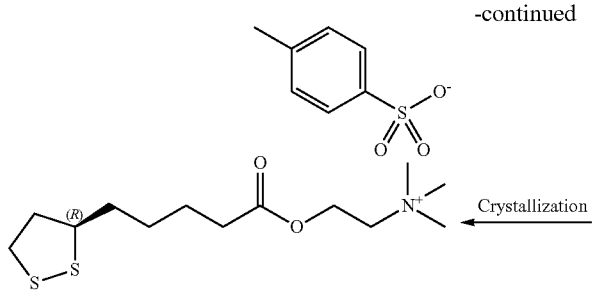 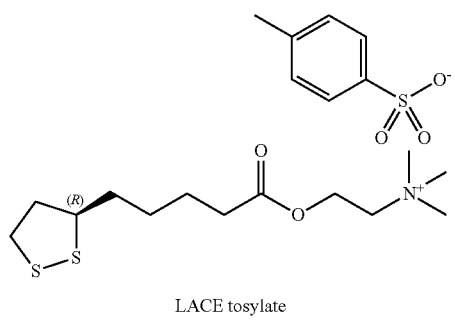

LACE tosylate

The reaction procedure is as follows.

Preparation of lipoic acid imidazole intermediate: To a 2 liter reactor charged with 68.0 g (419.4 mmol) 1,1'-carbonyldiimidazole at 20° C., 225 mL of 2-methyltetrahydrofuran was added and the resulting suspension was cooled to −10° C. and 2.37 g (18.32 mmol) Hunig's base (N,N-diisopropylethylamine) was added. Next, a solution of 75.0 g (363.5 mmol) (R)-lipoic Acid in 375 mL 2-methyltetrahydrofuran was added continuously within 60 min and the dropping funnel rinsed with additional 2-methyltetrahydrofuran. The reaction mixture was warmed to 0° C. over 60 min, stirred for 30 min and warmed to 25° C. over 30 min. The obtained suspension was filtered over a K900 filter plate and the filter was washed with 2-methyltetrahydrofuran. To the resulting clear yellow solution 75 mL of tert-butyl methyl ether (TBME) was added and the solution was stirred for 30 min. The solution was cooled to −15° C. over 12 h, resulting in a suspension, which was stirred at −15° C. for 4.5 h. The product was collected by filtration and the filter cake was washed three times with TBME at −15° C. The product was dried under vacuum at 25° C. to yield 96.4 g (85%) of lipoic acid imidazole intermediate as a yellow crystalline material.

Preparation of choline tosylate: A 500 mL reactor was charged at 25° C. with 50 g (268.5 mmol) methyl tosylate and 100 mL acetone to which a solution of 25.1 g (281.6 mmol) N,N-dimethyl ethanolamine in 50.3 g acetone was added continuously at 25° C. over 3 h. The dropping funnel was rinsed with additional acetone. The reaction mixture was stirred at 25° C. for 20 h and the reaction progress was monitored by HPLC. When the level of methyltosylate was lower than 500 ppm the resulting suspension was cooled to 0° C. over 150 min and the suspension was stirred at 0° C. for 60 min. The product was collected by filtration, washed two times with 175 mL acetone and dried under vacuum at 25° C. to obtain 73.1 g (99%) of choline tosylate as a white crystalline solid.

Preparation of LACE tosylate: A 500 mL reactor was charged at 25° C. with 61.0 g (221.5 mmol) choline tosylate, 70.8 g (227.5 mmol) lipoic acid imidazole intermediate, 300 mL acetonitrile and 300 mL acetone. Hunig's base (2.81 g, 21.8 mmol) was added to the suspension at 25° C. and the reaction mixture stirred at 25° C. for 27 h while monitoring the reaction progress by HPLC. After reaction completion 6.0 g activated charcoal was added and the mixture stirred for 30 min at 25° C. The suspension was filtered over a K900 filter plate and the filter was washed with 120 mL acetone/acetonitrile (1:1). The obtained clear solution was warmed to 30° C. and 1200 mL TMBE was added over 1 h. The resulting suspension was stirred at 30° C. for 1 h followed by cooling the mixture to −15° C. over 12 h. The resulting suspension was warmed to 30° C. over 4 h and cooled again over 12 h to −15° C. and maintained at −15° C. for 12 h. The product was collected by filtration and washed three times with 300 mL acetone at −15° C. The product was dried under vacuum at 25° C. to yield 90.7 g (88%) LACE tosylate.

Recrystallization of LACE Tosylate:

Crystallization Using 2-Butanone/Water

Activated charcoal treatment: A mixture of 450.0 g 2-butanone and 18.0 g water was prepared. In a separate glass bottle, 5.0 g of activated charcoal was suspended in a small fraction of the 2-butanone/water mixture. To a 750 ml reactor containing 50.0 g of crude LACE tosylate, the remaining fraction of the 2-butanone/water mixture (444.6 g) was added while stirring at 20° C. After stirring for approximately 100 min, a yellow and slightly opaque solution was obtained and charged into the container with the activated charcoal suspension, thus creating a black suspension. After stirring for 80 minutes, the suspension was filtered, rinsing the glass bottle and filter cake with additional 2-butanone.

Crystallization: The clear and yellow solution was transferred into a 3500 mL reactor and heated up to 30° C. with stirring and 2-butanone (1225.0 g) was added continuously over 120 min. The solution was stirred for an additional 30 min before starting cooling to −5° C. over 4 hours. Onset of crystallization was observed at about 18.5° C. The suspension was held at −5° C. for 30 min, heated to 30° C. over 2 hours, held at 30° C. for 30 min, cooled to −15° C. over 10 hours, and stirred for 3 hours at −15° C. The suspension was filtered (4-7 μm pore size filter) washing the filter cake 3 times with cold acetone (−20° C.), the washing time being less than 1 minute. During filtration and washing, the filter was kept under nitrogen flow. The product was dried in a vacuum oven at 25° C. and 2 mbar for 18.5 hours. After drying, 42.65 g of LACE tosylate was recovered (85% yield). LACE tosylate was sieved manually with a hand sieve (1 mm mesh size) in order to disaggregate agglomerates, resulting in a slightly cohesive up to easy flowing powder of LACE tosylate.

Alternate Crystallization Using Acetonitrile/Acetone

Activated charcoal treatment: In a 250 mL FlexyLAB reactor, 6.5 g of crude LACE tosylate and 0.65 g of activated charcoal were mixed in solid state by stirring, to which 43.4 g of acetonitrile was added while stirring. The obtained black suspension was brought to 30° C. and stirred for 145 minutes. The suspension was filtered, resulting in a clear and yellow solution.

Crystallization: In another 250 mL FlexyLAB reactor, the filtered solution was brought to 30° C. under stirring to which acetone (83.7 g) was added by continuous dosing over 60 min. The resultant clear and yellow solution was stirred for an additional 60 min and cooled to 0° C. in 10.5 h. Onset of crystallization was observed at about 17.8° C. The resulting slightly yellow suspension was stirred at 0° C. for additional 8 hours. The suspension was filtered (S&S filter, 4-7 µm pore size filter) and the filter cake was washed with 2 portions of cold acetone (0° C.). During filtration and washing, the filter was kept under Nitrogen flow. The product was dried on the glass filter holder in a vacuum oven at 25° C. and 2 mbar for 45 hours. After drying, 4.2 g of LACE tosylate, partly agglomerated, was recovered from the filter, i.e., the yield was 64% for this process step.

The above synthetic route and recrystallization procedure has the following advantages:

Lipoic acid imidazole intermediate is stable and can be isolated. The isolation reduces the risk of the formation of impurities formed by a reaction of CDI with choline in the next step.

Enantiomeric purity The inventors surprisingly observed that there is depletion of the S isomer upon synthesis of intermediate, thereby enhancing the concentration of the desired (R) isomer. As a result, the amount of S isomer in the final active pharmaceutical ingredient is lower than 2%.

During the preparation of choline tosylate, only one solvent is used and the reaction is carried out under more concentrated conditions. The reaction does not use elevated temperatures or distillation, reducing energy consumption, and uses environmentally friendly solvents. Finally, the reaction scheme does not introduce methyltosylate in the last step, reducing the likelihood of genotoxic reagent methyltosylate in the final product.

During crystallization using 2-butanone/water, strict control of temperature and limiting the maximum temperature to 30° C. was able to provide good control on the generation of associative species, which are known to cause ocular irritation. Furthermore, the use of activated charcoal reduces any associative species formed. Additionally, these measures result in formation of Form B, which is the stable form at temperatures lower than 25° C. During the alternative recrystallization procedure, the additional heating/cooling cycle during crystallization reduces the time required for filtration and washing of the suspension. The entire process is based on solvents with low toxic potential, i.e., class 3 according to ICH guidelines.

The following exemplary analytical methods were used to quantify the purity of lipoic acid choline ester tosylate and (R)-lipoic acid choline ester tosylate.

Analytical Conditions for Lipoic Acid Choline Ester Tosylate Analysis

LACE tosylate is analyzed under the following chromatographic conditions:

Apparatus HPLC system with gradient elution and UV detector, e.g., Agilent 1260

Column: Poroshell Phenyl Hexyl

Particle size: 2.7 µm, Supplier(s): e.g., Agilent

Length: 100 mm, Internal diameter: 4.6 mm

Column Temperature: 15° C. Autosampler temperature: 5° C.

Mobile phase: A: 75 mM potassium hexafluorophosphate (KPF$_6$) in water made, for example, by mixing 13.8 g of KPF$_6$ with 1 L of water, adding 1 mL phosphoric acid, and stirring until KPF$_6$ is dissolved. Filter through 0.2 µm nylon membrane filter.

|  | B: Acetonitrile | | | | |
|---|---|---|---|---|---|
| Time [min] | Initial | 20 | 25 | 25.1 | 30 |
| Gradient: % B | 25 | 75 | 75 | 25 | 25 |

Flow Rate: 1.2 mL/min Run time: 30 min

Injection volume: 15 µL

Detection UV Wavelength: 210 nm

Analytical Conditions for Lipoic Acid Choline Ester Tosylate Analysis

The enatiomeric purity of LACE salts, e.g., LACE tosylate is measured by hydrolyzing LACE to lipoic acid and choline, and measuring the enantiomeric purity of lipoic acid. An exemplary method for hydrolysis of LACE salt is as follows: 25 mg LACE salt (e.g., LACE tosylate) is dissolved in 12 mL of acetonitrile and 12 mL of water with 250 µL of 1N NaOH added to this solution. The solution is kept at at room temperature for 30 (±5) minutes, which is sufficient to hydrolyze LACE to lipoic acid. The solution is neutralized with 250 µL of 10% methane sulfonic acid and diluted to appropriate volume with water. This lipoic acid solution is now analyzed for enantiomeric purity using the following exemplary HPLC method.

Apparatus HPLC system and UV detector, e.g. Agilent 1260

Column: CHIRALPAK AY-3R

Particle size: 3 µm, Supplier(s): e.g., Daicel

Length: 100 mm, Internal diameter: 4.6 mm

Column Temperature: 30° C. Autosampler temperature: room temperature

Mobile phase: A: 100 mM Methanesulfonic acid (MSA) prepared, for example, by mixing 6.5 mL of MSA with 1 L of water and add 4.5 mL of 50% sodium hydroxide.

|  | | B: Acetonitrile |
|---|---|---|
| Isocratic: | % A | 70 |
|  | % B | 30 |

Flow Rate: 1 mL/min Run time: 20 min

Injection volume: 15 µL

Detection UV Wavelength: 210 nm

Figure 16:
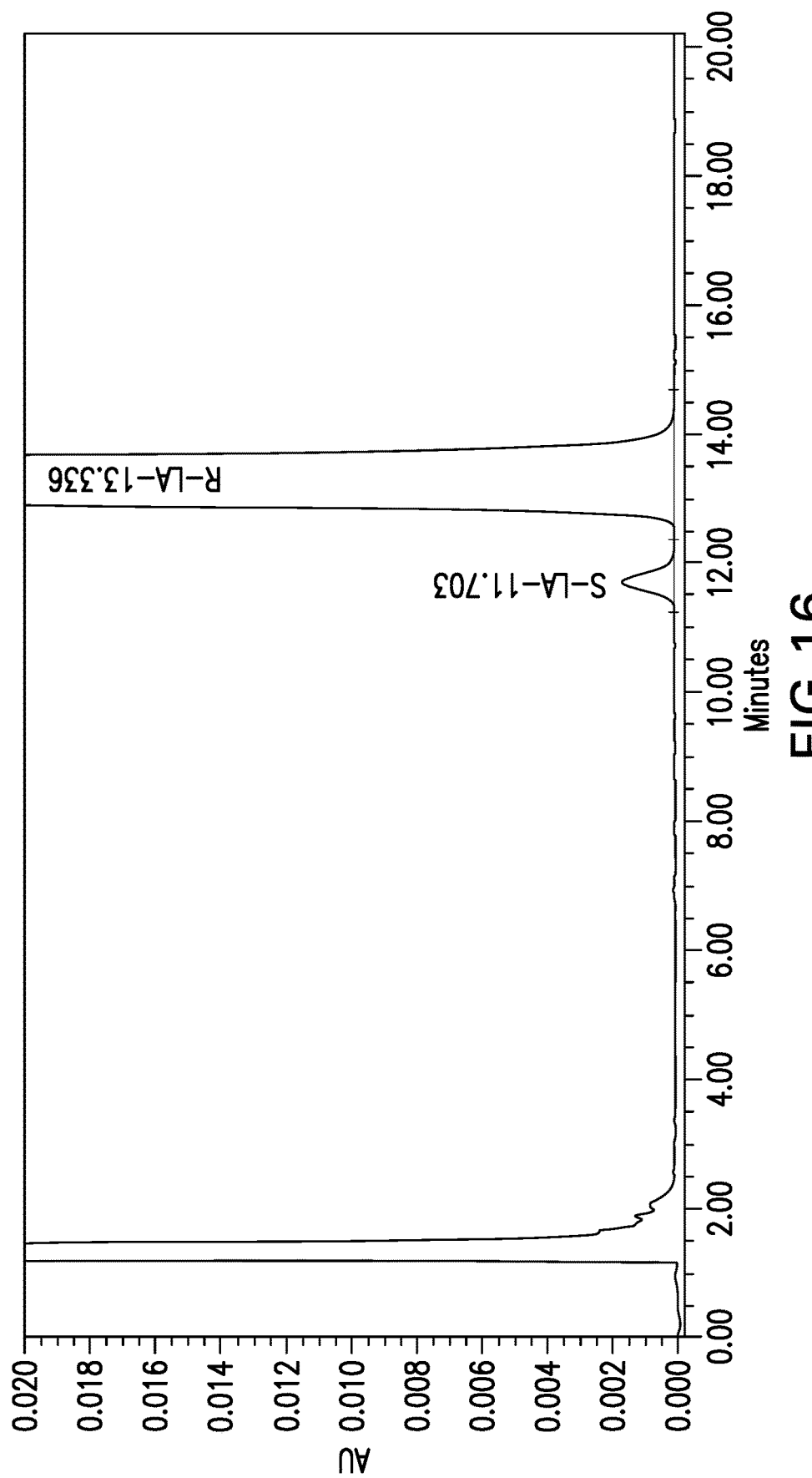
FIG. 16 provides a HPLC chromatogram of lipoic acid choline ester tosylate prepared by an exemplary method and comparing the amounts of (R) and (S) isomers.

FIG. 16 provides a HPLC chromatogram of lipoic acid choline ester prepared by the above method and showing that the amount of (S) isomer (as measured after hydrolysis to lipoic acid) was lower than 2% of the (R) isomer.

The following references were referred to:

Belyaev, A. A.; Radina, L. B.; Novoselova, A. A., Bulletin of the Academy of Sciences of the USSR Division of Chemical Science, 1988, 37, 2293-2296 and Izvestiya Akademii Nauk SSSR, Seriya Khimicheskaya, 1988, 11, 2542-2545.

Lukac, Milos; Mojzis, Jan; Mojzisova, Gabriela; Mrva, Martin; Ondriska, Frantisek; Valentova, Jindra; Lacko, Ivan; Bukovsky, Marian; Devinsky, Ferdinand; Karlovska, Janka, European Journal of Medicinal Chemistry, 2009, 44, 4970-4977.

National Institute Of Advanced Industrial Science And Technology; Tanaka, Mutsuo; Yoshioka, Kyoko; Satou, Yukari; Niwa, Osamu; Fujimaki, Makoto; Mizutani, Wataru; Yoshida, Yasukazu, JP5751578 B2.

Tanaka, Mutsuo; Sawaguchi, Takahiro; Sato, Yukari; Yoshioka, Kyoko; Niwa, Osamu, Tetrahedron Letters, 2009, 50, 4092-4095.

Klykov; Serebrennikova, Russian Chemical Bulletin, 1998, 47, 1547-1549.

Example 11. Preparation of LACE-3,4-DHBz (Salt/Co-Crystal)

To 308 mg of 3,4-dihydroxybenzoic acid and 365.2 mg of sodium 2-ethylhexanoate in a 100 mL reactor, 50 ml of methanol (reagent grade) was added. The resulting slurry was stirred at 25° C. for about 20 hours. A solution containing 658 mg of LACE-Cl dissolved in 20 mL of methanol was added dropwise into the resulting mixture over 2 hours. After complete addition almost clear solution was observed. The resulting mixture was stirred at 25° C. for 20 hours. The reaction mixture was filtered and the filtrate was collected as a clear solution. The filtrate was concentrated on rotary evaporator at 25° C. under vacuum at 10 mbar. Anhydrous acetone (50 mL) was added into the residual material. The resulting mixture was equilibrated at 25° C. for 20 hours. The slurry was filtered and cake was washed with 5 mL of anhydrous acetone. The filter cake was dried at 25° C. under vacuum for 6~8 hours to obtain 835 mg of off-white solid. The H-NMR analysis of the product indicated the stoichiometry of LACE: 3,4-dihydroxybenzoate as 1:2 and the IC analysis indicated ratio of LACE: Na as 1:2.

Note: The NaCl produced in the reaction was not removed from desired product in this process. The inventors hypothesize that the product is an anion exchange product and may be a co-crystal or an admixture with Na-3,4-dihydroxybenzoate and NaCl.

The x-ray diffraction peaks for LACE 3,4-dihydroxybenzoate are shown in Table 15.

TABLE 15

XRPD peaks for LACE 3,4-dihydroxybenzoate

| Angle | d value |
|---|---|
| 6.2 | 14.23 |
| 10.8 | 8.18 |
| 12.5 | 7.09 |
| 14.5 | 6.10 |
| 15.5 | 5.70 |
| 16.7 | 5.31 |
| 17.4 | 5.10 |
| 18.0 | 4.93 |
| 18.5 | 4.78 |
| 19.6 | 4.53 |
| 19.9 | 4.45 |
| 21.9 | 4.06 |
| 24.2 | 3.68 |
| 25.1 | 3.55 |
| 25.8 | 3.45 |
| 26.8 | 3.32 |
| 27.4 | 3.25 |
| 31.7 | 2.82 |

Example 12. Crystalline Form of Lipoic Acid Choline Ester Iodide

Lipoic acid choline ester iodide may be prepared by the procedure described in, for example, US Pat. Appl. Publ. No. 2010/0317725. Briefly, (R)-lipoic acid is treated with N,N-dimethyl ethanolamine in the presence of a suitable coupling agent such as dicyclohexyl carbodiimide (DCC), optionally in the presence of a base such as dimethylamino pyridine (DMAP), to yield (R)-2-(dimethylamino)ethyl-5-(1,2-dithiolan-3-yl)pentanoate. (R)-2-(Dimethylamino) ethyl-5-(1,2-dithiolan-3-yl)pentanoate is further reacted with methyl iodide in a suitable solvent to yield LACE iodide, which may be crystallized from a suitable solvent to provide a crystalline form. LACE iodide has the following x-ray diffraction pattern.

TABLE 16

XRPD pattern of LACE iodide

| Angle | d value |
|---|---|
| 4.9 | 18.03 |
| 18.3 | 4.84 |
| 19.5 | 4.55 |
| 20.6 | 4.30 |
| 22.1 | 4.02 |
| 24.0 | 3.70 |
| 24.4 | 3.64 |
| 27.4 | 3.25 |
| 29.4 | 3.04 |
| 30.2 | 2.95 |
| 31.5 | 2.84 |
| 31.9 | 2.81 |
| 33.6 | 2.66 |
| 34.4 | 2.61 |
| 36.2 | 2.48 |

Example 13. Comparative Stability Testing of Selected LACE Salts

Stability in aqueous solutions or suspensions: LACE-Cl, LACE-I and LACE-OBs show extremely poor stability (10-99% degradation) in acidic as well as basic aqueous pH buffer solution and also in water at 40° C. for 1 week. At pH 4.7 buffer solution about 4% degradation is observed. The stability of LACE-OTs is similar to that of LACE-OBs.

Stability in organic solutions or suspensions: LACE-Cl, LACE-I, LACE-OBs and LACE-OTs show complete degradation in methanol and ethanol, severe degradation in other solvents (EtOAC, acetone, IPA and THF) at 40° C. for 1 week. They are stable as a 0.1% solution in acetonitrile and 0.1% suspensions in heptane under the same conditions (<2% degradation).

Solid state stability: LACE-Cl shows approximately 7% degradation and becomes sticky mass at 40° C. for 1 week as well as at 40° C. 75% RH for 1 week. LACE-I, LACE-OBs and LACE-OTs are stable at 40° C. for 1 week without a change in physical form. However, at 40° C. 75% RH for 1 week, LACE-OBs and LACE-OTs become sticky and only LACE-I form remains the same; they all show 4-7% degradation.

Photostability: In a clear vial LACE-Cl, LACE-I, LACE-OBs and LACE-OTs all show severe degradation and color change. LACE-Cl becomes sticky while LACE-I remains unchanged. LACE-OBs show decrease in crystallinity. LACE-OTs shows some amorphous content. In an amber vial LACE-I, LACE-OBs and LACE-OTs are stable except LACE-Cl which has ~5% degradation and becomes sticky. The physical form remains the same for LACE-I, LACE-OBs and LACE-OTs.

Excipient compatibility: 5% solutions of LACE-Cl, LACE-I and LACE-OBs show about 5% degradation in aqueous excipients at 40° C. for 2 weeks. LACE salts were dissolved in each of the following excipients: 0.01% benzalkonium chloride, 20 mM acetate buffer, 20 mM citrate buffer, 1% Na-carboxymethyl cellulose, 1% hydroxypropylmethyl cellulose and 0.01% Na-ethylene diamine tetraacetic acid. A 5% solution of LACE-OTs in the same excipient compatibility test at 40° C. for 1 week shows about 1-3% degradation. All candidates show severe degradation in 1% alanine and 1% histidine solutions at 40° C. for 2 weeks.

In a excipient compatibility study at 25° C. for 1 week, LACE-Cl shows ~8% and 3.35% degradation with HPMC and HPβCD, respectively and 2-3% degradation in Na-CMC, alanine and histidine. LACE-I and LACE-OBs have <2% degradation under same conditions. At 40° C. for 2 weeks, LACE-Cl, LACE-I and LACE-OBs have higher degradation while LACE-OTs has <2% degradation at 40° C. for 1 week except in HPMC in which all candidates have 4-6% degradation. At 40° C./75% RH for 2 weeks with the same excipients, LACE-Cl, LACE-I and LACE-OBs have high-severe degradation while LACE-OTs has high degradation at 40° C. at 1 week.

Example 14. Chemical and Physico-Chemical Properties

Thermal property: LACE-Cl shows multiple thermal events in DSC. The first event is at 79.4° C. with enthalpy of 17.8 J/g and the second event at 131.7° C. with enthalpy of 43.7 J/g. LACE chloride exhibits a weight loss of 1.1% at 64.2° C., 1.1% at 131.7° C. and 2.0% at 197.8° C. by TGA.

LACE-I shows single melting point at 112.4° C. and melting enthalpy of 82.3 J/g. It exhibits 0.2% weight loss at 152.6° C. by TGA.

LACE-OBs shows single melting point at 80.3° C. and melting enthalpy of 90.6 J/g. It exhibits 0.3% weight loss at 139.4° C. by TGA.

LACE-OTs shows single melting point at Tonset 107.0° C. and melting enthalpy of 75.9 J/g. It exhibits 0.16% weight loss at 88.3° C. by TGA.

In the heat/cool/heat cycle DSC, all 4 candidates show melting and recrystallization during cooling followed melting in the second heating cycle. LACE-Cl exhibits a form change during the DSC cycle.

Example 15. Morphic Properties

Hygroscopicity: LACE-Cl is highly hygroscopic at ambient conditions. It is deliquescent upon exposure to 58% RH for one day. In DVS measurement, LACE chloride absorbs 18.6% moisture from 0% RH to 50% RH. The DVS isotherm is irreversible. It is amorphous at ambient but crystalline under 0% RH by Cryo-XRPD.

LACE-I is non-hygroscopic upon exposure at 58% RH for one day and by DVS. The form is unchanged after DVS. It is highly crystalline solid but changes color upon exposure to ambient conditions.

LACE-OBs salt form is highly crystalline but hygroscopic. It is deliquescent upon exposure at 58% RH for one day but non hygroscopic up to 6 hours. In DVS, from 50% RH to 90% RH it is deliquescent but the initial form was recovered after DVS study due to recrystallization in the desorption phase of the DVS cycle.

LACE-OTs is highly crystalline and non-hygroscopic at 58% RH for one day. In DVS it absorbs less than 2% moisture up to 60% RH and the form remains unchanged after DVS study.

Crystal modification: Upon equilibration in solvents in which it is insoluble, LACE-Cl becomes a deliquescent sticky solid. Form change is observed during DSC and variable-temperature XRPD studies. LACE-I and LACE-OBs do not indicate polymorphic behavior upon equilibration in solvents for 24 hours or during DSC analysis.

Based on the results from the salt selection and polymorphism study, it was seen that LACE-Cl is hygroscopic, sensitive to oxygen, light and moisture and is not suitable for handling under normal conditions. LACE-I exhibits discoloration and possibly slow degradation at ambient conditions in solid state. LACE besylate and LACE tosylate can both be handled at ambient conditions without any degradation.

Example 16. LACE Tosylate Pharmaceutical Composition Development

It was found that LACE salts spontaneously polymerize in water, forming associative species. Associative species of LACE was found to be an ocular irritant. Formation of associative species is dependent on many factors, including concentration of LACE, manufacturing process, temperature, and time. Moreover, the formation of associative species was found to be irreversible. Accordingly, the formation of associative species must be controlled during both API synthesis and preparation of the formulation.

A number of excipients were explored to determine which excipients would reduce the formation of associative species. Acute rabbit ocular tolerability studies were performed to test the ocular tolerability of LACE tosylate with various excipients. The study design involved three male rabbits per arm. The rabbits' left eye was dosed 6 times with one drop each time, about 1 hour apart, administering about 30 microliter per drop. The right eye was not dosed and served as a control. As seen by the results of rabbit ocular tolerability in Table 17, it was determined that inclusion of equimolar amounts of hydroxypropyl beta cyclodextrin reduced or prevented the formation of associative species.

TABLE 17

Acute rabbit tolerability results with different formulation excipients

| Excipient | Rationale | Tolerated |
|---|---|---|
| Propylene Glycol | Positive control | No |
| 0.7% LACE-OTs (0.44% LACE) with HP-β-CD | Testing HP- β-CD to prevent formation of associative species | Yes |
| 2.2% LACE-OTs (1.38% LACE) with HP-β-CD | | Yes |
| 6.2% LACE-OTs (3.9% LACE) with HP-β-CD | | Yes, minimal irritation |
| 1.9% LACE-I (1.33% LACE) with HP-β-CD and hydroxypropyl methyl cellulose (HPMC) | Testing HPMC as a viscosity modifier | Yes |
| Vehicle with 30% polyethylene glycol (PEG) 300 (no HP-β-CD) | Testing PEG as alternative to HP-β-CD | Yes |
| 2.2% LACE-OTs (1.3%) with 10% PEG 300 (no HP-β-CD) | | No |
| 1.3 % LACE (Cl), 1.5% Glycerin, 0.5% Alanine, 0.005% BAC | Negative control and comparator | Yes |

As seen in above, use of HP-β-CD prevented the formation associative species, and thereby resulted in a tolerable ocular formation with no or minimal irritation.

Based on the data from the acute rabbit tolerability studies, prototype LACE tosylate pharmaceutical compositions were prepared and tested in rabbit ocular bioavailability studies. Their compositions are shown in Table-18.

TABLE 18

Compositions of LACE tosylate formulations

| Component | Amount (w/v%) |
|---|---|
| LACE-OTs | 0.7 to 6.4% |
| Sodium acetate trihydrate (buffer) | 0.07% |
| Hydroxypropyl-β-cyclodextrin (HP-β-CD) | 2 to 25% (molar equivalent of LACE-OTs) |
| Glycerin | 0-1.5% |
| Hydroxypropyl methylcellulose (HPMC) | 0-1% |
| Salt (e.g., NaCl as a tonicity agent) | 0-1% |
| Sodium hydroxide/Hydrochloric acid | Qs to pH 4.5 |
| Purified Water | Qs to 100% |
| Preservative (optional) | 0%-0.1% |
| Osmolality | 108-510 mOsm |
| Surface tension | 35-60 mN/m |
| pH | 4.25-4.75 |
| Viscosity (cps), CP52, @60 rpm | 1-90 |

The following specific pharmaceutical compositions were prepared for stability, toxicology, and ocular bioavailability studies.

TABLE 19

Compositions of LACE salt ocular formulations

| Component | Percent (w/v) | | | | | | | | | | |
|---|---|---|---|---|---|---|---|---|---|---|---|
| LACE Cl | 1.5 | 1.5 | 3.3 | — | — | — | — | — | — | — | — |
| LACE Tosylate | — | — | — | 0.79 | 0.81 | 2.2 | 2.2 | 2.2 | 2.2 | 2.2 | 2.2 |
| LACE equivalent | 1.3 | 1.3 | 3 | 0.5 | 0.50 | 1.3 | 1.3 | 1.3 | 1.3 | 1.3 | 1.3 |
| HP-β-CD | — | 6.3 | 15 | 2.5 | 2.5 | 6.3 | 6.3 | 3.15 | 6.3 | 6.3 | 6.3 |
| HPMC | — | — | — | 0.5 | 0.5 | — | — | — | — | — | — |
| Benzalkonium chloride (preservative) | 0.005 | 0.02 | 0.02 | — | — | 0.02 | 0.02 | — | — | — | — |
| Sorbic Acid | — | — | — | — | — | — | — | — | — | — | — |
| NaCl | — | 0.5 | 0.25 | 0.75 | 0.6 | 0.5 | 0.5 | — | — | 0.5 | 1.0 |
| Glycerin | 1.4 | — | — | — | — | — | — | — | — | — | — |
| PEG 300 | — | — | — | — | — | — | — | 5.3 | — | — | — |
| Alanine | 0.5 | — | — | — | — | — | 0.5 | — | — | — | — |
| NaOAc (buffer) | — | 0.07 | 0.07 | 0.07 | 0.07 | 0.07 | — | 0.07 | 0.07 | 0.07 | 0.07 |
| NaOH/HCL (pH adjust) | pH 4.5 | pH 4.5 | pH 4.5 | pH 4.5 | pH 4.5 | pH 4.5 | pH 4.5 | pH 4.5 | pH 4.5 | pH 4.5 | pH 4.5 |
| Purified Water | qs 100 | qs 100 | qs 100 | qs 100 | qs 100 | qs 100 | qs 100 | qs 100 | qs 100 | qs 100 | qs 100 |

| Component | | | | | | | | | |
|---|---|---|---|---|---|---|---|---|---|
| LACE Cl | — | — | — | — | — | — | — | — | — |
| LACE Tosylate | 2.2 | 2.1 | 3.5 | 3.65 | 4.8 | 6.4 | 2.2 | 4.8 | 4.79 |
| LACE equivalent | 1.3 | 1.3 | 2.3 | 2.30 | 3 | 4 | 1.3 | 3 | 3.00 |
| HP-β-CD | 6.3 | 6.7 | 11.2 | 11.5 | 15 | 19.6 | 6.3 | 15 | 15.0 |
| HPMC | 0.5 | 0.5 | 0.5 | 0.5 | 0.5 | 0.5 | 0.5 | 0.5 | 0.5 |
| Benzalkonium chloride (preservative) | 0.02 | — | — | — | 0.02 | 0.02 | 0.01 | 0.01 | — |
| Sorbic Acid | — | — | — | — | — | — | 0.1 | 0.1 | — |
| NaCl | 0.5 | 0.53 | 0.27 | 0.28 | 0.25 | — | 0.5 | 0.25 | 0.10 |
| Glycerin | — | — | — | — | — | — | — | — | — |
| PEG 300 | — | — | — | — | — | — | — | — | — |
| Alanine | — | — | — | — | — | — | — | — | — |
| NaOAc (buffer) | 0.07 | 0.07 | 0.07 | 0.07 | 0.07 | 0.07 | 0.07 | 0.07 | 0.07 |
| NaOH/HCL (pH adjust) | pH 4.5 | pH 4.5 | pH 4.5 | pH 4.5 | pH 4.5 | pH 4.5 | pH 4.5 | pH 4.5 | pH 4.5 |
| Purified Water | qs 100 | qs 100 | qs 100 | qs 100 | qs 100 | qs 100 | qs 100 | qs 100 | qs 100 |

Example 17. Effect of Various Excipients on Ocular Bioavailability of Lipoic Acid In order to test the effect of various excipients on ocular bioavailability of lipoic acid, various pharmaceutical compositions of 2.1% LACE tosylate (1.3% LACE) were prepared and tested in rabbits.

The tests were carried out using the following procedure: The dose formulation containers were kept on wet ice during the dosing period and individual doses were allowed to equilibrate to ambient temperature for several minutes prior to dose administration. Animals received a single topical ocular dose to both eyes. The topical dose was administered to the central, superior part of the cornea of the right and left eye via a positive displacement pipette on a fixed basis (35 μL/eye) and was allowed to spread across the surface of the eye. After the dose was administered, the eye was allowed to close naturally. Each animal was restrained for approximately 1 minute to prevent rubbing of the eyes.

Two animals were sacrificed at each time point (0.25, 0.5, 1, and 2 hours), both eyes were enucleated, and the appropriate tissues were collected for both right and left eyes. After the weight of the tissue sample was determined, the tissue sample was snap-frozen in liquid nitrogen and then stored on dry ice until storage at approximately −80° C.

For the preparation of cornea samples, 3% (w/v) bovine milk in Milli-Q water was prepared by reconstituting 3 g dried bovine milk with 100 mL water. Cornea samples and ice-cold 3% bovine milk were combined in a ratio of 9 mL milk to 1 g tissue (dilution factor=10) in OmniPrep 2-mL pre-loaded tubes. Samples were bead-mill homogenized in the BeadRuptor at 6 m/s for 1 minute with a 30 second dwell for 4 cycles (tube holder was pre-chilled on dry ice).

A 10-μL aliquot of each sample (calibration standards, quality controls, blanks and study samples) was transferred into a 96-well extraction plate according to a pre-defined layout. An 80-μL aliquot of internal standard spiking solution (100 ng/mL each of anandamide-d4, atenolol, carbamazepine, chrysin, glafenine, dexamethasone, carbutamide, and glyburide in acetonitrile) was added into all wells except the wells for the matrix blanks, to which an 80-µL aliquot of acetonitrile was added per well. The plate was covered, vortex-mixed, and then centrifuged at >3000 rpm (2103×g) at 4° C. for 5 minutes. Supernatant (70 µL) was transferred into the corresponding wells of a clean 96-well plate and then evaporated to dryness at approximately 40° C. under a nitrogen stream. The dried residue was reconstituted in 100 µL of 0.1% (v/v) formic acid in water. The plate was covered, vortex-mixed, and stored at approximately 4° C. until injected.

Lipoic Acid Instrumental Conditions:
Column: ACE Excel SuperC18 (50×2.1 mm, 1.7 µm)
Column oven: 50° C.
Solvent A: 5:95:0.1 (v:v:v) acetonitrile:water:formic acid
Solvent B: 50:50:0.1 (v:v:v) methanol:acetonitrile:formic acid
Injection volume: 15 µL
Flow rate: 0.9 mL/min
The column effluent diverted to the MS source between 0.20 min to 1.80 min
The LC gradient was as follows:

| Time (min) | % A | % B |
| --- | --- | --- |
| 0.00 | 60 | 40 |
| 0.20 | 60 | 40 |
| 1.80 | 55 | 45 |
| 1.90 | 5 | 95 |
| 2.40 | 5 | 95 |
| 2.50 | 60 | 40 |
| 2.70 | 60 | 40 |

Lipoic acid choline ester instrumental conditions:
Column: ACE Excel SuperC18 (50×2.1 mm, 1.7 µm)
Column oven: 50° C.
Solvent A: 100:0.1 (v:v) water:formic acid
Solvent B: 100:0.1 (v:v) acetonitrile:formic acid
Injection volume: 2 µL
Flow rate: 0.9 mL/min
The column effluent diverted to the MS source between 0.20 min to 1.20 min
The LC solvent gradient was as follows:

| Time (min) | % A | % B |
| --- | --- | --- |
| 0.00 | 80 | 20 |
| 0.20 | 80 | 20 |
| 1.10 | 30 | 70 |
| 1.20 | 5 | 95 |
| 1.70 | 5 | 95 |
| 1.80 | 80 | 20 |
| 2.00 | 80 | 20 |

Results of lipoic acid levels in ocular tissues are shown in Table 20.

TABLE 20

Lipoic acid level in rabbit ocular tissues after administration of pharmaceutical compositions that include 2.1% LACE tosylate (1.3% LACE)

| Excipient tested | Formulation | AUC Aq. humor (hr * ng/ml) | AUC cornea (hr * ng/ml) | AUC conjunctiva (hr * ng/ml) | Cmax Aq. humor (ng/ml) | Conclusion (Aq. humor) |
| --- | --- | --- | --- | --- | --- | --- |
| Effect of chloride counterion | 6.3% HPbCD, 0.0% NaCl | 66 | 140 | 2804 | 211 | |
| | 6.3% HPbCD, 0.5% NaCl | 92* | 327 | 2916 | 333 | No effect of chloride ion on ocular bioavailability |
| | 6.3% HPbCD, 1.0% NaCl | 43 | 224 | 2373 | 124 | |
| Addition of BAK (Also serves as a comparator for HPMC and alanine effects) | 6.3% HPbCD, 0.5% NaCl, 0.02% BAC | 99 | 290 | 2141 | 381 | No effect of BAK on lipoic acid ocular availability |
| Addition of HPMC | 6.3% HPbCD, 0.5% NaCl, 0.02% BAC, 0.5% HPMC | 57 | 373 | 4709 | 192 | No increase in lipoic acid bioavailability with HPMC at 1.3% LACE |
| Addition of Alanine | 6.3% HPbCD, 0.5% NaCl, 0.02% BAC, 0.5% Alanine | 36 | 226 | 1347 | 83 | Alanine does not increase lipoic acid bioavailability |
| Addition of sorbic acid | 6.3% HPbCD, 0.5% NaCl, 0.01% BAC, 0.5% HPMC, 0.1% Sorbic Acid | 114* | 165 | 3202 | 326 | No clear effect of sorbic acid on lipoic acid bioavailability in a formulation with HPMC |

TABLE 20-continued

Lipoic acid level in rabbit ocular tissues after administration of pharmaceutical compositions that include 2.1% LACE tosylate (1.3% LACE)

| Excipient tested | Formulation | AUC Aq. humor (hr * ng/ml) | AUC cornea (hr * ng/ml) | AUC conjunctiva (hr * ng/ml) | Cmax Aq. humor (ng/ml) | Conclusion (Aq. humor) |
|---|---|---|---|---|---|---|
| HPbCD + PEG 400 | 6.3% HPbCD, 0.5% NaCl | 92 | 327 | 2916 | 333 | |
| | 3.1% HPbCD, 5.3% PEG400 | 100* | 1039 | 5719 | 257 | No clear effect of reduced HPbCD |
| LACE chloride formulation | 1.3% LACE (Cl), 1.5% Glycerin, 0.5% Alanine, 0.005% BAC | 59 | 398 | 6021 | 88 | Control |

Next, LACE tosylate pharmaceutical compositions having higher LACE concentrations were evaluated for rabbit ocular bioavailability of lipoic acid using the methods described above. The results are shown in Table 21 below.

TABLE 21

Ocular bioavailability of lipoic acid at higher strength LACE tosylate formulations

| Principle | Fomulations | AUC Aq. humor (hr * ng/ml) | Cmax Aq. humor (ng/ml) | AUC Cornea (hr * ng/ml) | Cmax Cornea (ng/ml) | AUC conjunctiva (hr * ng/ml) | Cmax Conjunctiva (ng/ml) |
|---|---|---|---|---|---|---|---|
| Fomulation without HPMC | 2.2% LACE-OTs, 6.3% HPbCD, 0.5% NaCl, 0.02% BAC | 99 | 381 | 290 | 970 | 2141 | 5080 |
| Inclusion of HPMC | 2.2% LACE-OTs, 6.3% HPbCD, 0.50% NnCl, 0.02% BAC, 0.5% HPMC | 57 | 192 | 373 | 1156 | 4609 | 8075 |
| | 4.8% LACE-OTs, 15% HPbCD, 0.25% NaCl, 0.02% BAC, 0.5% HPMC | 220 | 702 | 1019 | 3045 | 6048 | 13960 |
| | 6.4% LACE-OTs, 19.6% HPbCD, 0.0% NaCl, 0,02% BAC, 0.5% HPMC | 743 | 1640 | 1431 | 3695 | 9264 | 12465 |
| BAC + Sorbic acid | 2.2% LACE-OTs, 6.3% HPbCD, 0.50% NaCl, 0.01% BAC., 0.5% HPMC, 0.1% Sorbic Acid | 114 | 326 | 165 | 228 | 3202 | 5008 |
| | 4.8% LACE-OTs, 15% HPbCD, 0.25% NaCl, 0.01% BAC, 0.5% HPMC, 0.1% Sorbic Acid | 410 | 1409 | 920 | 2150 | 6173 | 9247 |
| LACE chloride formulation | 1.5% LACE-Cl, 15% Glycerin 0.5% , Alanine, 0.005% BAC | 59 | 88 | 398 | 349 | 6021 | 10955 |
| | 1.5% LACE-Cl, 6.3% HPbCD, 0.07% NaOAc, 0.02% BAC | 19 | 42 | 389 | 309 | 8660 | 4871 |
| | 3.3% LACE-Cl, 15% HPbCD, 0.07% NaOAr, 0.02% BAC | 235 | 134 | 3540 | 1621 | 11580 | 5582 |

As seen in the results from Table 21, HPMC had limited contribution at lower concentrations but enhanced ocular bioavailability of lipoic acid in anon-linear manner at higher concentrations of LACE-tosylate and LACE chloride.

In order to evaluate the effect of HPMC, pharmaceutical compositions with and without HPMC were prepared and compared for bioavailability of LACE and lipoic acid in cornea and aqueous humor, using the methods described above. Results (reported as mean values for four measurements) are shown in Table 22.

TABLE 22

Pharmacokinetic parameters for lipoic acid and LACE in aqueous humor and cornea for different pharmaceutical compositions with and without HPMC

| | 1.5% LACE-Cl, 1.5% Glycerin, 0.5% Alanine, 0.005% BAC | 2.2% LACE-OTs, 6.3% HPbCD, 0.5% NaCl, 0.02% BAC | | 4.8% LACE-OTs, 15% HPbCD, 0.25% NaCl, 0.02% BAC | | 6.4% LACE-OTs, 19.6% HPbCD, 0.0% NaCl, 0.02% BAC | |
|---|---|---|---|---|---|---|---|
| | | w/o 0.5% HPMC | with 0.5% HPMC | w/o 0.5% HPMC | with 0.5% HPMC | w/o 0.5% HPMC | with 0.5% HPMC |
| Aqueous humor (lipoic acid) | | | | | | | |
| AUClast (h * ng/ml) | 60 | 44.8 | 57.9 | 41.9 | 217 | 125 | 1030 |
| Cmax (ng/ml) | 220 | 181 | 126 | 39.8 | 1150 | 301 | 3310 |
| Tmax (hour) | 0.25 | 0.25 | 0.25 | 0.25 | 0.25 | 0.25 | 0.25 |
| Aqueous humor (LACE) | | | | | | | |
| AUClast (h * ng/ml) | 0.382 | 0.144 | 1.17 | 19.1 | 3.28 | 0.504 | 15.9 |
| Cmax (ng/ml) | 0.449 | 0.415 | 2.35 | 74.8 | 11.3 | 0.892 | 66.7 |
| Tmax (hour) | 0.25 | 0.25 | 0.50 | 1.0 | 0.25 | 0.25 | 0.25 |
| Cornea (lipoic acid) | | | | | | | |
| AUClast (h * ng/ml) | 395 | 264 | 645 | 567 | 1260 | 729 | 3720 |
| Cmax (ng/ml) | 859 | 667 | 1530 | 649 | 5940 | 1670 | 15300 |
| Tmax (hour) | 0.25 | 0.25 | 0.25 | 1.0 | 0.25 | 0.25 | 0.25 |
| Cornea (LACE) | | | | | | | |
| AUClast (h * ng/ml) | 92.9 | 32.3 | 77.4 | 48.2 | 150 | 492 | 693 |
| Cmax (ng/ml) | 129 | 82.5 | 178 | 96.3 | 653 | 802 | 3230 |
| Tmax (hour) | 0.25 | 0.25 | 0.25 | 0.25 | 0.25 | 0.25 | 0.25 |

As seen in Table 22 above, inclusion of HPMC nonlinearly increased bioavailability of lipoic acid and LACE at higher LACE concentrations in the tested formulations.

Example 18. Stability Testing of LACE Tosylate Formulations

Various LACE tosylate pharmaceutical compositions were tested for stability under different conditions of temperature and time periods and under accelerated testing conditions. The results are shown in Table 23 below as a percentage of the initial amount of LACE in the formulation. The stability of a LACE chloride formulation is provided for purposes of comparison. As seen below, LACE tosylate pharmaceutical compositions were more stable than a LACE chloride formulation under accelerated stability testing (13 Weeks at 40° C.).

The stability was maintained in pharmaceutical compositions with and without HPMC.

TABLE 23

Formulation stability data - 10 week assay

| | 5° C. for 10 weeks | | | 25° C. for 10 weeks | | | 40° C. for 10 weeks | | |
|---|---|---|---|---|---|---|---|---|---|
| | % Initial | Lipoic Acid (% Area) | Other Degs (% Area) | % Initial | Lipoic Acid (% Area) | Other Degs (% Area) | % Initial | Lipoic Acid (% Area) | Other Degs (% Area) |
| 1.5% LACE-Cl, 0.5% Alanine, 1.4% Glycerine, 0.005% BAC pH 4.5 | 99.23% | 0.12% | 1.17% | 96.87% | 1.12% | 2.48% | 82.09% | 6.21% | 13.65 |
| 2.2% LACE-OTs, 0.07% Acetate, 3.15% HPbCD, 5.3% PEG-300 pH 4.5 | 96.27% | 0.28% | — | 97.80% | 0.93% | — | 86.47% | 6.08% | 0.91% |
| 2.2% LACE-OTs, 0.07 Acetate, 6.3% HPbCD, 0.5% NaCl pH 4.5 | 99.43% | 0.20% | — | 98.00% | 0.00% | — | 89.7% | 5.70% | 0.48% |
| 2.2% LACE-OTs, 0.07% Acetate, 6.3% HPbCD pH 4.5 | 99.70% | 0.24% | — | 98.36% | 1.00% | — | 89.00% | 6.54% | 0.59% |
| 2.2% LACE-OTs, 0.07% Acetate, 6.3% HPbCD, 0.5% NaCl, 0.02% BAC pH 4.5 | 99.97% | 0.26% | — | 98.75% | 0.93% | — | 90.28% | 5.64% | 0.46% |
| 2.2% LACE-OTs, 6.3% HPbCD, 0.5% Alanine, 0.02% BAC pH 4.5 | 100.98% | 0.28% | — | 99.48% | 0.95% | — | 91.42% | 6.01% | 0.52% |
| 2.2% LACE-OTs, 0.07% Acetate, 6.3% HPbCD, 1.0% NaCl, pH 4.5 | 99.41% | 0.32% | — | 98.19% | 1.01% | — | 89.89% | 5.95% | 0.49% |
| 2.2% LACE-OTs, 0.07% Acetate, 6.3% HPbCD, 05% NaCl, 0.5% HPMC, 0.02% BAC pH 4.5 | 99.03% | 0.24% | — | 97.83% | 0.92% | — | 87.74% | 5375% | 0.50% |
| 4.8% LACE-OTs, 0.07% Acetate, 15% HPbCD, 0.5% HPMC, 0.25% NaCl, 0.02% BAC pH 4.5 | 98.27% | 0.26% | — | 96.31% | 0.91% | — | 90.00% | 5.37% | 0.34% |
| 6.4% LACE-OTs, 0.07% Acetate, 19.6% HPbCD, 0.5% HPMC, 0.02% BAC pH 4.5 | 96.95% | 0.32% | — | 97.47% | 0.86% | — | 91.47% | 5.17% | 0.30% |
| 2.2% LACE-OTs, 0.07% Acetate, 6.3% HPbCD, 0.5% HPMC, 0.1% Sorbic Acid, 0.5% NaCl, 0.01% BAC pH 4.5 | 97.68% | 0.36% | 0.67% | 97.09% | 1.20% | 1.22% | 87.15% | 6.47% | 3.48% |
| 4.8% LACE-OTs, 0.07% Acetate, 15% HPbCD, 0.5% HPMC, 0.25% NaCl, 0.1% Sorbic Acid, 0.01% BAC pH 4.5 | 95.52% | 0.41% | 0.25% | 94.34% | 1.19% | 0.69% | 85.87% | 6.42% | 2.22% |
| 1.5% LACE-Cl, 0.07% Acetate, 6.3% HPbCD, 0.5% NaCl, 0.02% BAC pH 4.5 | 99.07% | 0.37% | 0.28% | 98.12% | 1.01% | 1.13% | 90.30% | 5.40% | 5.23% |
| 3.3% LACE-Cl, 0.07% Acetate, 15% HPbCD, 0.25% NaCl, 0.02% BAC pH 4.5 | 98.52% | 0.40% | 0.24% | 97.96% | 1.00% | 1.00% | 89.41% | 5.09% | 4.58% |

Further stability studies on selected formulations are shown below in Table 24.

TABLE 24

Stability of LACE tosylate pharmaceutical compositions in 13 week studies

| Sample | 13 Weeks @ 5° C. % of Initial | 13 Weeks @ 25° C. % of Initial | 13 Weeks @ 40° C. % of Initial |
|---|---|---|---|
| 1.5% LACE-Cl, 0.5% Alanine, 1.4% Glycerin, 0.005% BAC pH 4.5 | 99% | 95% | 76% |
| 2.2% LACE-OTs, 0.07% Acetate, 6.3% HPbCD, 0.5% NaCl, 0.02% BAC, pH 4.5 | 100% | 98% | 88% |
| 2.2% LACE-OTs, 0.07% Acetate, 6.3% HPbCD, 0.5% NaCl, 0.5% HPMC, 0.02% BAC, pH 4.5 | 100% | 97% | 87% |
| 4.8% LACE-OTs, 0.07% Acetate, 15% HPbCD,, 0.25% NaCl, 0.5% HPMC, 0.02% BAC pH 4.5 | 99% | 98% | 88% |
| 6.4% LACE-OTs, 0.07% Acetate, 19.6% HPbCD, 0.5% HPMC, 0.02% BAC pH 4.5 | 97% | 97% | 88% |

As seen in Table 23 and Table 24, pharmaceutical compositions containing LACE tosylate and HPBCD showed stability under accelerated stability conditions that would enable long term storage at ambient or refrigerated conditions. The stability data combined with the manufacturability of LACE tosylate and increased bioavailability using HPMC led the inventors to conclude that LACE tosylate pharmaceutical compositions with HPMC and HPBCD would be suitable for clinical studies.

Example 19. Effect of BAC with Tosylate and Sodium Chloride

The present inventors observed that LACE tosylate pharmaceutical compositions with benzalkonium chloride (BAC) and sodium chloride formed small crystalline particles that were about 200-400 microns in length. The crystals redissolved when the formulation was allowed to warm up to room temperature. As seen in Table 25 pharmaceutical compositions that included LACE tosylate, benzalkonium chloride, and sodium chloride formed crystalline particles upon refrigeration.

Figure 15:
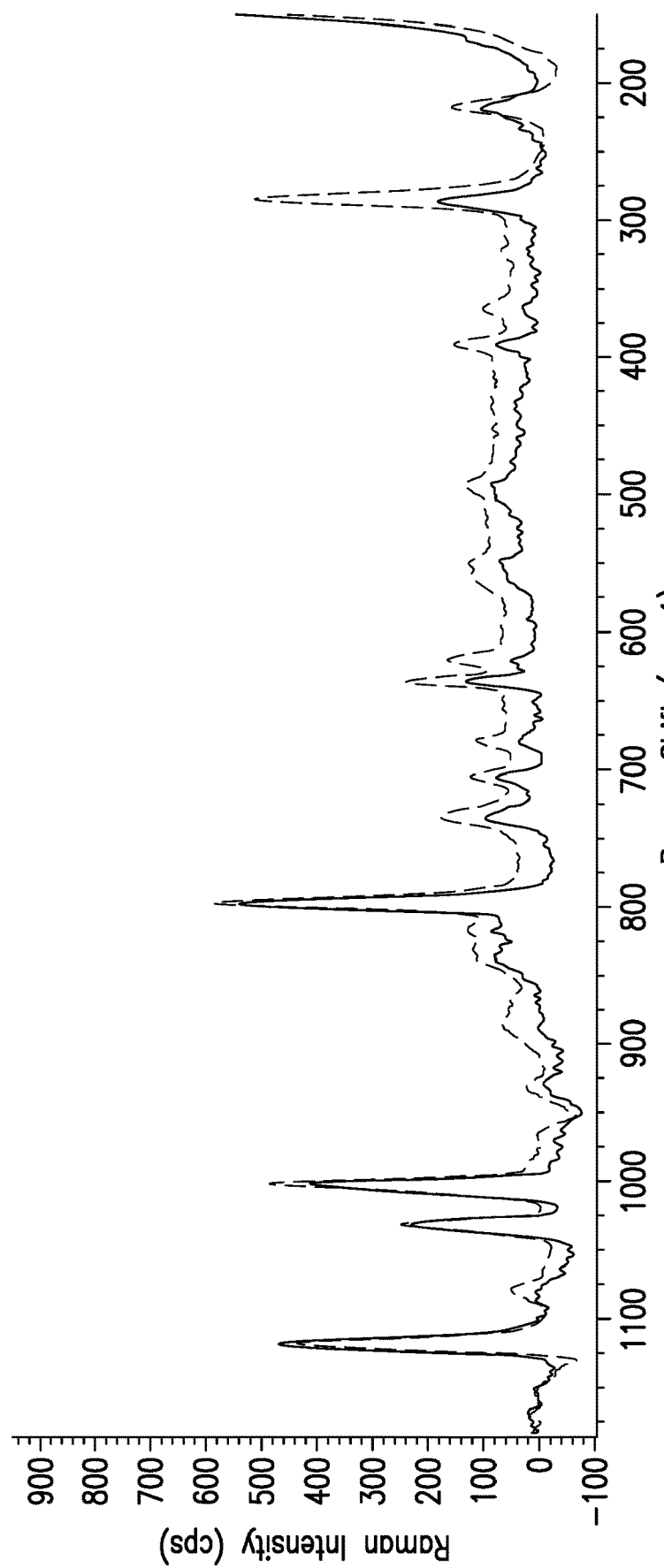
FIG. 15 provides an X-ray diffraction pattern of crystals isolated from LACE tosylate, BAC, and NaCl formulations, with those from a reference formulation that includes sodium tosylate, 0.02% BAC, and 0.5% NaCl.

In order to determine the structure of the crystalline particles, a vehicle formulation with sodium tosylate, 0.02% BAC, and 0.5% NaCl was prepared. This formulation also formed crystalline particles upon refrigeration. Raman analysis of the crystals (FIG. 15) observed in the drug product overlaid with the crystals from the vehicle sodium tosylate formulations, and confirmed that these particles contain BAC and tosylate and do not contain LACE.

TABLE 25

LACE pharmaceutical compositons exhibiting particulate crystalling matter

| Component | Percent w/v | | | | | | | | | | | | | |
|---|---|---|---|---|---|---|---|---|---|---|---|---|---|---|
| LACE Cl | 1.5 | 1.5 | 3.3 | — | — | — | — | — | — | — | — | — | — | — |
| LACE-OTs | — | — | — | 2.2 | 2.2 | 2.2 | 2.2 | 2.2 | 2.2 | 2.2 | 4.8 | 6.4 | 2.2 | 4.8 |
| HP-β-CD | — | 6.3 | 15 | 6.3 | 6.3 | 3.15 | 6.3 | 6.3 | 6.3 | 6.3 | 15 | 19.6 | 6.3 | 15 |
| HPMC | — | — | — | — | — | — | — | — | — | 0.5 | 0.5 | 0.5 | 0.5 | 0.5 |
| BAC | 0.005 | 0.02 | 0.02 | 0.02 | 0.02 | — | — | — | — | 0.02 | 0.02 | 0.02 | 0.01 | 0.01 |
| Sorbic Acid | — | — | — | — | — | — | — | — | — | — | — | — | 0.1 | 0.1 |
| NaCl | — | 0.5 | 0.25 | 0.5 | 0.5 | — | — | 0.5 | 1.0 | 0.5 | 0.25 | — | 0.5 | 0.25 |
| Glycerin | 1.4 | — | — | — | — | — | — | — | — | — | — | — | — | — |
| PEG 300 | — | — | — | — | — | 5.3 | — | — | — | — | — | — | — | — |
| Alanine | 0.5 | — | — | — | 0.5 | — | — | — | — | — | — | — | — | — |
| NaOAc | — | 0.07 | 0.07 | 0.07 | — | 0.07 | 0.07 | 0.07 | 0.07 | 0.07 | 0.07 | 0.07 | 0.07 | 0.07 |
| HCl | pH 4.5 | pH 4.5 | pH 4.5 | pH 4.5 | pH 4.5 | pH 4.5 | pH 4.5 | pH 4.5 | pH 4.5 | pH 4.5 | pH 4.5 | pH 4.5 | pH 4.5 | pH 4.5 |
| Purified Water | qs 100 | qs 100 | qs 100 | qs 100 | qs 100 | qs 100 | qs 100 | qs 100 | qs 100 | qs 100 | qs 100 | qs 100 | qs 100 | qs 100 |
| Particulates | No | No | No | Yes | Yes | No | No | No | No | Yes | Yes | No | No | No |

Example 20. Antimicrobial Efficacy Testing of Preserved and Unpreserved LACE Tosylate Formulations As described above, pharmaceutical compositions containing LACE tosylate, benzalkonium chloride, and sodium chloride formed crystalline particles upon refrigeration. In contrast, pharmaceutical compositions that did not include BAC did not form crystalline particles. Accordingly, the present inventors investigated other preservatives in LACE tosylate formulations. Biguanide was evaluated as a preservative but was not found to be efficacious due to binding to cyclodextrin. Accordingly, pharmaceutical compositions that included boric acid or sorbic acid or that did not include any preservative were tested under US Pharmacopoeia standards for antimicrobial efficacy of the formulations.

The testing was carried out using the following procedure: Five different challenge organisms were evaluated (*Staphylococcus aureus, Pseudomonas aeruginosa, Escherichia coli, Candida albicans,* and *Aspergillus brasiliensis*) were evaluated for each test formulation, and inoculated to a concentration of $10^6$ colony forming units per ml (CFU/ml). The microbial suspension was incubated and sampled at 7, 14, 21, and 28 days. At the time of sampling, a sample was diluted 10-fold into tryptase soy broth medium, and 100 μl plated in growth agar plates to count survivors. The survivor count was used to determine log reduction. The preservative efficacy test criteria for multidose pharmaceutical compositions under US Pharmacopoeia standards are as follows.

| | | Log reduction | | | |
|---|---|---|---|---|---|
| PET Criteria | | 6 hr | 24 hr | 7 day | 14 day | 28 day |
| Bacteria | USP/JP | — | — | 1 | 3 | No Increase (from day 14) |
| Yeast/fungi | USP/JP | — | — | NI | NI | NI (from initial) |

NI = no increase

Results from the preservative efficacy test of unpreserved LACE tosylate pharmaceutical compositions are shown in Table 26.

TABLE 26

LACE tosylate pharmaceutical compositions preservative efficacy testing results

| Components (% w/v) | | | | | | | | | |
|---|---|---|---|---|---|---|---|---|---|
| Lace-OTs | 0.79 | 2.2 | 4.8 | 0 (Placebo) | 0 (Placebo) | 6.4 | 2.2 | 2.2 | 0.8 |
| Sodium acetate (trihydrate) | 0.07 | 0.07 | 0.07 | 0.07 | 0.07 | 0.07 | 0.07 | — | 0.07 |
| Hydroxypropyl-β-cyclodextrin | 2.5 | 6.3 | 15 | 19.6 | — | 19.6 | 6.3 | 6.3 | 2.5 |
| HPMC | 0.5 | 0.5 | 0.5 | 0.5 | 0.5 | — | 0.5 | — | 0.5 |
| Sodium chloride | 0.75 | 0.5 | 0.1 | 0.5 | 0.85 | — | — | 0.5 | 0.5 |
| Sorbic acid | — | — | — | — | — | — | 0.1 | 0.1 | 0.1 |
| Boric acid | — | — | — | — | — | 0.3 | — | — | — |
| BAC | — | — | — | — | 0.02 | — | — | — | — |
| pH | 4.5 | 4.5 | 4.5 | 4.5 | 4.5 | 4.5 | 4.5 | 4.5 | 4.5 |
| USP preservation | Pass | Pass | Pass | Fail | Pass | Pass | Pass | Pass | Pass |

As seen in Table 26, LACE tosylate pharmaceutical compositions unexpectedly met USP preservation requirements without a preservative or preservative aid. In contrast, unpreserved placebo did not meet USP preservative requirements while the placebo preserved with benzalkonium chloride met USP requirements.

Example 21. Method of Manufacture of LACE Tosylate Formulations

LACE tosylate pharmaceutical compositions described above were prepared using the following general procedure. A stock solution of HPMC in water for injection and a stock solution of LACE tosylate with equimolar amount of hydroxypropyl-beta-cylcodextrin in water for injection were prepared and sterilized by filtration. Appropriate amounts of the bulk solutions were mixed according to the final formulation, additional components (sodium acetate) added as stock solutions and final pH adjusted using concentrated sodium hydroxide or concentrated hydrochloric acid. Water for injection was added to final volume. The formulation is filled into appropriate packaging and terminally sterilized. The following precautions were observed during manufacture in order to prevent formation of associative species:
- LACE tosylate must be rapidly dissolved with strong mixing into the stock solutions
- LACE tosylate addition to water for injection must be done slowly, allowing each addition to rapidly, and completely dissolve before the next aliquot is added
- The LACE tosylate must be added to water, and not the reverse order.

All publications and patent documents cited herein are incorporated herein by reference as if each such publication or document was specifically and individually indicated to be incorporated herein by reference. The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the invention that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A pharmaceutical composition comprising:
   about 0.5% w/v to about 5% w/v (based on the lipoic acid choline ester cation) of lipoic acid choline ester tosylate having the structure

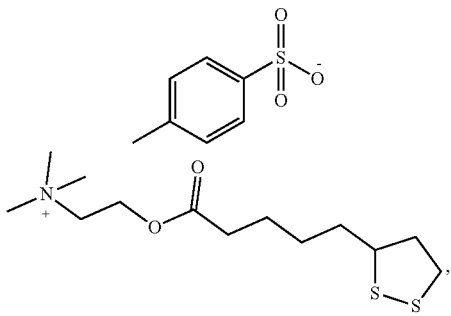

about 2% w/v to about 25% w/v of hydroxypropyl-β-cyclodextrin,
   up to 150 mM of an ionic tonicity agent or up to 300 mM of a nonionic tonicity agent,
   0.01% w/v to about 20% w/v of a viscosity modifying agent, and
   0.01% w/v to about 1% w/v of a buffer,
   wherein the pharmaceutical composition does not include a preservative and does not include a biochemical energy source.

2. The pharmaceutical composition according to claim 1, wherein the lipoic acid choline ester tosylate is substantially all (R)-lipoic acid choline ester tosylate.

3. The pharmaceutical composition according to claim 1, comprising about 0.5% w/v, about 1% w/v, about 1.1% w/v, about 1.2% w/v, about 1.3% w/v, about 1.4% w/v, about 1.5% w/v, about 2.0% w/v, about 2.3% w/v, about 2.5% w/v, about 3.0% w/v, about 3.5% w/v, about 4.0% w/v, about 4.5% w/v, or about 5% w/v of the lipoic acid choline ester cation.

4. The pharmaceutical composition according to claim 1, comprising about 0.5% w/v, about 1.3% w/v, about 1.4% w/v, about 2.3% w/v, about 3.0% w/v, or about 4.0% w/v of the lipoic acid choline ester cation.

5. The pharmaceutical composition according to claim 1, comprising about 2.5% w/v, about 3.2% w/v, about 3.3% w/v, about 6.3% w/v, about 6.7% w/v, about 11.2% w/v, about 11.5% w/v, about 15.0% w/v, or about 19.6% w/v of the hydroxypropyl-β-cyclodextrin.

6. The pharmaceutical composition according to claim 1, comprising about 1 mM to about 150 mM of an ionic tonicity agent selected from the group consisting of sodium chloride, potassium chloride, and mixtures thereof, or about 1 mM to about 300 mM of a nonionic tonicity agent selected from the group consisting of mannitol, dextrose, and mixtures thereof.

7. The pharmaceutical composition according to claim 1, wherein the ionic tonicity agent or the nonionic tonicity agent is selected from the group consisting of sodium chloride, potassium chloride, mannitol, dextrose, glycerin, propylene glycol and mixtures thereof.

8. The pharmaceutical composition according to claim 1, wherein the ionic tonicity agent comprises or is substantially all sodium chloride.

9. The pharmaceutical composition according to claim 1, comprising about 0.1% w/v, about 0.2% w/v, about 0.3% w/v, about 0.4% w/v, about 0.5% w/v, about 1% w/v, about 2% w/v, about 3% w/v, about 4% w/v, about 5% w/v, about 8% w/v, about 10% w/v, about 12% w/v, about 14% w/v, about 16% w/v, about 18% w/v, or about 20% w/v of the viscosity modifying agent.

10. The pharmaceutical composition according to claim 1, wherein the viscosity modifying agent is selected from the group consisting of polyethylene glycols, cellulosic agents, and mixtures thereof.

11. The pharmaceutical composition according to claim 1, wherein the viscosity modifying agent is selected from the group consisting of cellulosic agents and is present in an amount of about 0.01% w/v to about 1% w/v.

12. The pharmaceutical composition according to claim 1, wherein the viscosity modifying agent comprises or is substantially all hydroxypropylmethyl cellulose.

13. The pharmaceutical composition according to claim 1, wherein the buffer is selected from the group consisting of phosphate buffers, acetate buffers, citrate buffers, borate buffers, and Hank's Balanced Salt Solution (HBSS).

14. The pharmaceutical composition according to claim 1, wherein the buffer comprises or is substantially all acetate buffer.

15. The pharmaceutical composition according to claim 1 having a pH of about 4 to about 5.

16. The pharmaceutical composition according to claim 1, wherein the pharmaceutical composition is a sterile, aqueous solution.

17. The pharmaceutical composition according to claim 1, wherein the pharmaceutical composition meets US Pharmacopoeia preservation standards for sterile parenteral multi-dose compositions.

18. The pharmaceutical composition according to claim 1 having an osmolality of about 200 mOsm/kg to about 450 mOsm/kg.

19. A pharmaceutical composition comprising:
about 0.5% w/v, about 1.3% w/v, about 2.3% w/v, about 3% w/v, or about 4% w/v (based on the lipoic acid choline ester cation) of lipoic acid choline ester tosylate having the structure

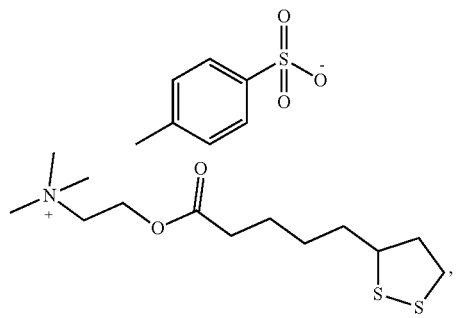

about 1.5% w/v, about 2.5% w/v, about 3.3% w/v, about 6.7% w/v, about 11.5% w/v, about 15.0% w/v, or about 19.6% w/v of hydroxypropyl-β-cyclodextrin,
about 0.1% w/v to about 1% w/v of sodium chloride,
about 0.1% w/v to about 0.75% w/v of hydroxypropyl-methyl cellulose, and
about 0.01% w/v to about 0.5% w/v of acetate buffer,
wherein the pharmaceutical composition has a pH of about 4.3 to about 4.7,
wherein the pharmaceutical composition has an osmolality of about 250 mOsm to about 425 mOsm,
wherein the pharmaceutical composition does not include a preservative and does not include alanine, and
wherein the pharmaceutical composition meets US Pharmacopoeia preservation standards for sterile parenteral multi-dose compositions.

20. The pharmaceutical composition according to claim 19, wherein the pharmaceutical composition is a sterile, aqueous solution.

21. The pharmaceutical composition according to claim 19, wherein the lipoic acid choline ester tosylate is substantially all (R)-lipoic acid choline ester tosylate.

22. The pharmaceutical composition according to claim 19, consisting of:
about 0.5% w/v, about 1.3% w/v, about 2.3% w/v, about 3% w/v, or about 4% w/v (based on the lipoic acid choline ester cation) of the lipoic acid choline ester tosylate,
about 1.5% w/v, about 2.5% w/v, about 3.3% w/v, about 6.7% w/v, about 11.5% w/v, about 15.0% w/v, or about 19.6% w/v of hydroxypropyl-β-cyclodextrin,
about 0.1% w/v to about 1% w/v of sodium chloride,
about 0.1% w/v to about 0.75% w/v of hydroxypropyl-methyl cellulose,
about 0.01% w/v to about 0.5% w/v of acetate buffer,
quantum satis sodium hydroxide pH of about 4.3 to about 4.7,
quantum satis hydrochloric acid pH of about 4.3 to about 4.7, and
quantum satis water.

23. Lipoic acid choline ester tosylate having the structure:

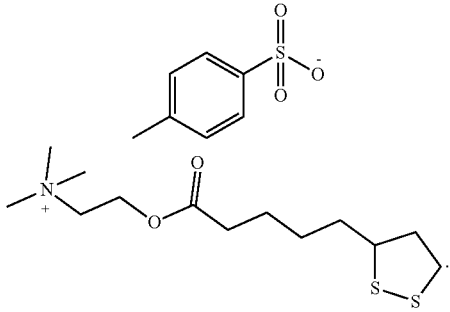

24. The compound according to claim 23, wherein the lipoic acid choline ester tosylate has the structure:

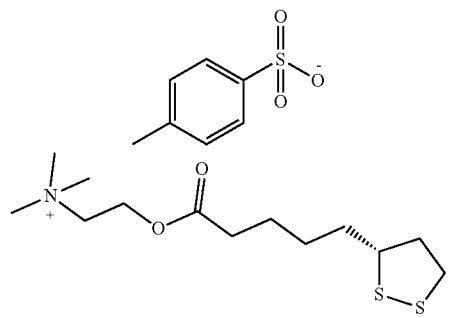

having at least 90% enantiomeric excess of the R isomer.

25. A crystal form A of lipoic acid choline ester (LACE) tosylate having the structure:

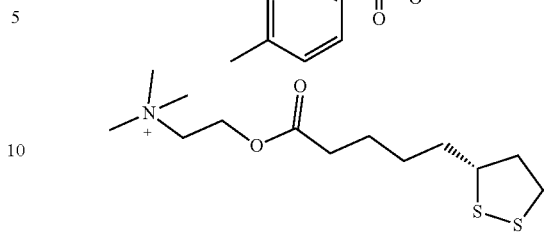

having at least 90% enantiomeric excess of the R isomer and characterized by an X ray diffraction pattern having three or more peaks at 2θ values selected from 21.9, 24.9, 25.9, 26.7, 27.1, 30.4, and 32.1±0.2° 2θ.

26. The crystal form A of LACE tosylate according to claim 25, characterized by an X ray diffraction pattern having four, five, six, or seven peaks at 2θ values selected from 11.4, 15.2, 18.4, 19.0, 19.4, 19.8, 21.9, 22.9, 24.9, 25.9, 26.7, 27.1, 29.6, 30.4, 32.1±0.2° 2θ.

27. The pharmaceutical composition according to claim 19, comprising about 0.5% w/v of the lipoic acid choline ester cation.

28. The pharmaceutical composition according to claim 19, comprising about 1.3% w/v of the lipoic acid choline ester cation.

29. The pharmaceutical composition according to claim 19, comprising about 2.3% w/v of the lipoic acid choline ester cation.

30. The pharmaceutical composition according to claim 19, comprising about 3.0% w/v of the lipoic acid choline ester cation.

* * * * *